US011967969B2

(12) United States Patent
Weerakoon et al.

(10) Patent No.: US 11,967,969 B2
(45) Date of Patent: Apr. 23, 2024

(54) CURRENT GENERATION ARCHITECTURE FOR AN IMPLANTABLE STIMULATOR DEVICE

(71) Applicant: Boston Scientific Neuromodulation Corporation, Valencia, CA (US)

(72) Inventors: Pujitha Weerakoon, Valencia, CA (US); Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 237 days.

(21) Appl. No.: 17/654,345

(22) Filed: Mar. 10, 2022

(65) Prior Publication Data
US 2022/0321139 A1    Oct. 6, 2022

Related U.S. Application Data

(60) Provisional application No. 63/171,329, filed on Apr. 6, 2021.

(51) Int. Cl.
*H03M 1/10* (2006.01)
*A61N 1/02* (2006.01)
(Continued)

(52) U.S. Cl.
CPC .......... *H03M 1/1061* (2013.01); *A61N 1/025* (2013.01); *A61N 1/0551* (2013.01); *A61N 1/08* (2013.01);
(Continued)

(58) Field of Classification Search
CPC ... H03M 1/1061; A61N 1/0551; A61N 1/378; A61N 1/08; A61N 1/14; A61N 1/36062;
(Continued)

(56) References Cited

U.S. PATENT DOCUMENTS 6,181,969 B1    1/2001  Gord
6,516,227 B1    2/2003  Meadows et al.
(Continued)

FOREIGN PATENT DOCUMENTS

EP      3456378 B1      1/2020
WO      2018/048914     3/2018
(Continued)

OTHER PUBLICATIONS

International Search Report and Written Opinion regarding corresponding PCT Application No. PCT/US2022/071074, dated Jun. 22, 2022.

*Primary Examiner* — Khai M Nguyen
(74) *Attorney, Agent, or Firm* — Lewis & Reese, PLLC

(57) ABSTRACT

Digital-to-Analog (DAC) circuitry for an implantable pulse generator is disclosed which is used to program currents at the electrodes. Calibration circuitry allows the positive and negative currents produced at each electrode to be independently calibrated to achieve an ideal (linear) response across a range of amplitude values provided to the DAC circuitry by a digital amplitude bus. The calibration circuitry includes electrode gain and electrode offset circuitry for each of the electrodes. Current range DAC circuitry is also provided which can be used to adjust the gain and offset current at all of the electrodes. The current range DAC circuitry is particularly useful when spanning a range of therapeutic currents for a patient, and allows all possible amplitude values provided by the digital bus to be used to span the range. This can improve (reduce) the current resolution of the electrode currents with each amplitude value step.

20 Claims, 47 Drawing Sheets

(51) Int. Cl.
*A61N 1/05* (2006.01)
*A61N 1/08* (2006.01)
*A61N 1/14* (2006.01)
*A61N 1/36* (2006.01)
*A61N 1/378* (2006.01)

(52) U.S. Cl.
CPC ............ *A61N 1/14* (2013.01); *A61N 1/36062* (2017.08); *A61N 1/36125* (2013.01); *A61N 1/36142* (2013.01); *A61N 1/378* (2013.01)

(58) Field of Classification Search
CPC . A61N 1/36125; A61N 1/36142; A61N 1/025
USPC ........................ 341/121, 135, 144
See application file for complete search history.

(56) References Cited

U.S. PATENT DOCUMENTS

| | | |
|---|---|---|
| 6,553,263 B1 | 4/2003 | Meadows et al. |
| 7,127,298 B1 | 10/2006 | He et al. |
| 7,177,698 B2 | 2/2007 | Klosterman et al. |
| 7,444,181 B2 | 10/2008 | Shi et al. |
| 7,539,538 B2 | 5/2009 | Parramon et al. |
| 7,623,916 B2 | 11/2009 | Julian |
| 7,801,600 B1 | 9/2010 | Carbunaru et al. |
| 7,801,602 B2 | 9/2010 | McClure et al. |
| 7,872,884 B2 | 1/2011 | Parramon et al. |
| 7,881,803 B2 | 2/2011 | Parramon et al. |
| 7,890,182 B2 | 2/2011 | Parramon et al. |
| 8,606,362 B2 | 12/2013 | He et al. |
| 8,620,436 B2 * | 12/2013 | Parramon ............ A61N 1/0551 607/46 |
| 8,649,858 B2 | 2/2014 | Griffith et al. |
| 8,768,453 B2 | 7/2014 | Parramon et al. |
| 9,002,465 B2 | 4/2015 | Ranu |
| 9,008,790 B2 | 4/2015 | Griffith et al. |
| 9,037,241 B2 | 5/2015 | Lamont et al. |
| 9,061,140 B2 | 6/2015 | Shi et al. |
| 9,155,891 B2 | 10/2015 | Archer |
| 9,174,051 B2 | 11/2015 | Marnfeldt et al. |
| 9,220,901 B2 | 12/2015 | Gururaj et al. |
| 9,233,254 B2 | 1/2016 | Nimmagadda et al. |
| 9,259,574 B2 | 2/2016 | Aghassian et al. |
| 9,259,578 B2 | 2/2016 | Torgerson |
| 9,308,373 B2 | 4/2016 | Lee |
| 9,314,632 B2 | 4/2016 | Marnfeldt et al. |
| 9,327,135 B2 | 5/2016 | Vansickle et al. |
| 9,352,162 B2 | 5/2016 | Lamont et al. |
| 9,397,639 B2 | 7/2016 | Feldman et al. |
| 9,446,241 B2 | 9/2016 | Lee |
| 9,522,270 B2 | 12/2016 | Perryman et al. |
| 9,604,061 B2 | 3/2017 | Archer |
| 10,716,941 B2 | 7/2020 | Yang et al. |
| 10,780,285 B2 | 9/2020 | Weerakoon et al. |
| 2002/0072770 A1 | 6/2002 | Pless |
| 2003/0139781 A1 | 7/2003 | Bradley et al. |
| 2003/0153959 A1 | 8/2003 | Thacker et al. |
| 2006/0173493 A1 | 8/2006 | Armstrong et al. |
| 2007/0038250 A1 | 2/2007 | He et al. |
| 2007/0100399 A1 | 5/2007 | Parramon et al. |
| 2010/0106231 A1 | 4/2010 | Torgerson et al. |
| 2010/0268309 A1 | 10/2010 | Parramon et al. |
| 2011/0160810 A1 | 6/2011 | Griffith |
| 2012/0092031 A1 | 4/2012 | Shi et al. |
| 2012/0095529 A1 | 4/2012 | Parramon et al. |
| 2013/0184794 A1 | 7/2013 | Feldman et al. |
| 2015/0134029 A1 | 5/2015 | Ozawa et al. |
| 2015/0144183 A1 | 5/2015 | Yang et al. |
| 2015/0157861 A1 | 6/2015 | Aghassian |
| 2016/0051825 A1 | 2/2016 | Ter-Petrosyan et al. |
| 2018/0071511 A1 | 3/2018 | Marnfeldt et al. |
| 2018/0071516 A1 | 3/2018 | Weiss et al. |
| 2018/0071520 A1 | 3/2018 | Weerakoon et al. |
| 2019/0083796 A1 | 3/2019 | Weerakoon et al. |
| 2019/0083797 A1 | 3/2019 | Weerakoon et al. |
| 2019/0275331 A1 | 9/2019 | Zhu |
| 2019/0299006 A1 | 10/2019 | Marnfeldt |
| 2020/0101291 A1 | 4/2020 | Yakovlev et al. |
| 2020/0406042 A1 * | 12/2020 | Weerakoon ........ A61N 1/36062 |
| 2021/0275798 A1 | 9/2021 | Marnfeldt |
| 2021/0299457 A1 | 9/2021 | Marnfeldt |

FOREIGN PATENT DOCUMENTS

| | | |
|---|---|---|
| WO | 2018/048923 | 3/2018 |
| WO | 2021/003290 A1 | 1/2021 |
| WO | 2021/119741 A1 | 6/2021 |

* cited by examiner

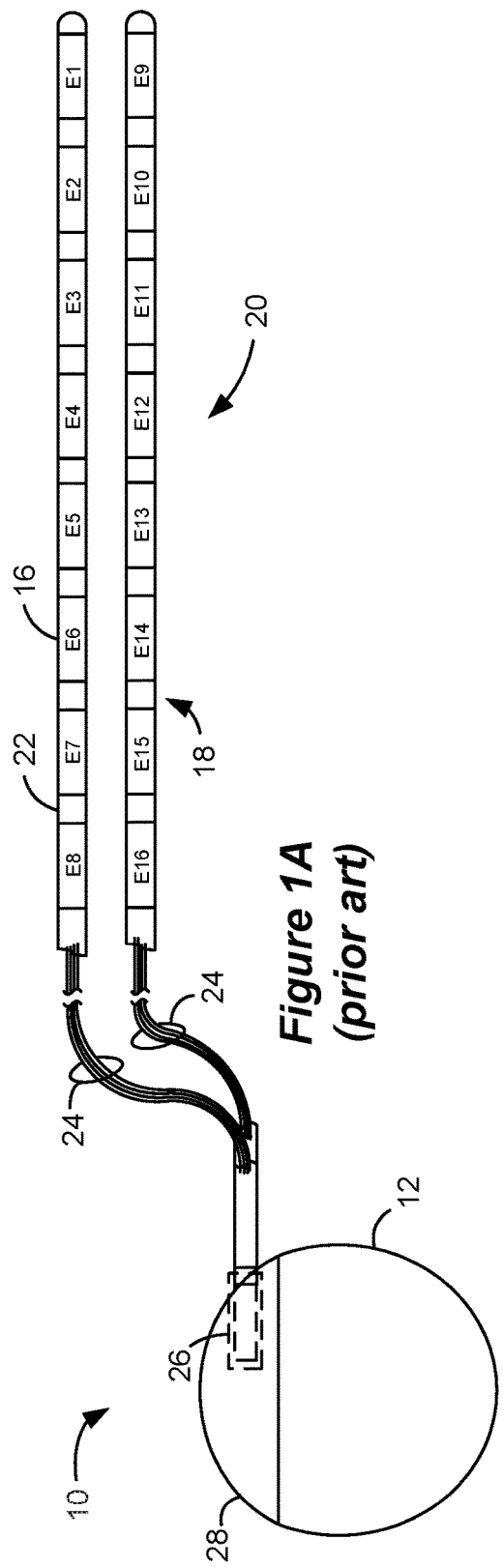
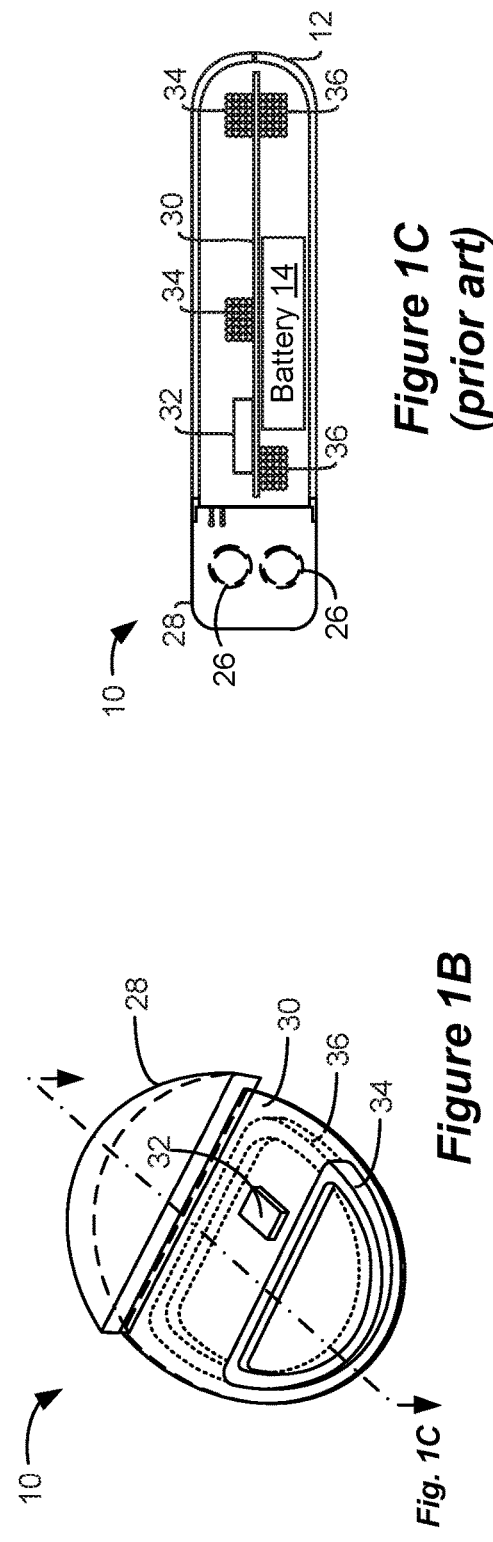
*Figure 1A (prior art)*
*Figure 1B (prior art)*
*Figure 1C (prior art)*

Electrode gain DAC 304:

| G_4 | G_3 | G_2 | G_1 | G_0 | decimal | Current at node 325 (•Iref) = electrode gain (G) |
|---|---|---|---|---|---|---|
| - | - | - | - | - | 0 | 0.8 |
| - | - | - | - | + | 1 | 0.8267 |
| - | - | - | + | - | 2 | 0.8533 |
| - | - | - | + | + | 3 | 0.88 |
| ⋮ | ⋮ | ⋮ | ⋮ | ⋮ | ⋮ | ⋮ |
| - | - | + | + | + | 7 | 0.9867 |
| - | + | - | - | - | 8 | 1.013 |
| - | + | - | - | + | 9 | 1.04 |
| - | + | - | + | - | 10 | 1.067 |
| ⋮ | ⋮ | ⋮ | ⋮ | ⋮ | ⋮ | ⋮ |
| + | + | + | - | - | 28 | 1.547 |
| + | + | + | - | + | 29 | 1.573 |
| + | + | + | + | - | 30 | 1.6 |
| + | + | + | + | + | 31 | 1.627 |

Electrode positive offset DAC 306p:

| OP_2 | OP_1 | OP_0 | decimal | Offset current added to node 325 (+O) assuming Iref = 100 nA |
|---|---|---|---|---|
| - | - | - | 0 | 0•Iref = 0 nA |
| - | - | + | 1 | 0.5•Iref = 50 nA |
| - | + | - | 2 | 1•Iref = 100 nA |
| ⋮ | ⋮ | ⋮ | ⋮ | ⋮ |
| + | - | + | 5 | 2.5•Iref = 250 nA |
| + | + | - | 6 | 3•Iref = 300 nA |
| + | + | + | 7 | 3.5•Iref = 350 nA |

Electrode negative offset DAC 306n:

| OP_2 | OP_1 | OP_0 | decimal | Offset current subtracted from node 325 (-O) assuming Iref = 100 nA |
|---|---|---|---|---|
| - | - | - | 0 | 0•Iref = 0 nA |
| - | - | + | 1 | 0.5•Iref = -50 nA |
| - | + | - | 2 | 1•Iref = -100 nA |
| ⋮ | ⋮ | ⋮ | ⋮ | ⋮ |
| + | - | + | 5 | 2.5•Iref = -250 nA |
| + | + | - | 6 | 3•Iref = -300 nA |
| + | + | + | 7 | 3.5•Iref = -350 nA |

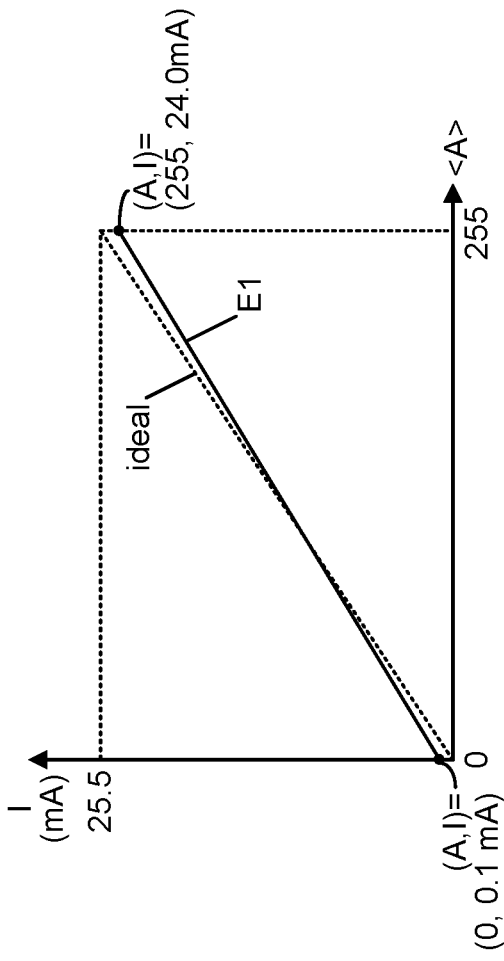

Non-ideal electrode offset of 0.1 mA; need negative offset of -0.1 mA

Assume PDAC1 amplifies A•Iref by 1000.

A*Iref provided to PDAC1 needs a negative offset of O = -0.1 µA or -100 nA.

This can be provided by negative electrode offset DAC 306n. The closest negative offset value to -100nA is -100nA (decimal 2, see Fig. 10D), which is produced by negative offset control signals:
 OpN1_2 = -
 OpN1_1 = +
 OpN1_0 = -

Non-ideal electrode slope of 0.0937; ideal slope is 0.1 (25.5/255)

A*Iref needs a gain G of 1.066 (0.1 / 0.0937)

This can be provided by the electrode gain DAC 304. The closest gain value to 1.066 is 1.067 (decimal 4, see Fig. 10D), which is produced by electrode gain control signals:
 Gp1_4 = -
 Gp1_3 = +
 Gp1_2 = -
 Gp1_1 = +
 Gp1_0 = -

Positive electrode offset DAC 306p is off (OpP1_2, _1, and _0) are all deasserted).

Global gain DAC 354:

| <B> asserted | decimal | Current at node 385 (•Iref) = global gain (B) |
|---|---|---|
| none | 0 | 0 |
| B_0 | 1 | 0.0125 |
| B_1 to B_0 | 2 | 0.025 |
| B_2 to B_0 | 3 | 0.0375 |
| ⋮ | ⋮ | ⋮ |
| B_24 to B_0 | 25 | 0.3125 |
| B_25 to B_0 | 26 | 0.325 |
| B_26 to B_0 | 27 | 0.3375 |
| ⋮ | ⋮ | ⋮ |
| B_78 to B_0 | 79 | 0.975 |
| B_79 to B_0 | 80 | 1 |
| B_80 to B_0 | 81 | 1.0125 |
| ⋮ | ⋮ | ⋮ |
| B_157 to B_0 | 158 | 1.975 |
| B_158 to B_0 | 159 | 1.9875 |
| B_159 to B_0 | 160 | 2 |

Global offset DAC 356:

| $\Delta\_4$ | $\Delta\_3$ | $\Delta\_2$ | $\Delta\_1$ | $\Delta\_0$ | decimal | Offset current ($\Delta$) assuming Iref = 100nA |
|---|---|---|---|---|---|---|
| - | - | - | - | - | 0 | 0•Iref = 0 nA |
| - | - | - | - | + | 1 | 10•Iref = 1 μA |
| - | - | - | + | - | 2 | 20•Iref = 2 μA |
| - | - | - | + | + | 3 | 30•Iref = 3 μA |
| - | - | + | - | - | 4 | 40•Iref = 4 μA |
| ⋮ | | | | | ⋮ | ⋮ |
| + | + | + | - | + | 29 | 290•Iref = 29 μA |
| + | + | + | + | - | 30 | 300•Iref = 30 μA |
| + | + | + | + | + | 31 | 310•Iref = 31 μA |

*Figure 11E*

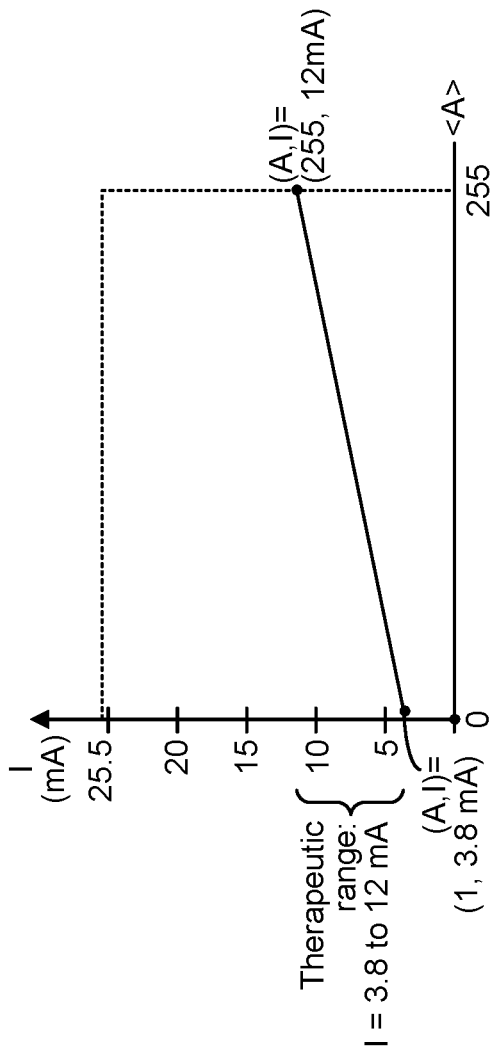

*Figure 11F*

Need an offset of +3.8 mA

Assume PDACs amplify A * B Iref by 1000.

The current at node 390 needs an global offset of Δ = 3.8 μA

This can be provided by global offset DAC 356p. The closest value to -3.8 μA is -4 μA (decimal 4, Fig. 11D), which is produced by global offset control signals:
Δ_4 = -
Δ_3 = -
Δ_2 = +
Δ_1 = -
Δ_0 = -

Nominal slope is 0.1 (25.5/255)

Need a slope of (12-3.8/255-1) = 0.0323

A*Iref needs a global gain B = 0.323 (0.0323/0.1)

This can be provided by the global gain DAC 354p. The closest gain value to 0.323 is 0.325 (decimal 26, Fig. 11D), which is produced by global gain control signals:
B_25 to B_0 = +
B_159 to B_26 = -

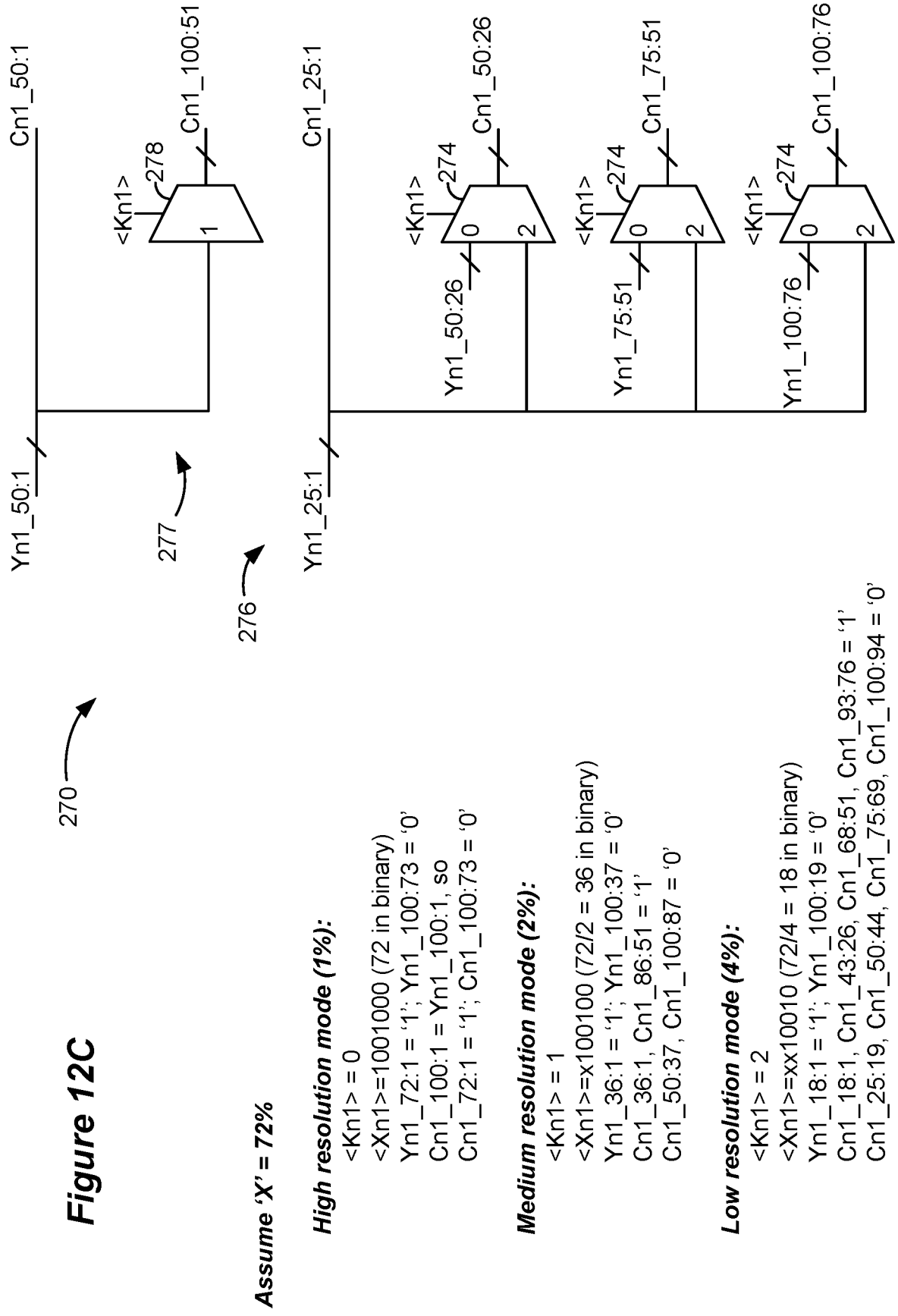

'A'=10 mA
Kn2 = Kn3 = '0' (high resolution mode)
<Xp1> = 100%,
<Xn1>, <Xp2>, <Xp3>, and all other <X> percentage busses for E4-E16 and Ec = 0%

|  | <Xn2> | E2 | <Xn3> | E3 |
|---|---|---|---|---|
| t0 | 100 (100%); Cn2_100:1 asserted | -10 mA | 0 (0%); Cn3_100:1 unasserted | 0 mA |
| t1 | 99 (99%); Cn2_99:1 asserted | -9.9 mA | 1 (1%); Cn3_1 asserted | -0.1 mA |
| t2 | 98 (98%); Cn2_98:1 asserted | -9.8 mA | 2 (2%); Cn3_2:1 asserted | -0.2 mA |
| t3 | 97 (97%); Cn2_97:1 asserted | -9.7 mA | 3 (3%); Cn3_3:1 asserted | -0.3 mA |
| t4 | 96 (96%); Cn2_96:1 asserted | -9.6 mA | 4 (4%); Cn3_4:1 asserted | -0.4 mA |
| ... | ... | ... | ... | ... |
| t97 | 3 (3%); Cn2_3:1 asserted | -0.3 mA | 97 (97%); Cn3_97:1 asserted | -9.7 mA |
| t98 | 2 (2%); Cn2_2:1 asserted | -0.2 mA | 98 (98%); Cn3_98:1 asserted | -9.8 mA |
| t99 | 1 (1%); Cn2_1 asserted | -0.1 mA | 99 (99%); Cn3_99:1 asserted | -9.9 mA |
| t100 | 0 (0%); Cn2_100:1 unasserted | 0 mA | 100 (100%); Cn3_100:1 asserted | -10 mA |

*Figure 13B*

'A'=10 mA
Kn2 = Kn3 = '1' (low resolution mode)
<Xp1> = 100%,
<Xn1>, <Xp2>, <Xp3>, and all other <X> percentage busses for E4-E16 and Ec = 0%

|  | <Xn2> | E2 | <Xn3> | E3 |
|---|---|---|---|---|
| t0 | 25 (100%); Cn2_100:1 asserted | -10 mA | 0 (0%); Cn3_100:1 unasserted | 0 mA |
| t1 | 24 (96%); Cn2_99:76, 74:51, 49:26, 24:1 asserted | -9.6 mA | 1 (4%); Cn3_76, 51, 26, 1 asserted | -0.4 mA |
| t2 | 23 (92%); Cn2_98:76, 73:51, 48:26, 23:1 asserted | -9.2 mA | 2 (8%); Cn3_77:76, 52:51, 27-26, 2:1 asserted | -0.8 mA |
| t3 | 22 (88%); Cn2_97:76, 72:51, 47:26, 22:1 asserted | -8.8 mA | 3 (12%); Cn3_78:76, 53:51, 28-26, 3:1 asserted | -1.2 mA |
| t4 | 21 (84%); Cn2_96:76, 71:51, 46:26, 21:1 asserted | -8.4 mA | 4 (16%); Cn3_79:76, 54:51, 29-26, 4:1 asserted | -1.6 mA |
| ... | | | | |
| t22 | 3 (12%;) Cn2_78:76, 53:51, 28-26, 3:1 asserted | -1.2 mA | 22 (88%); Cn3_97:76, 72:51, 47:26, 22:1 asserted | -8.8 mA |
| t23 | 2 (8%); Cn2_77:76, 52:51, 27-26, 2:1 asserted | -0.8 mA | 23 (92%); Cn3_98:76, 73:51, 48:26, 23:1 asserted | -9.2 mA |
| t24 | 1 (4%); Cn2_76, 51, 26, 1 asserted | -0.4 mA | 24 (96%); Cn3_99:76, 74:51, 49:26, 24:1 asserted | -9.6 mA |
| t25 | 0 (0%); Cn2_100:1 unasserted | 0 mA | 25 (100%); Cn3_100:1 asssertd | -10 mA |

*Figure 13C*

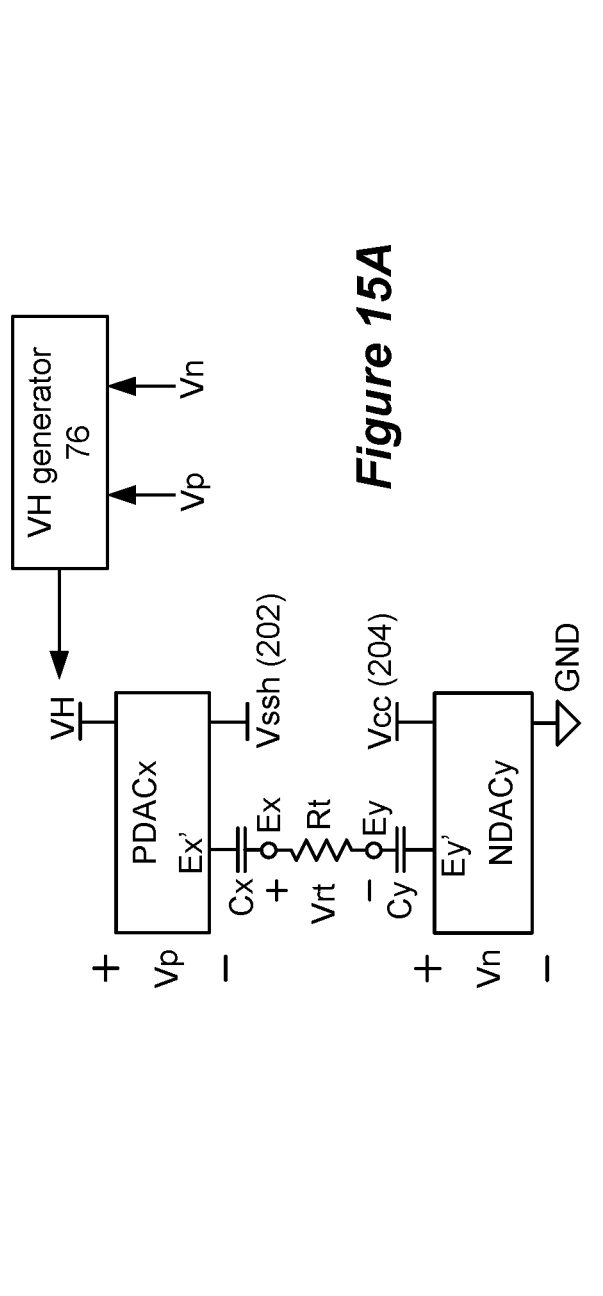
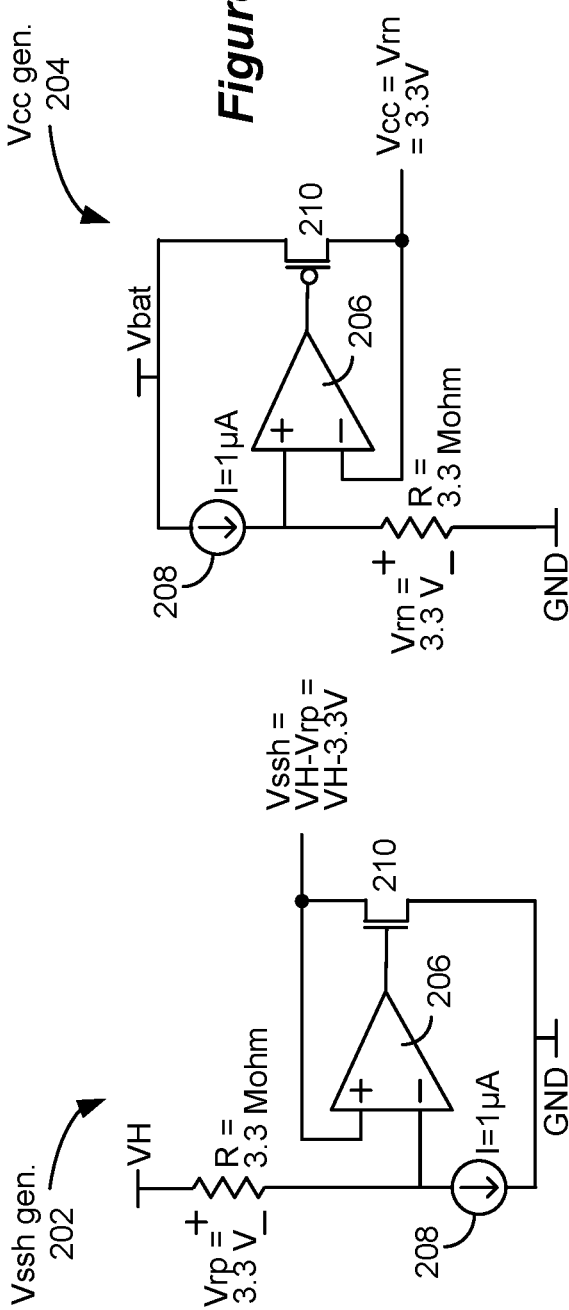
Figure 15A
Figure 15B

US 11,967,969 B2

CURRENT GENERATION ARCHITECTURE FOR AN IMPLANTABLE STIMULATOR DEVICE

CROSS REFERENCE TO RELATED APPLICATIONS

The is a non-provisional of U.S. Provisional Patent Application Ser. No. 63/171,329, filed Apr. 6, 2021, to which priority is claimed, and which is incorporated herein by reference in its entirety.

FIELD OF THE INVENTION

The present invention relates generally to medical devices, and more particularly to improved current generation architectures for an implantable pulse generator.

INTRODUCTION

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system, including a Deep Brain Stimulation (DBS) system.

As shown in FIGS. 1A-1C, an SCS system typically includes an Implantable Pulse Generator (IPG) 10, which includes a biocompatible device case 12 formed of a conductive material such as titanium for example. The case 12 typically holds the circuitry and power source (e.g., battery) 14 (FIG. 1C) necessary for the IPG 10 to function, although IPGs can also be powered via external RF energy and without a battery. The IPG 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ei) on two leads 18 for a total of sixteen electrodes 16, although the number of leads and electrodes is application specific and therefore can vary. The leads 18 couple to the IPG 10 using lead connectors 26, which are fixed in a non-conductive header material 28, which can comprise an epoxy for example.

As shown in the cross-section of FIG. 1C, the IPG 10 typically includes a printed circuit board (PCB) 30, along with various electronic components 32 mounted to the PCB 30, some of which are discussed subsequently. Two coils (more generally, antennas) are shown in the IPG 10: a telemetry coil 34 used to transmit/receive data to/from an external controller such as a clinician programmer or a hand-held patient programmer used to program stimulation in the IPG (not shown); and a charging coil 36 for charging or recharging the IPG's battery 14 using an external charger (not shown). FIG. 1B shows these aspects in perspective with the case 12 removed for easier viewing. Telemetry coil 34 may alternatively comprise a short range RF antenna for wirelessly communicating in accordance with a short-range RF standard such as Bluetooth, WiFi, MICS, Zigbee, etc., as described in U.S. Patent Application Publication 2016/0051825.

FIG. 2A shows a prior art architecture 40 for the circuitry in IPG 10, which is disclosed in U.S. Patent Application Publications 2012/0095529, 2012/0092031 and 2012/0095519 ("ASIC Publications"). Architecture 40 includes a microcontroller integrated circuit 50 and an Application Specific Integrated Circuit (ASIC) 60 in communication with each other by a bus 90. Stated simply, the microcontroller 50 provides master control for the architecture 40, while ASIC 60 takes commands from and provides data to the microcontroller. ASIC 60 provides specific IPG functionality. For example, and as explained in further detail below, ASIC 60 sends stimulation current to and reads measurements from the sixteen electrodes 16. ASIC 60 comprises a mixed mode IC carrying and processing both analog and digital signals, whereas microcontroller 50 comprises a digital IC carrying and processing only digital signals.

Microcontroller 50 and ASIC 60 comprise monolithic integrated circuits each formed on their own semiconductive substrates ("chips"), and each may be contained in its own package and mounted to the IPG 10's PCB 30. Architecture 40 may also include additional memory (not shown) for storage of programs or data beyond that provided internally in the microcontroller 50. Additional memory may be connected to the microcontroller 50 by a serial interface (SI) as shown, but could also communicate with the microcontroller 50 via bus 90. Bus 90 may comprise a parallel address/data bus, and may include a clock signal and various control signals to dictate reading and writing to various memory locations, as explained in the above-referenced '529 Publication. Bus 90 and the signals it carries may also take different forms; for example, bus 90 may include separate address and data lines, may be serial in nature, etc.

As explained in the above-referenced ASIC Publications, architecture 40 is expandable to support use of a greater number of electrodes 16 in the IPG 10. For example, and as shown in dotted lines in FIG. 2A, architecture 40 may include another ASIC 60' identical in construction to ASIC 60, thus expanding the number of electrodes supported by the IPG 10 from sixteen to thirty two. Various off-bus connections 54 (i.e., connections not comprising part of bus 90) can facilitate such expansion, and may further (e.g., by bond programming; see inputs M/S) designate ASIC 60 as a master and ASIC 60' as a slave. Such differentiation between the ASICs 60 and 60' can be useful, as certain redundant functionality in the slave ASIC 60' can be disabled in favor of the master ASIC 60. Off-bus communications 54 can allow the voltage at the electrodes nodes 61a (E1'-E16') of one of the ASICs (60'; OUT1, OUT2) to be sent to the other ASIC (60; IN1, IN2) to be measured. Off-bus connections 54 are further useful in generation and distribution of a clock signal governing communications on the bus 90 as well as in the ASIC(s) 60. As these concepts are discussed in detail in the above-referenced ASIC Publications, they are not elaborated upon here.

FIG. 2B shows various functional circuit blocks within ASIC 60, which are briefly described. ASIC 60 includes an internal bus 92 which can couple to external bus 90 and which may duplicate bus 90's signals. Note that each of the functional blocks includes interface circuitry 88 enabling communication on the internal bus 92 and ultimately external bus 90, as the above-referenced ASIC Publications explain. Interface circuitry 88 includes circuitry to help each block recognize when bus 92 is communicating data with addresses belonging to that block. ASIC 60 contains several terminals 61 (e.g., pins, bond pads, solder bumps, etc.), such as those necessary to connect to the bus 90, the battery 14, the coils 34, 36, external memory (not shown). Terminals 61 include electrode node terminals 61a (E1'-E16') which connect to the electrodes 16 (E1-E16) on the lead(s) 18 by way of DC-blocking capacitors 55. As is known, DC-blocking capacitors 55 are useful to ensure that DC current isn't inadvertently (e.g., in the event of failure of the ASIC 60's circuitry) injected into the patient's tissue, and hence provide safety to the IPG 10. Such DC-blocking capacitors 55 can be located on or in the IPG 10's PCB 30 (FIG. 1C) inside of the IPG's case 12. See U.S. Patent Application Publication 2015/0157861.

Each of the circuit blocks in ASIC 60 performs various functions in IPG 10. Telemetry block 64 couples to the IPG telemetry coil 34, and includes transceiver circuitry for wirelessly communicating with an external controller according to a telemetry protocol. Such protocol may comprise Frequency Shift Keying (FSK), Amplitude Shift Keying (ASK), or various short-range RF standards such as those mentioned above. Charging/protection block 62 couples to the IPG charging coil 38, and contains circuitry for rectifying power wirelessly received from an external charger (not shown), and for charging the battery 14 in a controlled fashion.

Analog-to-Digital (A/D) block 66 digitizes various analog signals for interpretation by the IPG 10, such as the battery voltage Vbat or voltages appearing at the electrodes, and is coupled to an analog bus 67 containing such voltages. A/D block 66 may further receive signals from sample and hold block 68, which as the ASIC Publications explain can be used to measure such voltages, or differences between two voltages. For example, sample and hold circuitry 68 may receive voltages from two electrodes and provide a difference between them (see, e.g., VE1-VE2 in FIG. 3, discussed subsequently), which difference voltage may then be digitized at A/D block 66. Knowing the difference in voltage between two electrodes when they pass a constant current allows for a determination of the (tissue) resistance between them, which is useful for a variety of reasons.

Sample and hold block 68 may also be used to determine one or more voltage drops across the DAC circuitry 72 (see Vp and Vn in FIG. 3, explained subsequently) used to create the stimulation pulses. This is useful to setting the compliance voltage VH output by a compliance voltage generator block 76. Compliance voltage VH powers the DAC circuitry 72, and the measured voltage drops can be used to ensure that the compliance voltage VH produced is optimal for the stimulation current to be provided—i.e., VH is not too low to be unable to produce the current required for the stimulation, nor too high so as to waste power in the IPG 10. Measuring Vp and Vn to determine whether VH is too high or too low is particularly useful because the resistance Rt of the patient's tissue may not be known in advance, or may change over time. Thus, the voltage drop across the tissue, Vrt, may change as well, and monitoring Vp and Vn provides an indication of such changes, and hence whether VH should be adjusted. Compliance voltage generator block 76 includes circuitry for boosting a power supply voltage such as the battery voltage, Vbat, to a proper level for VH. Such circuitry (some of which may be located off chip) can include an inductor-based boost converter or a capacitor-based charge pump, which are described in detail in U.S. Patent Application Publication 2010/0211132.

Clock generation block 74 can be used to generate a clock for the ASIC 60 and for communication on the bus 92. Clock generation block 74 may receive an oscillating signal from an off-chip crystal oscillator 56, or may comprise other forms of clock circuitry located completely on chip, such as a ring oscillator. U.S. Patent Application Publication 2014/0266375 discloses another on-chip circuit that can be used to generate a clock signal on the ASIC 60.

Master/slave control block 86 can be used to inform the ASIC 60 whether it is to be used as a master ASIC or as a slave ASIC (e.g., 60'), which may be bond programmed at M/S terminal 61. For example, M/S terminal may be connected to a power supply voltage (e.g., Vbat) to inform ASIC 60 that it will operate as a master ASIC, or to ground to inform that it will operate as a slave, in which case certain function blacks will be disabled, as the ASIC Publications explain.

Interrupt controller block 80 receives various interrupts (e.g., INT1-INT4) from other circuit blocks, which because of their immediate importance are received independent of the bus 92 and its communication protocol. Interrupts may also be sent to the microcontroller 50 via the bus 90. Internal controller 82 in the ASIC 60 may receive indication of such interrupts, and act a controller for all other circuit blocks, to the extent microcontroller 50 (FIG. 2A) does not handle such interrupts through the external bus 90. Further, each of the functional circuit blocks contain set-up and status registers (not shown) written to by the controller 82 upon initialization to configure and enable each block. Each functional block can then write pertinent data at its status registers, which can in turn be read by the controller 82 via internal bus 92 as necessary, or by the microcontroller 50 via external bus 90. The functional circuit blocks can further include simple state machines to manage their operation, which state machines are enabled and modified via each block's set-up and status registers.

Nonvolatile memory (NOVO) block 78 caches any relevant data in the system (such as log data). Additional memory (not shown) can also be provided off-chip via a serial interface block 84.

ASIC 60 further includes a stimulation circuit block 70, which includes circuitry for receiving and storing stimulation parameters from the microcontroller 50 via buses 90 and 92. Stimulation parameters define the shape and timing of stimulation pulses to be formed at the electrodes, and can include parameters such as which electrodes E1-E16 will be active; whether those active electrodes are to act as anodes that source current to a patient's tissue, or cathodes that sink current from the tissue; and the amplitude (A), duration (D), and frequency (f) of the pulses. Amplitude may comprise a voltage or current amplitude. Such stimulation parameters may be stored in registers in the stimulation circuitry block 70. See, e.g., U.S. Patent Application Publications 2013/0289661; 2013/0184794.

Block 70 also includes a Digital-to-Analog Converter circuitry (DAC) 72 for receiving the stimulation parameters from the registers and for forming the prescribed pulses at the selected electrodes. FIG. 3 shows a simple example of DAC circuitry 72 as used to provide a current pulse between selected electrodes E1 and E2 and through a patient's tissue, Rt. DAC circuitry 72 as shown comprises two portions, denoted as PDAC 72p and NDAC 72n. These portions of DAC circuitry 72 are so named because of the polarity of the transistors used to build them and the polarity of the current they provide. Thus, PDAC 72p is formed from P-channel transistors and is used to source a current +I to the patient's tissue Rt via a selected electrode E1 operating as an anode.

NDAC 72*n* is formed of N-channel transistors and is used to sink current—I from the patient's tissue via a selected electrode E2. It is important that current sourced to the tissue at any given time equal that sunk from the tissue to prevent charge from building in the tissue, although more than one anode electrode and more than one cathode electrode may be operable at a given time.

PDAC 72*p* and NDAC 72*n* receive digital control signals from the registers in the stimulation circuitry block 70, denoted <Pstim> and <Nstim> respectively, to generate the prescribed pulses with the prescribed timing. In the example shown, PDAC 72*p* and NDAC 72*n* comprise current sources, and in particular include current-mirrored transistors for mirroring a reference current Iref to produce pulses with an amplitude (A) of I. PDAC 72*p* and NDAC 72*n* could however also comprise constant voltage sources. Control signals <Pstim> and <Nstim> also prescribe the timing of the pulses, including their duration (D) and frequency (f), as shown in the waveforms generated at the selected electrodes. The PDAC 72*p* and NDAC 72*n* along with the intervening tissue Rt complete a circuit between a power supply VH—the compliance voltage as already introduced—and ground. As noted earlier, the compliance voltage VH is adjustable to an optimal level at compliance voltage generator block 76 (FIG. 2B) to ensure that current pulses of a prescribed amplitude can be produced without unnecessarily wasting IPG power.

The DAC circuitry 72 (PDAC 72*p* and NDAC 72*n*) may be dedicated at each of the electrodes, and thus may be activated only when its associated electrode is selected as an anode or cathode. See, e.g., U.S. Pat. No. 6,181,969. Alternatively, one or more DACs (or one or more current sources within a DAC) may be distributed to a selected electrode by a switch matrix (not shown), in which case optional control signals <Psel> and <Nsel> would be used to control the switch matrix and establish the connection between the selected electrode and the PDAC 72*p* or NDAC 72*n*. See, e.g., U.S. Pat. No. 8,606,362. DAC circuitry 72 may also use a combination of these dedicated and distributed approaches. See, e.g., U.S. Pat. No. 8,620,436.

In the example waveform shown, the pulses provided at the electrodes are biphasic, meaning that each pulse comprises a first phase 94*a* of a first polarity, followed by a second phase 94*b* of an opposite polarity. This is useful as a means of active recovery of charge that may build up on the DC-blocking capacitors 55. Thus, while charge will build up on the capacitors 55 during the first pulse phase 94*a*, the second pulse phase 94*b* will actively recover that charge, particularly if the total amount of charge is equal in each phase (i.e., of the area under the first and second pulse phases are equal). Recovery of excess charge on the DC-blocking capacitors 55 is important to ensure that the DAC circuit 72 will operate as intended: if the charge/voltage across the DC-blocking capacitors 55 is not zero at the end of each pulse, it will skew formation of subsequent pulses, which may therefore not provide the prescribed amplitude.

While active recovery of charge using a biphasic pulse is beneficial, such active recovery may not be perfect, and hence some residual charge may remain on the DC-blocking capacitors 55 even after the second phase 94*b* of the biphasic pulse. Thus, the art has recognized the utility of passive charge recovery. Passive charge recovery is implemented with the stimulation circuit block 70, and includes use of passive recovery switches (transistors) 96, which are connected between the electrode nodes (E1'-E16') 61*a* and a common reference voltage. This voltage as shown may simply comprise the battery voltage, Vbat, but another reference voltage could also be used. Closing the passive recovery switches 96 during a time period 98 after the second pulse phase 94*b* couples the DC-blocking capacitors 55 in parallel between the reference voltage and the patient's tissue. Given the previous serial connection of the DC-blocking capacitors, this should normalize any remaining charge.

SUMMARY

A pulse generator is disclosed, which may comprise: a plurality of electrode nodes, each electrode node configured to be coupled to an electrode configured to contact a patient's tissue; a first digital-to-analog converter (DAC) configured to receive digital data specifying a magnitude of a total anodic current amplitude to be produced at the electrode nodes, and to produce a first current with a magnitude indicative of the total anodic current amplitude; a plurality of first calibration circuits each configured to receive the first current, wherein each of the first calibration circuits is controllable to produce a different second current as a function of the first current; and a plurality of second DACs each associated with one of the electrode nodes, wherein each second DAC is configured to receive one of the second currents, wherein each of the second DACs is configured when selected to amplify its received second current to produce an anodic stimulation current at its associated electrode node.

In one example, each of the first calibration circuits is controllable to produce its second current as a linear function of the first current. In one example, each of the first calibration circuits is controllable to provide a gain, an offset, or both to the first current when producing its second current. In one example, each of the first calibration circuits is independently controllable via unique first control signals received at each first calibration circuit to produce its second current. In one example, the first control signals received at each of the first calibration circuits prescribes a gain, an offset, or both that each first calibration circuit imparts to the first current when producing its second current. In one example, each of the first calibration circuits comprises a gain DAC configured to impart a gain to the first current when producing its second current. In one example, each of the first calibration circuits comprises an offset DAC configured to impart an offset to the first current when producing its second current. In one example, the first DAC is configured to receive a reference current, wherein the magnitude of first current comprises a scalar of the reference current. In one example, each of the first calibration circuits comprises an offset DAC configured to impart an offset to the first current when producing its second current, wherein each of the offset DACs is configured to receive the reference current, wherein the offset comprises a scalar of the reference current. In one example, each offset DAC comprises a positive offset DAC configured when selected to impart the offset as a positive offset to the first current when producing its second current, and a negative offset DAC configured when selected to impart the offset as a negative offset to the first current when producing its second current. In one example, each of the first calibration circuits comprises a gain DAC configured to impart a gain to the first current when producing its second current, and wherein each of the first calibration circuits comprises an offset DAC configured to impart an offset to the first current when producing its second current. In one example, a sum of the anodic stimulation currents at the electrode nodes equals the total anodic current amplitude.

In one example, the digital data further specifies a magnitude of a total cathodic current amplitude to be produced at the electrode nodes, wherein the first DAC is further configured to produce a third current with a magnitude indicative of the total cathodic current amplitude to be produced at the electrode nodes, wherein a polarity of the third current is opposite the first current, wherein the pulse generator further comprises: a plurality of second calibration circuits each configured to receive the third current, wherein each of the second calibration circuits is controllable to produce a different fourth current as a function of the third current; and a plurality of third DACs each associated with one of the electrode nodes, wherein each third DAC is configured to receive one of the fourth currents, wherein each of the third DACs is configured when selected to amplify its received fourth current to produce a cathodic stimulation current at its associated electrode node. In one example, each of the second calibration circuits is controllable to produce its fourth current as a linear function of the third current. In one example, each of the second calibration circuits is controllable to provide a gain, an offset, or both to the third current when producing its fourth current. In one example, each of the second calibration circuits is independently controllable via unique second control signals received at each second calibration circuit to produce its fourth current. In one example, the second control signals received at each of the second calibration circuits prescribes a gain, an offset, or both that each second calibration circuit imparts to the third current when producing its fourth current. In one example, each of the second calibration circuits comprises a gain DAC configured to impart a gain to the third current when producing its fourth current. In one example, each of the second calibration circuits comprises an offset DAC configured to impart an offset to the third current when producing its fourth current. In one example, the first DAC is configured to receive a reference current, wherein the magnitude of third current comprises a scalar of the reference current. In one example, each of the second calibration circuits comprises an offset DAC configured to impart an offset to the third current when producing its fourth current, wherein each of the offset DACs is configured to receive the reference current, wherein the offset comprises a scalar of the reference current. In one example, each offset DAC comprises a positive offset DAC configured when selected to impart the offset as a positive offset to the third current when producing its fourth current, and a negative offset DAC configured when selected to impart the offset as a negative offset to the third current when producing its fourth current. In one example, each of the second calibration circuits comprises a gain DAC configured to impart a gain to the third current when producing its fourth current, and wherein each of the second calibration circuits comprises an offset DAC configured to impart an offset to the third current when producing its fourth current. In one example, the magnitudes of the first and third currents are equal. In one example, a sum of the cathodic stimulation currents at the electrode nodes equals the total cathodic current amplitude. In one example, a magnitude of a sum of the anodic stimulation currents at the electrode nodes equals a magnitude of a sum of the cathodic stimulation currents at the electrode nodes.

A method is disclosed for operating a pulse generator having a plurality of electrode nodes, each electrode node configured to be coupled to an electrode configured to contact a patient's tissue. The method may comprise: receiving at the pulse generator digital data specifying a magnitude of a total anodic current amplitude to be produced at the electrode nodes; producing a first current with a magnitude indicative of the total anodic current amplitude; producing a plurality of different second currents from the first current, wherein each of the second currents is independently calibrated; receiving the independently-calibrated second currents at a plurality of second DACs, wherein each of the second DACs is associated with one of the electrode nodes; and selecting at least one second DAC to amplify its received second current to produce an anodic stimulation current at its associated electrode node.

A pulse generator is disclosed, which may comprise: a plurality of electrode nodes, each electrode node configured to be coupled to an electrode configured to contact a patient's tissue; a first digital-to-analog converter (DAC) configured to produce a first current, wherein the first DAC is configured to receive digital data specifying a total anodic current amplitude to be produced at the electrode nodes, a gain, and an offset, wherein the first current has a magnitude that is a function of the total anodic current amplitude, the gain, and the offset; a first distributor circuit configured to receive the first current, and to distribute the first current as a plurality of second currents; and a plurality of second DACs each associated with one of the electrode nodes, wherein each second DAC is configured to receive one of the second currents, wherein each of the second DACs is configured when selected to amplify its received second current to produce an anodic stimulation current at its associated electrode node.

In one example, the magnitude of the first current comprises a product of the total anodic current amplitude and the gain. In one example, the magnitude of the first current comprises the product increased or decreased by the offset. In one example, the first DAC is configured to receive a reference current, wherein the first current comprises the reference current scaled by the total anodic current amplitude and the gain. In one example, the scaled reference current is increased or decreased by the offset. In one example, the first DAC is controllable via the digital data to produce the first current as a linear function of the reference current. In one example, the first DAC comprises a first master DAC, a first global gain DAC, and a first global offset DAC. In one example, the first master DAC is configured to receive the total anodic current amplitude, wherein the first global gain DAC is configured to receive the gain, and wherein the first global offset DAC is configured to receive the offset. In one example, the first master DAC and the first global gain DAC are configured to produce a current indicative of a product of the total anodic current amplitude and the gain. In one example, the first global offset DAC is configured to produce a current indicative of the offset. In one example, the magnitude of the first current comprises the current indicative of the product of the total anodic current amplitude and the gain plus or minus the current indicative of the offset. In one example, the pulse generator further comprises a plurality of calibration circuits, wherein each of the calibration circuits is configured to adjust one of the second currents before each second DAC receives one of the second currents. In one example, a sum of the anodic stimulation currents at the electrode nodes equals the total anodic current amplitude. In one example, the total anodic stimulation current is limited to a range of currents in accordance with the gain and the offset. In one example, the range of currents comprises a minimum current and a maximum current. In one example, the digital data comprises an amplitude bus that specifies the total anodic current amplitude, and wherein the range of currents is producible for all possible values of the amplitude bus.

In one example, the digital data further specifies a total cathodic current amplitude to be produced at the electrode nodes, wherein the first DAC is further configured to produce a third current having a magnitude that is a function of the total cathodic current amplitude, the gain, and the offset, wherein a polarity of the third current is opposite the first current, wherein the pulse generator further comprises: a second distributor circuit configured to receive the third current, and to distribute the third current as a plurality of fourth currents; and a plurality of third DACs each associated with one of the electrode nodes, wherein each third DAC is configured to receive one of the fourth currents, wherein each of the third DACs is configured when selected to amplify its received fourth current to produce an cathodic stimulation current at its associated electrode node. In one example, the magnitude of the third current comprises a product of the total cathodic current amplitude and the gain, wherein the magnitude of the third current comprises the product increased or decreased by the offset. In one example, the first DAC is configured to receive a reference current, wherein the third current comprises the reference current scaled by the total cathodic current amplitude and the gain, wherein the scaled reference current is increased or decreased by the offset. In one example, the first DAC is controllable via the digital data to produce the third current as a linear function of the reference current. In one example, the first DAC comprises a second master DAC, a second global gain DAC, and a second global offset DAC. In one example, the second master DAC is configured to receive the total cathodic current amplitude, wherein the second global gain DAC is configured to receive the gain, and wherein the second global offset DAC is configured to receive the offset. In one example, the second master DAC and the second global gain DAC are configured to produce a current indicative of a product of the total cathodic current amplitude and the gain, and wherein the second global offset DAC is configured to produce a current indicative of the offset, wherein the magnitude of the third current comprises the current indicative of the product of the total cathodic current amplitude and the gain plus or minus the current indicative of the offset. In one example, the pulse generator further comprises a plurality of calibration circuits, wherein each of the calibration circuits is configured to adjust one of the fourth currents before each third DAC receives one of the fourth currents. In one example, a sum of the cathodic stimulation currents at the electrode nodes equals the total cathodic current amplitude. In one example, the total cathodic stimulation current is limited to a range of currents in accordance with the gain and the offset. In one example, the range of currents comprises a minimum current and a maximum current. In one example, the digital data comprises an amplitude bus that specifies the total cathodic current amplitude, and wherein the range of currents is producible for all possible values of the amplitude bus. In one example, the magnitudes of the first and third currents are equal. In one example, a sum of the cathodic stimulation currents at the electrode nodes equals the total cathodic current amplitude. In one example, a magnitude of a sum of the anodic stimulation currents at the electrode nodes equals a magnitude of a sum of the cathodic stimulation currents at the electrode nodes.

A method is disclosed for operating a pulse generator having a plurality of electrode nodes, each electrode node configured to be coupled to an electrode configured to contact a patient's tissue. The method may comprise: receiving at the pulse generator digital data specifying first digital data specifying a total anodic current amplitude to be produced at the electrode nodes, second digital data limiting the total anodic stimulation current to a range of currents, producing a first current in accordance with the first digital data and the second digital data; distributing the first current as a plurality of second currents; and receiving the second currents at a plurality of second DACs, wherein each of the second DACs is associated with one of the electrode nodes; and selecting at least one second DAC to amplify its received second current to produce an anodic stimulation current at its associated electrode node.

The method may further comprise independently calibrating each of the second current prior to receiving the second currents at the plurality of second DACs. In one example, the second digital data specifies a gain and an offset. In one example, the first current is produced with a magnitude that is a function of the total anodic current amplitude, the gain, and the offset.

BRIEF DESCRIPTION OF THE DRAWINGS

FIGS. 1A-1C show an Implantable Pulse Generator (IPG), and the manner in which an electrode array is coupled to the IPG, in accordance with the prior art.

FIGS. 7A and 7B respectively show the master DAC and distributor that provides the amplitude-scaled reference current to the PDACs and NDACs, while

FIG. 10D summarizes the control signals used by the calibration circuits, and the electrode gain and offset current values that they produce.

FIG. 10G shows an example of how the calibration algorithm can operate to optimize an electrode current.

FIG. 11E summarizes the control signals used by the global gain and offset circuitry in the current range DAC circuitry, and the global gain and offset current values that they produce.

FIG. 11F shows an example of how the global gain and offset circuitry can operate to set electrode currents within a desired therapeutic range.

FIG. 12C shows modification of the logic circuitry allowing it to be controlled by multiple resolution control signals.

FIG. 15A shows the high power domain (VH/Vssh) operable in the PDACs and the low power domain (Vcc/ground) operable in the NDACs, and shows how compliance voltage VH can be varied.

FIG. 15B shows generators used to produce Vssh and Vcc.

DETAILED DESCRIPTION

Figure 4A:
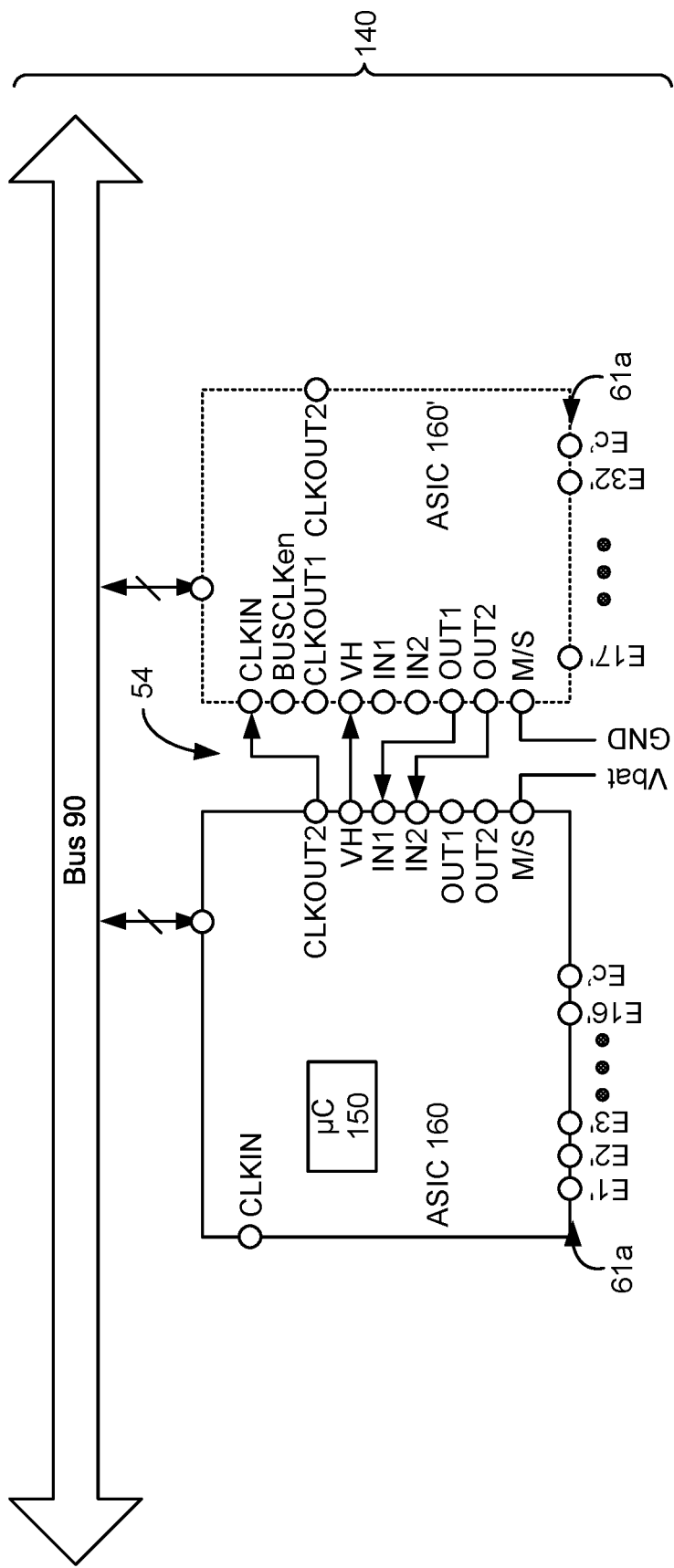
FIG. 4A shows an improved architecture for an IPG, in which an improved ASIC includes a microcontroller circuit block.
Figure 4B:
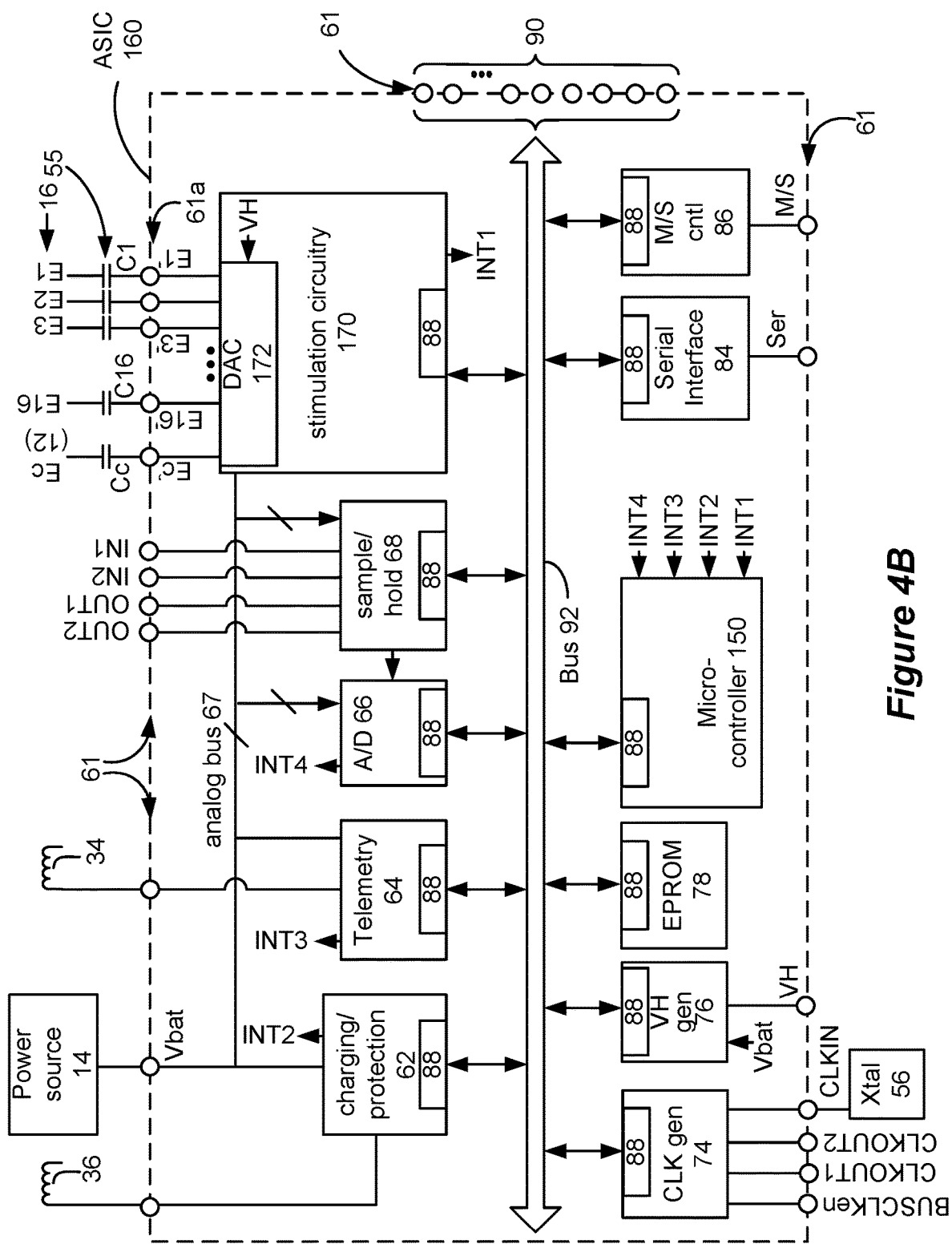
FIG. 4B shows circuitry blocks within the improved ASIC, including improved stimulation circuitry and its improved DAC circuitry.

FIGS. 4A and 4B show an improved architecture 140 and ASIC 160 for an IPG such as IPG 10 described earlier. Elements in architecture 140 and ASIC 160 that can remain unchanged from the prior art architecture 40 and ASIC 60 described in the Introduction bear the same elements numerals, and are not described again.

Figure 2A:
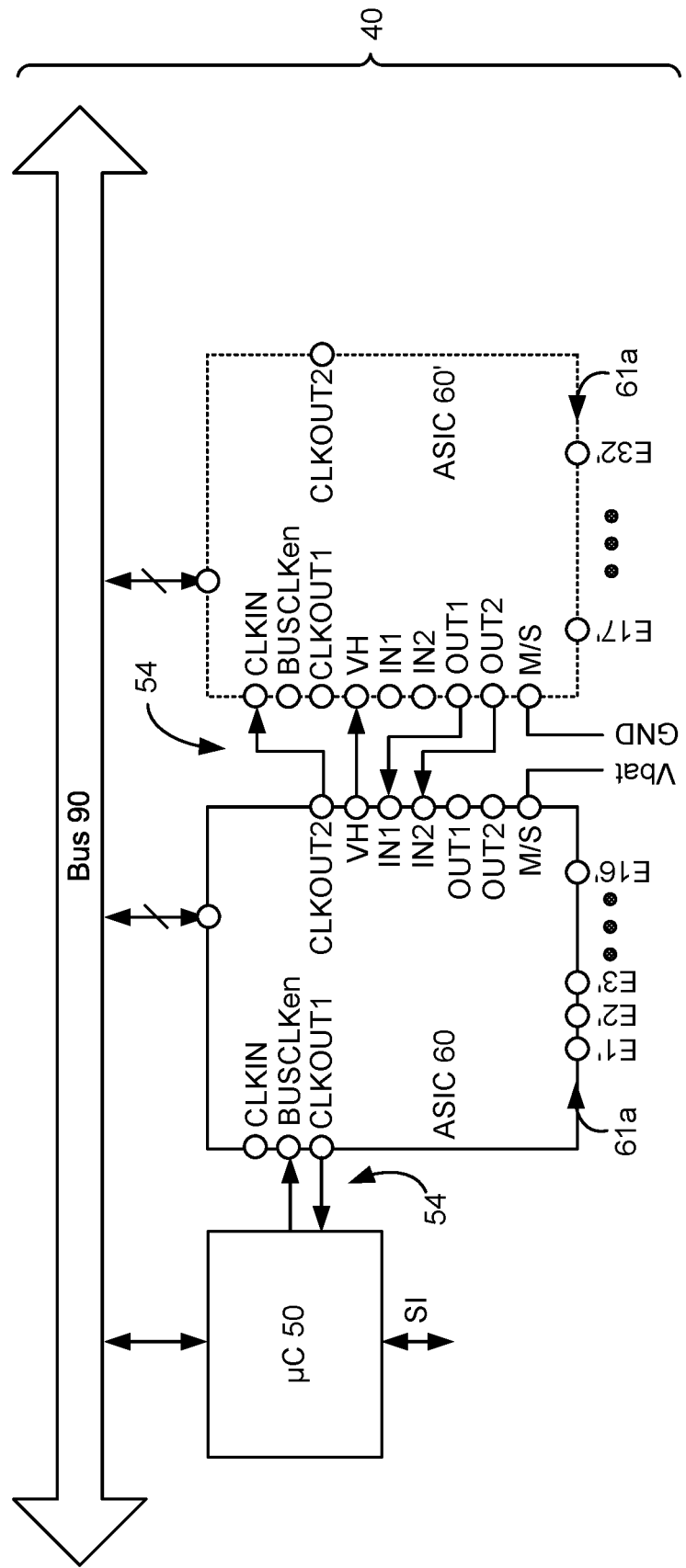
FIG. 2A shows an architecture for an IPG utilizing a microcontroller integrated circuit and an Application Specific Integrated Circuit (ASIC), in accordance with the prior art.
Figure 2B:
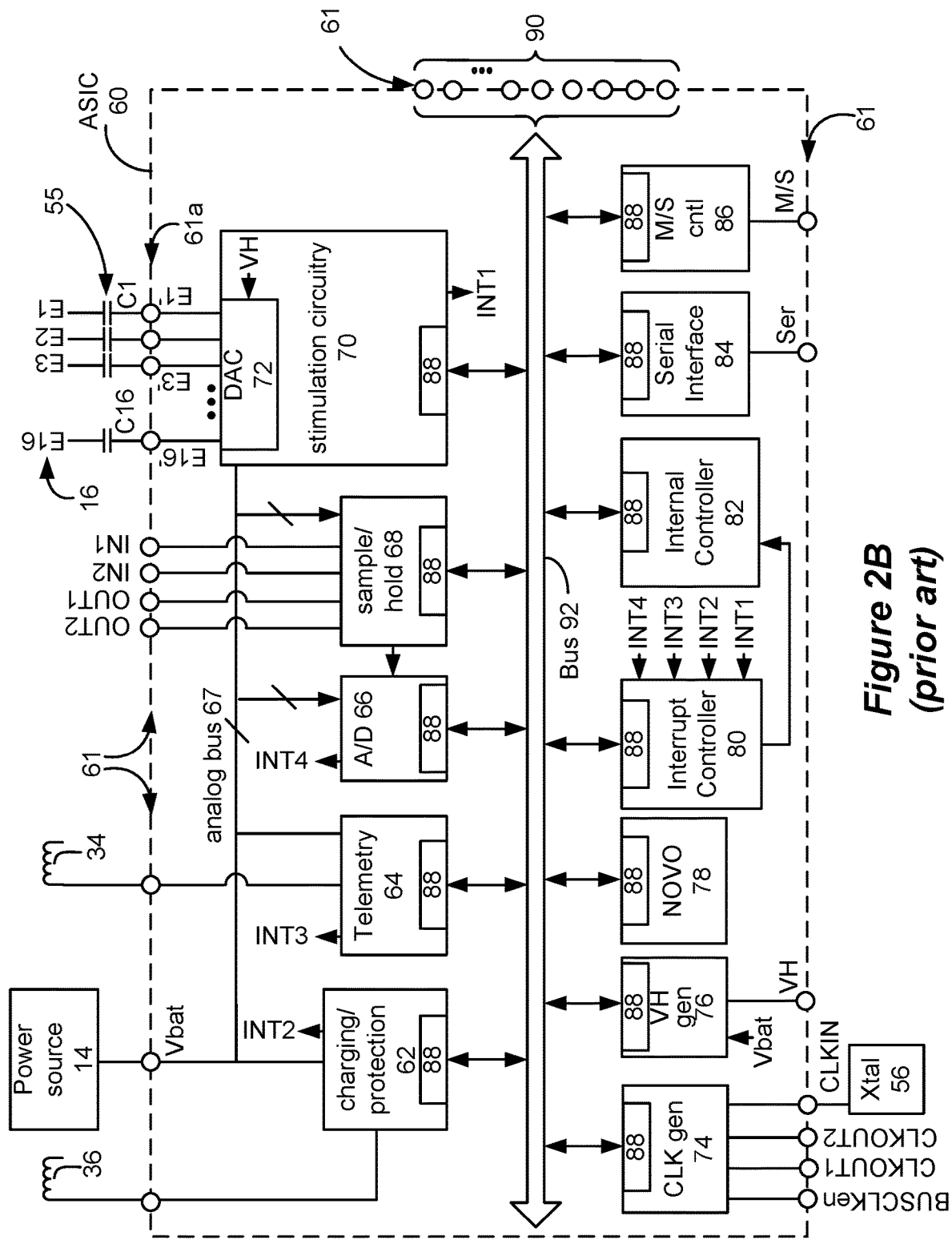
FIG. 2B shows circuitry blocks within the ASIC, and connection to off-chip components, in accordance with the prior art.

Improved ASIC 160 includes a microcontroller block 150 as part of its monolithic structure, which as shown in FIG. 4B can communicate with other functional blocks in the ASIC 160 via internal bus 92. Because ASIC 160 includes an internal microcontroller 150, an external microcontroller (e.g., 50, FIG. 2A) can be dispensed with in the improved architecture 140, simplifying IPG design and saving room within the interior of the case 12 and on the IPG's PCB 30 (FIG. 1C).

Microcontroller block 150 may receive interrupts independent of the bus 92 and its communication protocol, although interrupts may also be sent to the microcontroller 150 via the bus 92 as well. Even though ASIC 160 includes a microcontroller block 150, the ASIC 160 may still couple to an external bus 90, as shown in FIG. 4A. This can facilitate communications between the ASIC 160 and another device, such as a memory integrated circuit (not shown) or possibly another microcontroller device that might be coupled to the bus 90. Bus 90 can also facilitate communication between (master) ASIC 160 and another identically-constructed (slave) ASIC 160', shown in dotted lines in FIG. 4A. As described in the Introduction (FIG. 2A), use of an additional ASIC 160' allows the number of electrodes 16 the IPG 10 supports to be doubled, and many of the same off-bus connections 54 can be used as described earlier, and as described in the above-referenced ASIC Publications. In one example, the microcontroller block 150 can comprise circuitry from an ARM Cortex-M0+ Processor, which may be incorporated into the monolithic integrated circuit of the ASIC 160 by licensing various necessary circuits from the library that comprises that processor.

Figure 3:
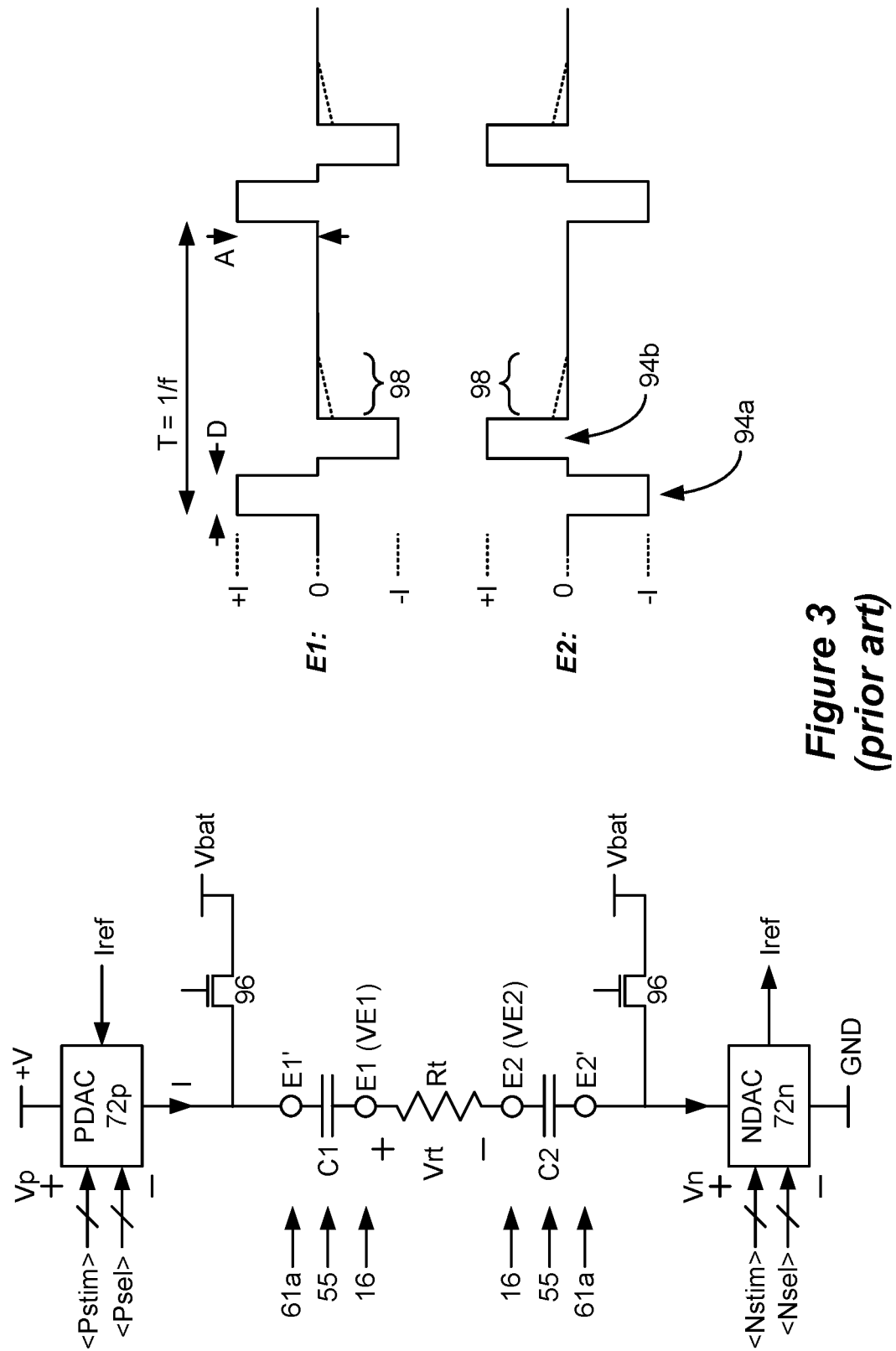
FIG. 3 shows aspects of the Digital-to-Analog converter (DAC) circuitry within the stimulation circuitry of the ASIC, and stimulation pulses formable thereby, in accordance with the prior art.
Figure 5:
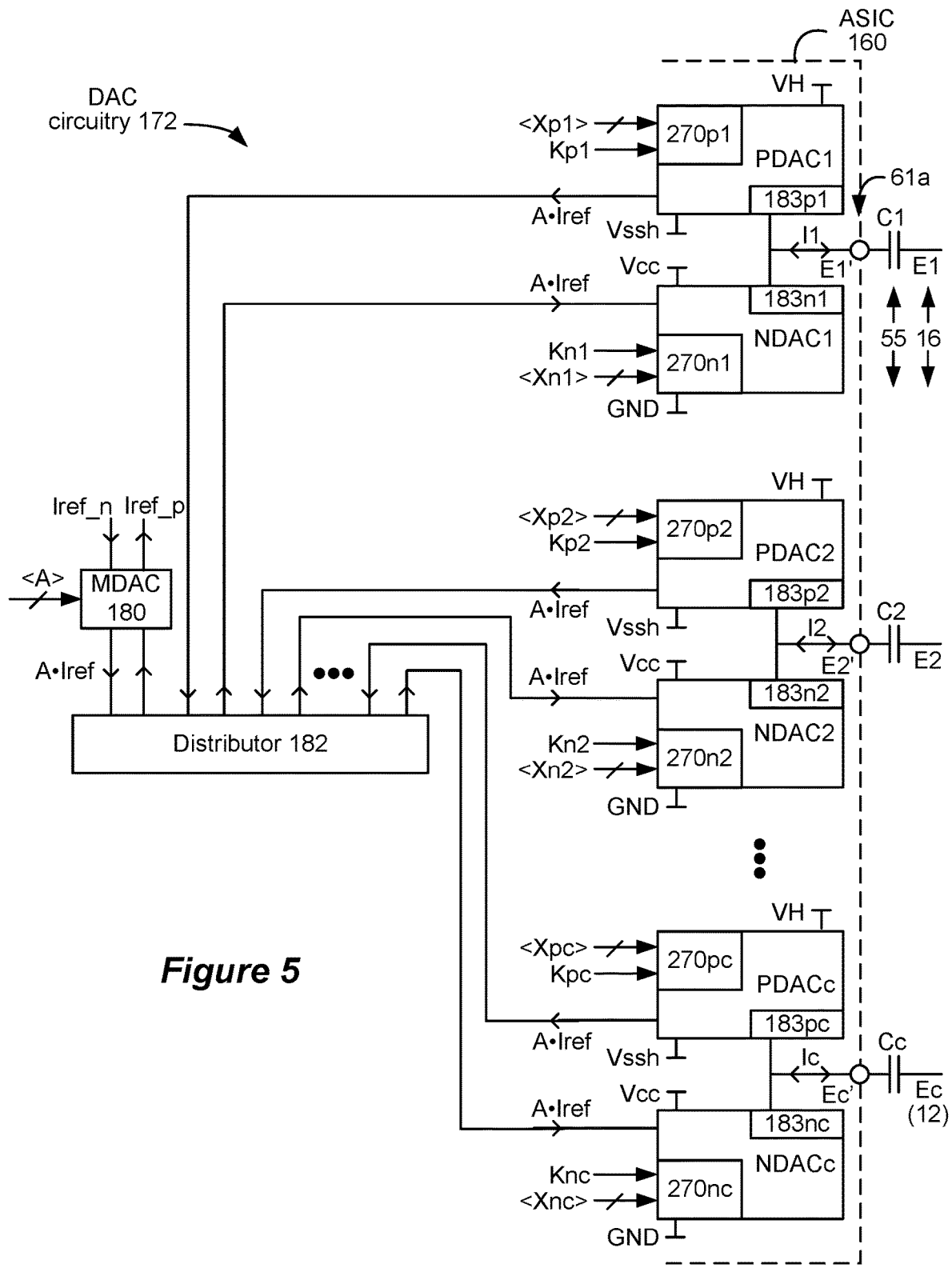
FIG. 5 shows the improved DAC circuitry, including a centralized master DAC to set the amplitude of stimulation via an amplitude bus, and a distributor for sending a reference current scaled by the amplitude to PDAC/NDAC pairs dedicated to each electrode.

FIGS. 5-13C describe details of improved stimulation circuitry 170, including improved DAC circuitry 172, within ASIC 160. FIG. 5 shows a first example of DAC circuitry 172, in which each electrode node 61a (Ei) has its own dedicated PDAC (PDACi) able when selected to source a current to that electrode node, and its own dedicated NDAC (NDACi) able to sink a current from that electrode node. In the example of FIG. 5 it is assumed that ASIC 160 supports seventeen electrodes 16, specifically electrodes E1-E16 plus a case electrode Ec comprising the IPG's conductive case 12 (FIG. 1A), which is useful to use as an electrode during monopolar stimulation. Thus, there are seventeen PDACs and seventeen NDACs. However, the number of supported electrodes can vary. Each PDACi/NDACi pair outputs its current from output stages 183$pi$ and 183$ni$ respectively, the outputs of which are connected together at each electrode node Ei' (61a) to form a current Ii, which will source a current when the PDACi is active and sink a current when the NDACi is active. Output stages 183 in each PDAC and NDAC can be considered part of those PDACs and NDACs. Each electrode node Ei' is then preferably connected off chip to a DC-blocking capacitor Ci (55), which are then in turn connected to the lead-based electrodes Ei (16), as explained earlier. DAC circuitry 172 can further include passive recovery switches connected to each electrode node Ei' (96, FIG. 3), as is explained in further detail in U.S. Patent Application Publication 2018/0071527, which is incorporated by reference in its entirety.

As explained further with reference to FIGS. 15A-16D, each of the PDACs, and the control signals they receive and process, operate in a high power domain defined by power supply voltages VH and Vssh. VH comprises the compliance voltage described earlier and acts as the upper power supply within the high power domain, while Vssh is lower than VH and acts as the lower power supply within the high power domain. By contrast, each of the NDACs, and the control signals they receive and process, operate in a low power domain defined by power supply voltages Vcc and ground (GND; 0 Volts). Vcc acts as the upper power supply within the low power domain, while GND is lower than Vcc and acts as the lower power supply within the low power domain. Both of power supplies VH and Vssh are preferably variable as explained later, but are preferably higher than power supplies Vcc and ground.

DAC circuitry 172 includes a master DAC (MDAC) 180 which communicates with all PDAC/NDAC pairs at each of the electrodes. Master DAC 180 receives an indication of the total anodic and total cathodic current amplitude 'A' of the stimulation pulses that the IPG will form at any given time, which indication is denoted by a bus of digital signals, <A>. The total anodic current sourced to the tissue should equal the total cathodic current sunk from the tissue at any point in time; otherwise an undesirable net charge would build in the patient's tissue. Thus, 'A' is the same for both total anodic current and total cathodic current.

Figure 6:
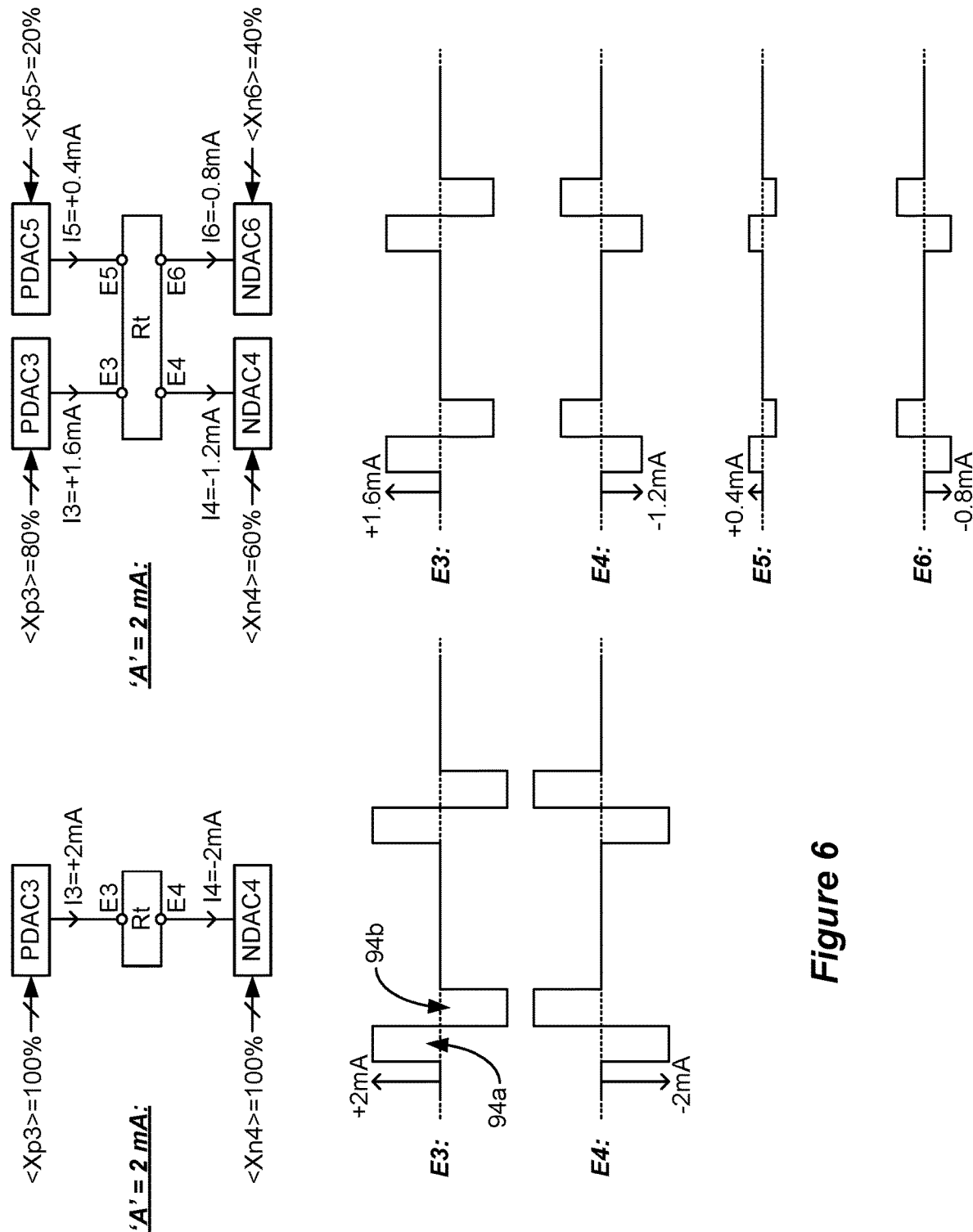
FIG. 6 shows the manner in which stimulation pulses can be formed at the electrodes based on the amplitude and based on percentage busses received by the PDACs and NDACs.

Total anodic and cathodic current 'A' is illustrated by the example pulses in FIG. 6. Two sets of pulses are illustrated, and in each case, 'A' as set by amplitude bus <A> is 2 mA. In the pulses at the left (and considering only the first pulse phases 94a of the biphasic pulses), only one anode electrode E3 has been specified, and only one cathode electrode E4 has been specified. Thus, PDAC3 simply sources +2 mA (the total anodic current) to its dedicated electrode E3 and to the patient's tissue Rt, and NDAC4 simply sinks −2 mA (the total cathodic current) from its dedicated electrode E4 and from the patient's tissue Rt. (During the second pulse phases 94b, this would essentially be reversed by activating the opposite polarity DAC at the selected electrodes, with NDAC3 sinking −2 mA from cathode electrode E3, and PDAC4 sourcing +2 mA to anode electrode E4).

In the pulses at the right of FIG. 6, two electrodes E3 and E5 have been selected as anode electrodes, and two electrodes E4 and E6 have been selected as cathode electrodes. Therefore, the two anode electrodes share the total anodic current of 'A'=2 mA, with PDAC3 sourcing +1.6 mA to electrode E3 and PDAC5 sourcing +0.4 mA to electrode E5. The two cathode electrodes share the total cathodic current of 'A'=2 mA, with NDAC4 sinking −1.2 mA from electrode E4 and PDAC6 sinking −0.8 mA from electrode E6. How the total anodic current and the total cathodic current 'A' is shared in DAC circuitry 172 between the selected anode and cathode electrodes is explained subsequently.

Returning to FIG. 5, master DAC 180 in this example receives two reference currents, Iref_n and Iref_p of different polarities. This detail is explained later, but Iref_n and Iref_p are of essentially the same small magnitude, e.g., 100 nA, and both may therefore be simply referred to as Iref. The master DAC 180 amplifies the reference current by 'A' as specified by the amplitude bus <A>, and so outputs A*Iref. In the example shown, master DAC 180 outputs A*Iref with different polarities, again as explained later. In one example, <A> can comprise 8 bits, and thus master DAC 180 can output currents in 256 increments of Iref, i.e., 0, Iref, 2Iref, 3Iref, . . . , 255Iref, or 0.0 nA, 100 nA, 200 nA, 300 nA, . . . , 25.5 µA. The number of bits within amplitude bus <A> and hence the corresponding number of increments master DAC 180 can output are variable. A*Iref is further amplified at the PDACs or NDACs before being output to the electrode nodes 61a, as explained subsequently.

Master DAC 180 provides A*Iref to distributor circuitry 182, whose function is to generate and distribute A*Iref to each PDAC and NDAC with the correct polarity. More specifically, and as the arrows in FIG. 5 show, distributor 182 pulls A*Iref from the PDACs and pushes A*Iref to the NDACs.

Figure 7A:
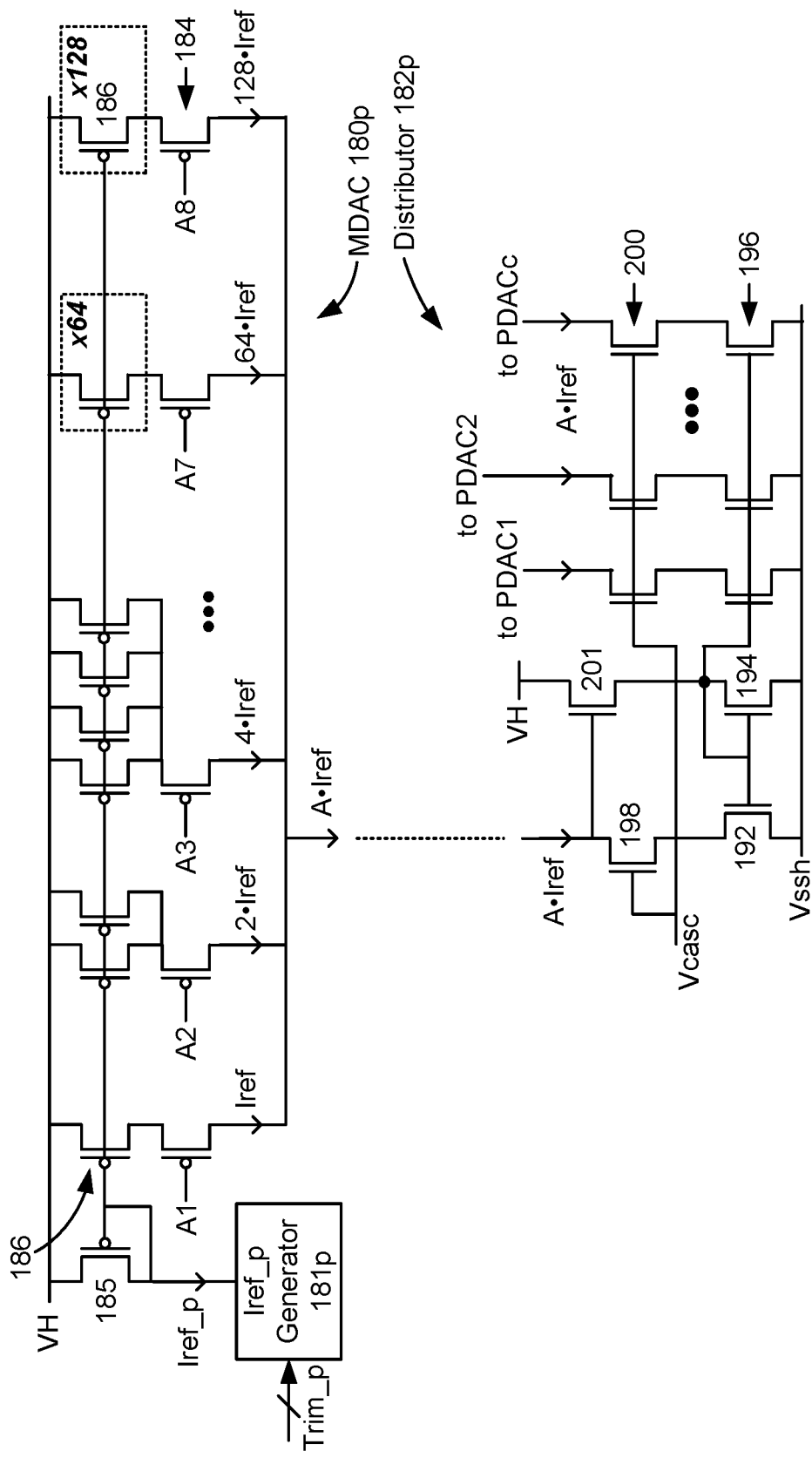
Figure 7B:
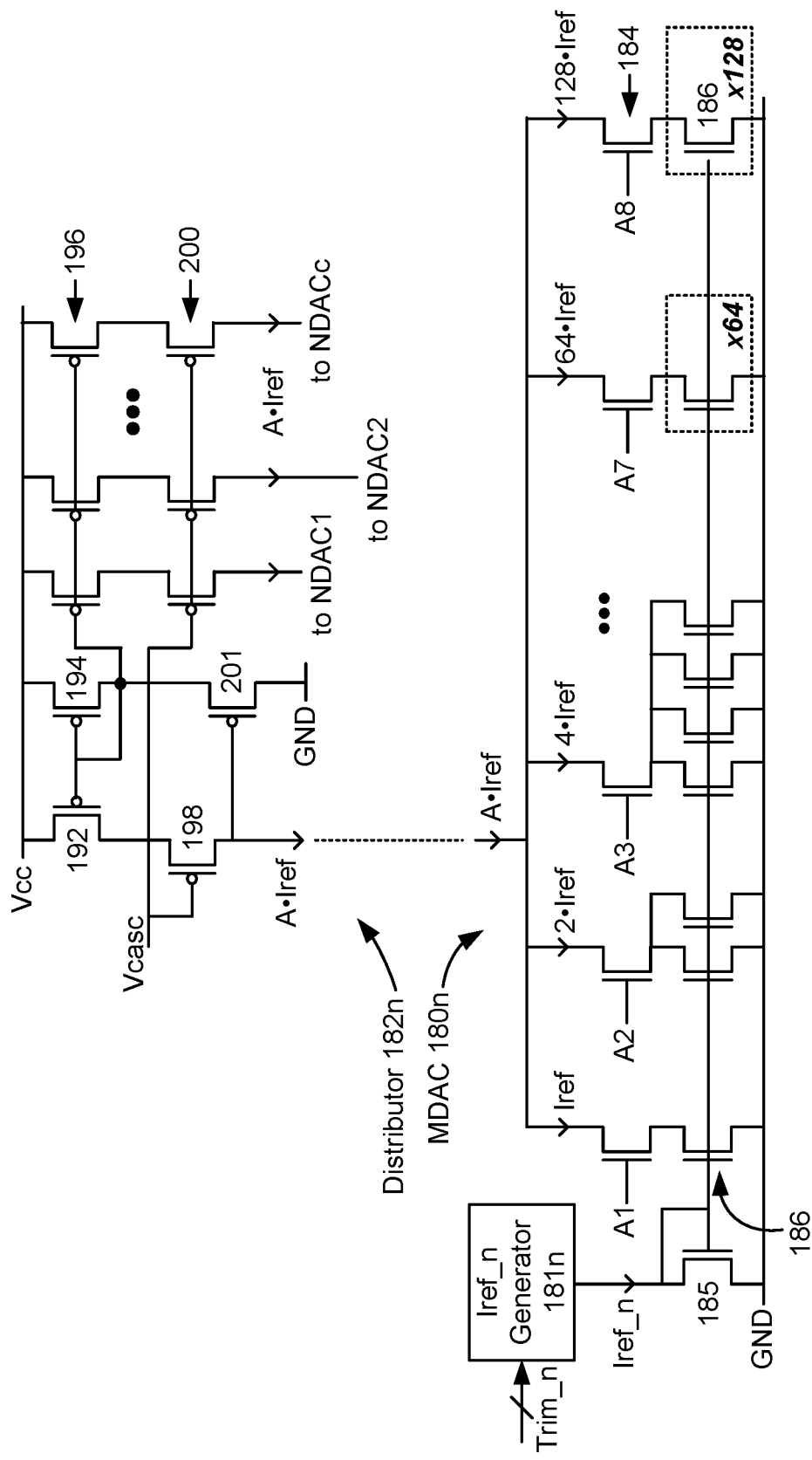

FIGS. 7A and 7B show details of the master DAC 180 and distributor 182. In the illustrated example, the master DAC 180 comprises two sections 180p (FIG. 7A) and 180n (FIG. 7B). The distributor 182 also comprises two sections 182p (FIG. 7A) and 182n (FIG. 7B). Master DAC 180p and distributor 182p work together (FIG. 7A) to pull A*Iref from the PDACs, while master DAC 180n and distributor 182n work together (FIG. 7B) to push A*Iref to the NDACs.

As a comparison of FIGS. 7A and 7B shows, the circuitry 180p/182p and the circuitry of 180n/182n are symmetric, although 180p/182p are powered in the high power domain (VH/Vssh), while 180n/182n are powered in the low power domain (Vcc/GND). Further, the polarity of the transistors in 180p/182p and 180n/182n are different, with P-channel transistors proximate to the higher power supply in each power domain (VH and Vcc), and with N-channel transistors proximate to the lower power supply in each power domain (Vssh and GND). Nonetheless, the combination of 180p/182p in FIG. 7A essentially operates the same as does the combination of 180n/182n in FIG. 7B, except that logic state of control signals (e.g., <A>) would be inverted in each (not shown). Thus, similar elements numerals are provided for the transistors in these figures, and both are discussed for simplicity primarily with reference to FIG. 7B.

FIG. 7B shows master DAC 180n, which is controlled directly by the eight control signals A8:1 in amplitude bus <A>. Each of these control signals is input to a selection transistor 184, each of which is in series with a differing number of transistors 186 connected in parallel. Reference current Iref_n is produced by a generator 181n, and is provided to a transistor 185, which mirrors its current to each of the transistors 186. (Such mirroring occurs because the gates of transistor 185 and transistors 186 are connected to transistor 185's drain, as is well known). The number of parallelled transistors 186 varies in binary fashion, such that A1 controls connection of one transistor 186; A2 controls connection of two transistors 186; A3 controls connection of four transistors 186, and so on, with A8 controlling connection of 128 transistors 186. Because selection transistors 184 are N-channel transistors, they are active high (they would be active low in master DAC 180p in FIG. 7A). Therefore, for example, if the amplitude bus signals <A>='00010101', i.e., the number 21 in binary, control signals A5, A3, and A1 are asserted, and (16+4+1)*Iref will be mirrored and summed at the output of the master DAC 180 for a total current 21Iref. In actuality, it is Iref_n that is mirrored, but again this can be referred to as Iref for simplicity.

Master DAC 180n pulls output A*Iref from distributor 182n, which in turn pushes A*Iref out to each NDAC. Specifically, A*Iref is mirrored into a series of branches each comprising a transistor 196 and a transistor 200 in series, with each branch pushing A*Iref to its dedicated NDAC. Distributor 182n is designed to achieve good linearity throughout the entire range with which A*Iref can vary (again, e.g., from 0 to 25.5 µA). Transistor 192 and transistors 196 form current mirrors, and are of the same size. Cascode transistors 198 and 200 are controlled by voltage Vcasc, and transistors 192, 194, 198, and 201 form a feedback loop.

The master DAC 180p of FIG. 7A operates similarly to push A*Iref to its distributor 182p, which in turn operates similarly to pull A*Iref from each of the PDACs. Notice that master DAC 180p includes its own generator 181p to generate its own reference current, Iref_p. Both the Iref_p generator 181p (FIG. 7A) and the Iref_n generator 181n (FIG. 7B) receive control signals Trim_p and Trim_n, which allow the magnitude of Iref_p and Iref_n to be adjusted. As stated earlier, Iref_p and Iref_n are essentially the same magnitude (100 nA). However, it is preferred to have the flexibility to adjust these magnitudes slightly via Trim_p and Trim_n to ensure that the amplified outputs A*Iref of the combinations 180p/182p and 180n/182n are equal; they might not be given non-idealities inherent in ASIC 160 fabrication. While reference current generation could be adjusted at any time, it is preferred to adjust Iref_p and Iref_n during manufacturing. For example, A*Iref can be measured during manufacturing from the master DAC 180p and the master DAC 180n, and Trim_p and Trim_n can be adjusted until the magnitude of A*Iref from each is equal. Thereafter, Trim_p and Trim_n can be stored in a non-volatile registers (not shown) so that generators 181p and 181n can output Iref_p and Iref_n with appropriate magnitudes.

Figure 7C:
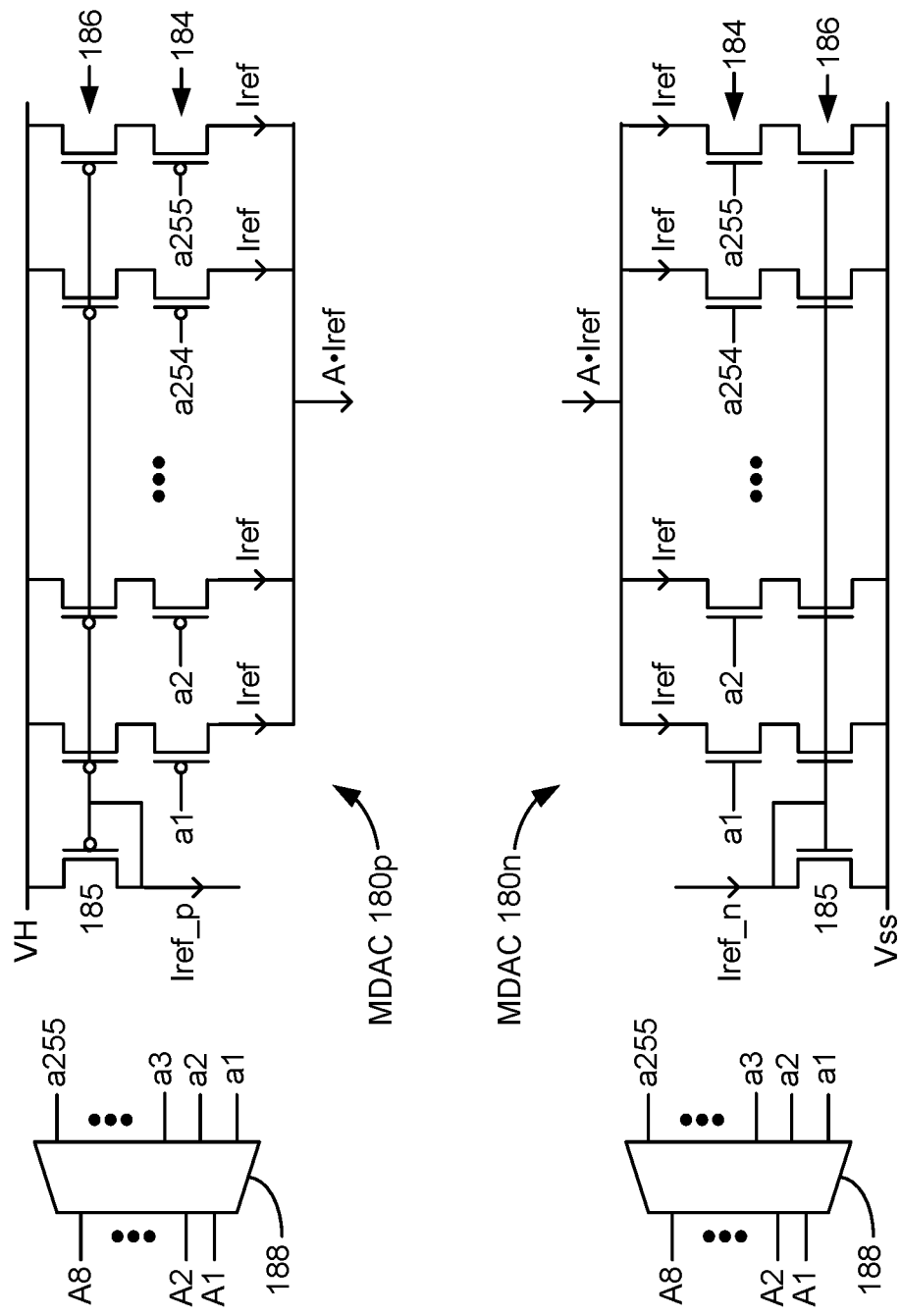
FIG. 7C shows an alternative design for the master DACs.

FIG. 7C shows alternative circuitry for master DACs 180p and 180n. These examples include logic circuitry 188, which convert the eight <A> bits into 256 different control signals a0 to a255. Logic circuitry 188 is sometimes known as a "thermometer decoder," which will assert a number of outputs equal to the input value 'A.' Assuming again that the amplitude bus signals <A>='00010101' (21), control signals a21:1 will be asserted, with all other control signals a255:22 remaining unasserted. Control signals a255:1 are each sent to a selection transistor 184, each of which is in series with only a single current mirror transistor 186. The assertion of each control signal 'a' therefore mirrors and sums an increment of Iref at the output of the master DAC 180p and 180n, and so the assertion of a21:1 again renders 21Iref at the output.

The master DAC 180 and distributor 182 will be located at a discrete location on the ASIC 160. By contrast, each of the PDAC/NDAC pairs will be at different locations on the ASIC 160, such as generally proximate to the ASIC chip's bond pads (61) connected to electrode nodes Ei' 61a. This means the distance between the master DAC 180/distributor 182 and each PDAC/NDAC pair will vary. Nonetheless, because each PDAC and NDAC is current controlled (rather than voltage controlled)—i.e., controlled by A*Iref—such differences in distance are mitigated. Were the PDACs and NDACs voltage controlled, with the master DAC 180 or distributor 182 outputting A*Vref for example, the different distances would work different voltage drops across the conductive traces connecting the distributor 182 to each of the PDACs and NDACs. These differing voltage drops would mean that each PDAC and NDAC would not receive exactly A*Iref, which would affect the accuracy of the amplitudes of the currents output by each PDAC and NDAC. Because the PDACs and NDACs are current controlled by A*Iref, such different transmission distances and voltage drops are of significantly lesser concern. Instead, each PDAC and NDAC will receive exactly A*Iref, allowing the PDACs and NDACs to output currents with proper amplitudes that do not vary as a function of their distance to the master DAC 180/distributor 182. Such current control of the PDACs and NDACs eases layout of the DAC circuitry 172 on the ASIC 160.

Referring again to FIG. 5, percentage busses, <X>, are shown, which are useful to allocating or "steering" of current between the electrodes, as explained further below. Each PDAC and NDAC receives its own percentage bus: thus, PDAC1 receives <Xp1>, NDAC1 receives <Xn1>, PDAC2 receives <Xp2>, NDAC2 receives <Xn2>, etc. As will be explained further below, the percentage busses <Xpi> specify a percentage (from 0-100%) of the total anodic current 'A' that each PDACi must source to its associated electrode node Ei'. Percentage busses <Xni> specify a percentage of the total cathodic current 'A' that each NDACi must sink from its associated electrode node Ei'. In effect, the various percentage busses <X> explain how the total anodic current and total cathodic current 'A' are shared between electrodes.

This is explained further with reference to the pulses shown in FIG. 6. As described earlier, amplitude 'A' is set by amplitude bus <A> to 2 mA in each example. For the pulses at the left, where electrode E3 is selected as the only anode and electrode E4 as the only cathode, these electrodes will receive 'X'=100% of the total anodic and total cathodic current respectively. Therefore, percentage bus <Xp3> will indicate 100% to PDAC3 associated with electrode E3, and percentage bus <Xn4> will indicate 100% to NDAC4 associated with electrode E3.

For the pulses at the right, having a plurality of anode and cathode electrodes, the percentage busses indicates the percentage of the total anodic or cathodic current 'A'=2 mA that the associated PDAC or NDAC should output. Therefore, to form a pulse with an amplitude of +1.6 mA at anode electrode E3, percentage bus <Xp3> will indicate 80% to PDAC3, which will in turn source a current of 80% of 2.0 mA, or +1.6 mA, at E3. Percentage bus <Xp5> is set to 20%, meaning the remaining anodic current (20% of 2 mA, or +0.4 mA) is sourced from PDAC5 to anode electrode E5. Similarly, to form pulses of −1.2 mA and −0.8 mA at the cathode electrodes E4 and E6, the total cathodic current 'A'=2.0 mA is shared 60% and 40%, and so <Xn4>=60% is sent to NDAC4, and <Xn6>=40% is sent to NDAC6. In effect, percentage bus signals <Xpi> are used to select one or more electrodes as anodes and to specify the percentage relative to 'A' each must source, while percentage bus signals <Xni> are used to select one or more electrodes as cathodes and to specify the percentage relative to 'A' each must sink.

Returning to FIG. 5, resolution control signals, K, are shown. Each PDAC and NDAC preferably receives its own resolution control signal: thus, PDAC1 receives Kp1, NDAC1 receives Kn1, PDAC2 receives Kp2, NDAC2 receives Kn2, etc. As will be explained further below, the resolution control signals specify an amount by which each PDAC or NDAC's percentage (X) can be adjusted. By way of preview, and in just one example, a resolution control signal K will dictate whether the percentage 'X' of its associated PDAC or NDAC (and hence the current it outputs to its electrode node 61a) will be variable in 1% increments in a high resolution mode (i.e., 'X'=1%, 2%, 3%, etc.) or in 4% increments in a low resolution mode (i.e., 'X'=4%, 8%, 12%, etc.).

Figure 8A:
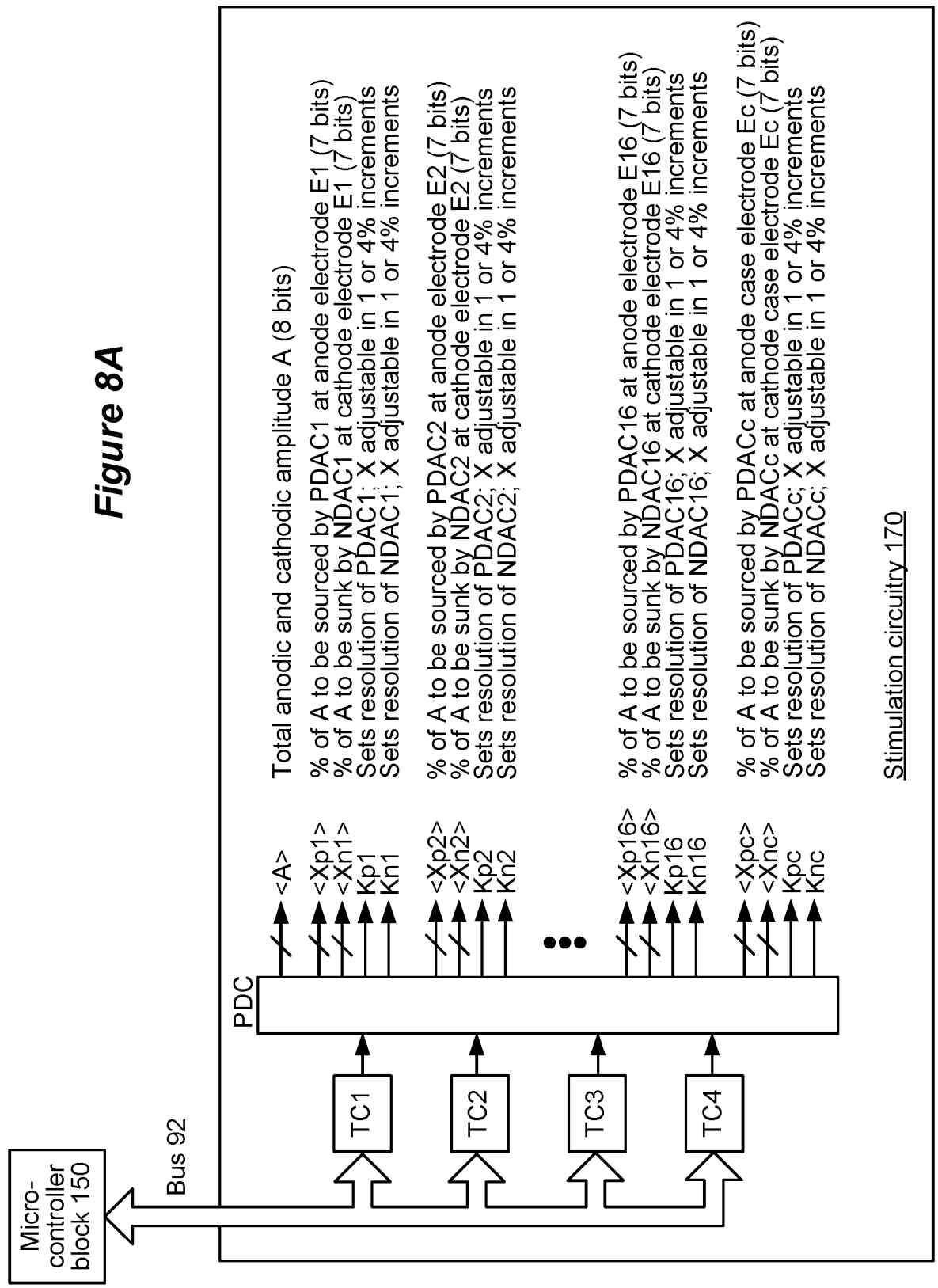
FIG. 8A shows a Pulse Definition Circuit (PDC) for providing the amplitude bus to the master DAC, and for providing the percentage busses and high/low resolution control signals to the PDACs and NDACs, which PDC receives information from different timing channels.
Figure 8B:
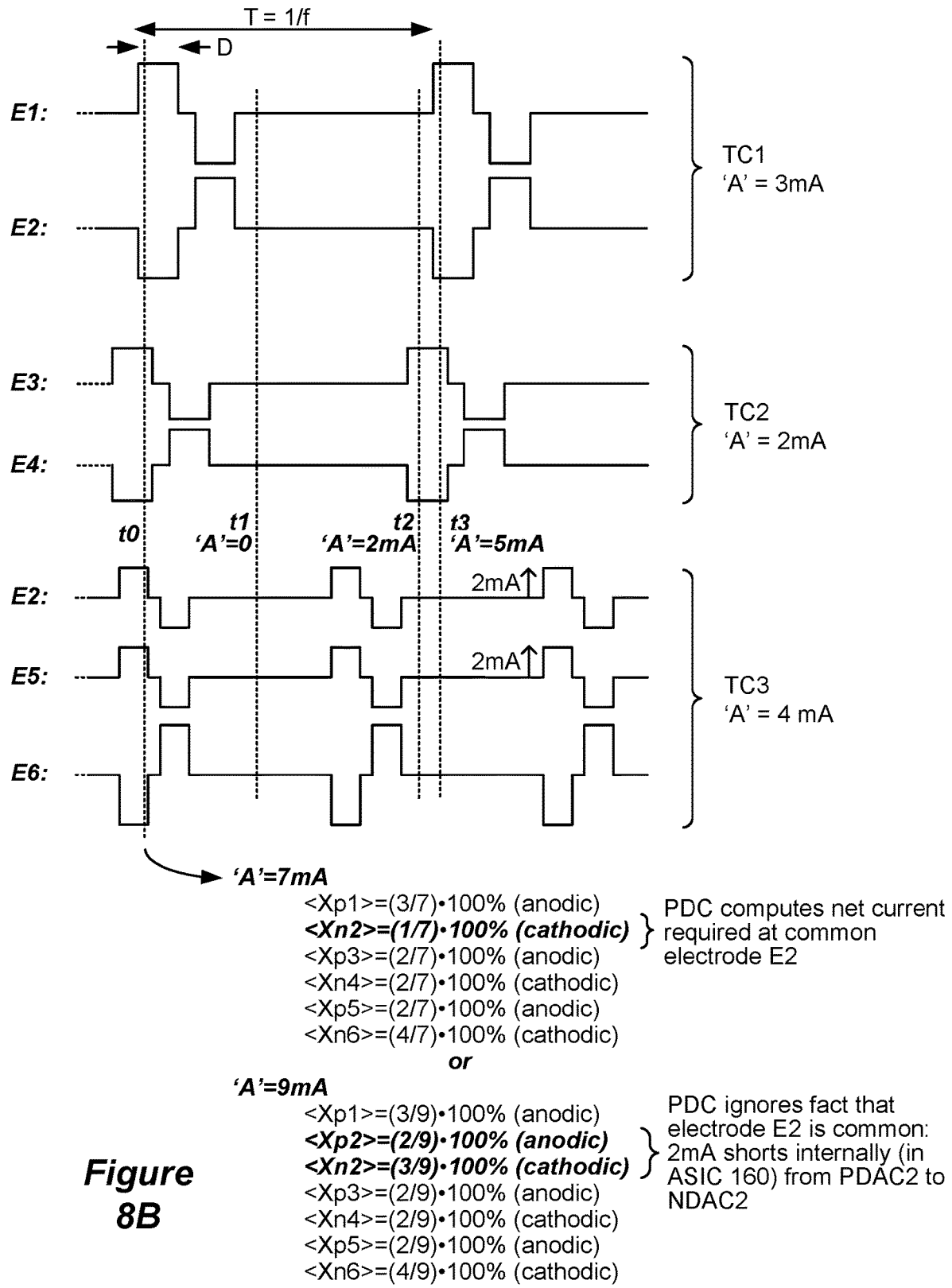
FIG. 8B shows how the PDC can control stimulation occurring on multiple timing channels.

FIG. 8A shows a Pulse Definition Circuit (PDCs) within stimulation circuitry 170 that outputs control signals <A>, <Xpi>, <Xni>, Kpi and Kni as already introduced. PDC, via these control signals, dictates the stimulation that will be issued by the DAC circuitry 172 at any given point in time. Providing data to the PDC are various timing channels (TC), four of which are shown, although different numbers could be used. A timing channel, as is well known, comprise a means for defining stimulation, and may run concurrently with stimulation defined and provided in a different timing channel. FIG. 8B shows examples of different stimulation pulses that may concurrently run in timing channels TC1-TC3. Each timing channel contains registers populated with data by microcontroller block 150 via bus 92 in accordance with a specified stimulation program to be run in that timing channel.

The PDC operates to assert control signals to form pulses specified in the timing channels TC1-TC3, and may additionally take various actions to resolve conflicts where pulses in the various timing channels overlap in time, as discussed further below. PDC may set amplitude bus <A> to 'A'=0 at times when no stimulation is to be provided by any timing channel, such as at time t1, and all <Xpi> and <Xni> may be set to 0 at these times as well.

At time t2, only the pulses in TC2 are issued. Hence PDC will set <A> in accordance with the total anodic and cathode amplitude required by that timing channel, i.e., 'A'=2 mA, and will additionally assert percentage bus control signals for PDAC3 (<Xp3>=100%>) and NDAC 4 (<Xn4>=100%) to form the specified anodic and cathodic current at electrodes E3 and E4 respectively. Notice that the duration (D) and frequency of the pulses is generally set by the PDC by issuing the percentages busses and amplitudes at appropriate times.

At time t3, the pulses in TC1 and TC2 overlap. Hence PDC in this example will need to provide a total anodic and cathodic amplitude sufficient to form the pulses in both timing channels. Because the pulses in TC1 require 3 mA and the pulses in TC2 require 2 mA, this totals 5 mA. However, the pulses in neither of these timing channels require the total 5 mA amplitude, meaning that the PDC must also adjust the percentage busses to ensure that pulses of proper amplitudes are formed. In other words, the PDC may adjust the percentage busses <Xi> from what they might otherwise be absent the overlap. Thus, because the pulses in TC1 require an amplitude of 3 mA, and because the total current required at time t3 is 5 mA in all timing channels, PDC will provide percentage bus signals to PDAC and NDAC circuitry involved in TC1 of 60% (i.e., 3 mA/5 mA). In other words, <Xp1> signals for PDAC1 at electrode E1 equal 60%, and <Xn2> signals for NDAC2 at electrode E2 equal 60%. Similarly, PDC will provide percentage bus signals to PDAC and NDAC circuitry involved in TC2 of 40% (i.e., 2 mA/5 mA). In other words, <Xp3> signals for PDAC3 at electrode E3 equal 40%, and <Xn4> signals for NDAC4 at electrode E4 equal 60%.

The PDC may also address the possibility that a common electrode may be activated by more than one timing channel at a time. Time t0 illustrates such a conflict: as well as the pulses in timing channels overlapping at time t0, electrode E2 is active in both of timing channels TC1 and TC3. Further, notice that electrode E2 is simultaneously specified as a cathode (−3 mA) in TC1 and as an anode (+2 mA) in TC3.

PDC may take different actions when such a conflict arises. PDC may, for example, simply apply arbitration rules to prevent the pulses in the timing channels from overlapping in time, for example, by issuing the pulses in TC2; then after the pulses in TC2 have finished, issuing the pulses in TC3; and then after the pulses in TC3 have finished, issuing the pulses in TC1. Such arbitration would resolve the conflict of E2 having to act as a cathode and anode simultaneously. See, e.g., U.S. Patent Application Publication 2013/0184794 (discussing arbitration of stimulation pulses in different timing channels).

Alternatively, the PDC may sum the required current at common electrode E2 to determine the net current required at that electrode at that time, and set <A> and the percentage busses as necessary to form all specified pulses in the timing channels. For example, at time to, PDC may cause the current at E2 to equal −3 mA+2 mA=−1 mA. The currents required at the other electrodes at time t0 are E1=+3 mA, E3=+2 mA, E4=−2 mA, E5=+2 mA, and E6=−4 mA. Thus, the total anodic and cathodic current required at t0 (when E2=−1 mA is included) is 'A'=7 mA, so PDC will set the amplitude bus <A> to this value.

PDC may then adjust the percentage busses in accordance with this summed amplitude from the various timing channels. For example, because 'A' is set to 7 mA, PDAC1 of electrode E1 will be set to <Xp1>=(3/7)*100%, or approximately 43% of the total anodic current, to create the specified +3 mA pulse at electrode E1 in TC1. PDC already determined that common electrode E2 should receive −1 mA by summing at time t0, and so NDAC2 at electrode E2 will be set to <Xn2>=(1/7)*100%, or approximately 14% of the total cathodic current. PDAC3 of electrode E3 will be set to <Xp3>=(2/7)*100%, or approximately 29% of the total anodic current; NDAC4 of electrode E4 will be set to <Xn4>=(2/7)*100%, or approximately 29% of the total cathodic current; PDAC5 of electrode E5 will be set to <Xp5>=(2/7)*100%, or approximately 29% of the total anodic current; and NDAC6 of electrode E6 will be set to <Xn6>=(4/7)*100%, or approximately 59% of the total cathodic current. Note that despite these adjustments, PDC via <Xpi> and <Xni> will cause 100% of the total anodic and cathodic current 'A'=7 mA to issue at time t0.

PDC may also be configured to not sum the required current at common electrode E2, essentially ignoring the conflict that exists at this common electrode. Thus, PDC at time t0 may simply allow NDAC2 to issue −3 mA as required by TC1; and allow PDAC2 to issue +2 mA as required by TC3. Note that this is wasteful of IPG 10 power and its battery 14, because 2 mA of current would be shorted internally from PDAC2 to NDAC2 within the ASIC 160 to no useful effect; the remaining −1 mA would be sunk from NDAC2 from the tissue. Still, because such common-electrode conflicts should be relatively rare in time, such inefficiency can be tolerable. Should the PDC address conflicts in this manner, it would mean that the total anodic and cathodic current required at t0 is 'A'=9 mA, so PDC will set the amplitude bus <A> to this value.

Again, PDC will adjust the percentage bus signals accordingly. This is shown at the bottom of FIG. 8B. Specifically, PDAC1 of electrode E1 will be set to <Xp1>=(3/9)*100%, or approximately 33% of the total anodic current; PDAC2 of electrode E2 will be set to <Xp2>=(2/9)*100%, or approximately 22% of the total anodic current; NDAC2 of electrode E2 will be set to <Xn2>=(3/9)*100%, or approximately 33% of the total cathodic current; PDAC3 of electrode E3 will be set to <Xp3>=(2/9)*100%, or approximately 22% of the total anodic current; NDAC4 of electrode E4 will be set to <Xp4>=(2/9)*100%, or approximately 22% of the total cathodic current; PDAC5 of electrode E5 will be set to <Xp5>=(2/9)*100%, or approximately 22% of the total anodic current; and NDAC6 of electrode E6 will be set to <Xn6>=(4/9)*100%, or approximately 44% of the total cathodic current. Again in this example, PDC will cause 100% of the total anodic and cathodic current 'A'=9 mA to issue at time t0.

Details concerning software and hardware used to populate a PDC are disclosed in detail in U.S. Patent Application Publication 2018/0071513, which is incorporated by reference in its entirety.

Figure 9A:
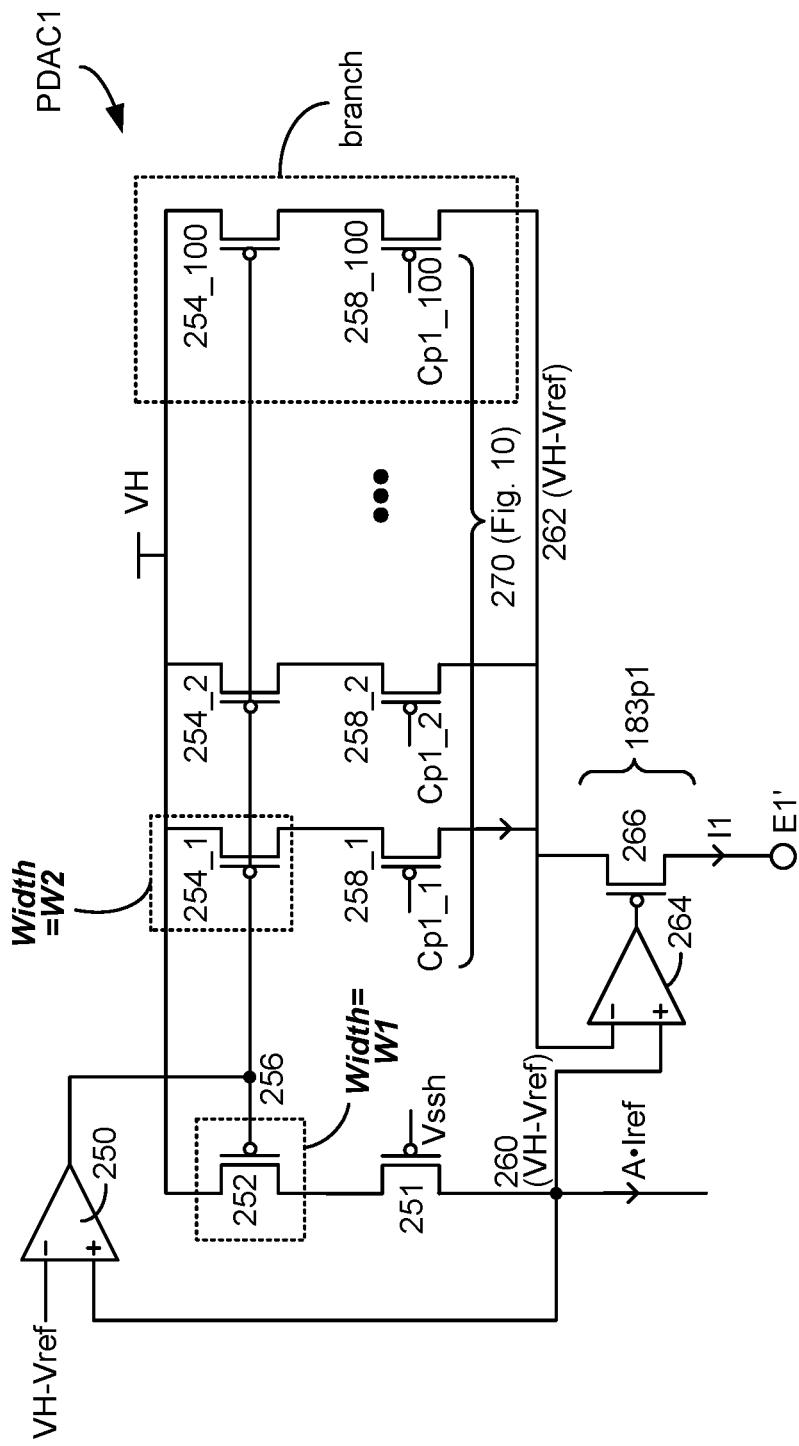
FIGS. 9A and 9B respectively show the circuitry details in one of the PDACs and in one of the NDACs, which includes a plurality of current branches controllable by switches.
Figure 9B:
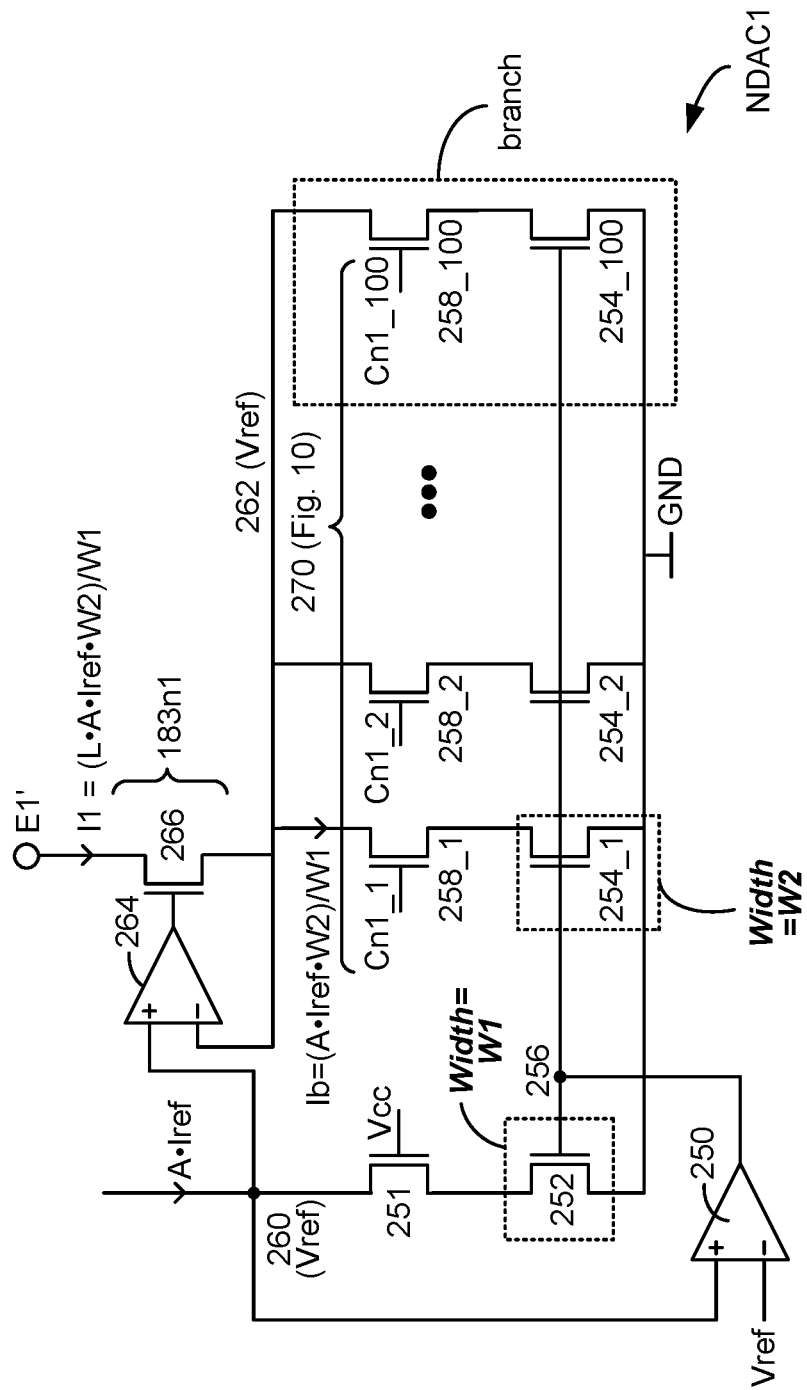

FIGS. 9A and 9B respectively show the circuitry for one of the PDACs (PDAC1) used to source current (+I1) to its electrode node (E1'), and the circuitry for one of the NDACs (NDAC1) used to sink current (−I1) from that electrode node. As a comparison of FIGS. 9A and 9B shows, the circuitry for the PDACs and NDACs are symmetric, although the PDACs are powered in the high power domain (VH/Vssh), while the NDACs are powered in the low power domain (Vcc/GND). Further, the polarity of the transistors in PDACs and NDACs are different, and thus control signals the PDACs receive (e.g., <C>) would be inverted from those received by the NDACs. Nonetheless, the PDACs in FIG. 9A essentially operate the same as does the NDACs in FIG. 9B. Thus, similar elements numerals are provided for the transistors in these figures, and both are discussed for simplicity primarily with reference to FIG. 9B.

NDAC1 in FIG. 9B receives at node 260 current A*Iref that was pushed to it by distributor 182n (FIG. 7B). This current passes through an always-on dummy transistor 251 to a resistance transistor 252. Resistance transistor 252 has a width W1, and can be formed to achieve this width W1 by wiring a plurality of transistors together in parallel, although this isn't shown. The gate of resistance transistor 252 is connected at node 256 to the gates of several branch transistors 254, each of width W2, which is preferably wider than W1 used in the resistance transistor 252. Again, each branch transistor could comprise a plurality of transistors wired in parallel. In the example shown, there are 100 branch transistors 254, each of which is connected to a switch 258 controlled by a control signal Cn1. A different numbers of branches could be used as well. Notice that resistance transistor 252 and branch transistors 254 are not coupled in a current mirror configuration (gate node 256 is not coupled to drain of transistor 252). However, A*Iref is still reproduced into each of the branch transistors 254, preferably with some amplification, as explained further below. The other sides of switches 258 are connected to a node 262.

In a preferred example, each of the branch transistors 254 (W2) is sized relative to the resistance transistor 252 (W1) to set a resistance difference between them, such that the resistance transistor 252 is W2/W1 times more resistive than each branch transistors 254. Further included in NDAC1 are operational amplifiers (op amps) 250 and 264. Op amp 250 receives node 260 at one of its inputs, and a reference voltage Vref at its other input. Vref can be generated by any number of well-known voltage generator circuits (not shown), such as temperature-independent bandgap voltage generators. The output of op amp 250 is connected to node 256, which is connected to the gates of the resistance transistor 252 and the branch transistors 254 to turn them on. Through feedback through the resistance transistor 252 and dummy transistor 251, op amp 250 will force its input, node 260, to match its other input, Vref. Thus, node 260 held to Vref.

Node 260 is input to an output stage 183n1 comprising an op amp 264 and an output transistor 266. Specifically, node 260 is input to the op amp 264, which in turn controls output transistor 266 to allow current to flow to electrode node E1' via an electrode output path. The other input to the op amp 264, node 262, is connected to opposite side of the output transistor 266 from the electrode node. Through feedback through the output transistor 266, the op amp 264 will force node 262 to match input node 260. Thus, just as node 260 is held at Vref, so too is node 262 held at Vref.

Switches 258 allow current to be provided to the electrode node based on the status of switch control signals <Cn1>. Quantifying the value of the provided current is explained subsequently, but for now it can be assumed that each branch transistors 254 provides a single "unit" of current. For example, assume it is desired to sink three units of current from electrode node E1'. (Again, an NDAC1 is illustrated in FIG. 9B, but one of the PDACs (see FIG. 9A) would source units of current to the electrode nodes). This can be accomplished by asserting any three of the control signals <Cn1>, such as Cn1_1, Cn1_2, and Cn1_3. This closes switches 258_1, 258_2, and 258_3 associated with these control signals, and allows L=3 branch transistors, 254_1, 254_2, 254_3, to each sink a unit of current from E1'. Thus, in sum, three units of current are sunk from electrode node E1' and hence electrode E1.

The quantity of current each branch provides is explained as follows. Assuming for the moment that the resistance of dummy transistor 251 is negligible compared to the resistance provided by the resistance transistor 252, Vref at node 260 is effectively dropped across the resistance transistor 252 (from its drain to its source). Current A*Iref flows through the resistance transistor 252, and therefore, the resistance of the resistance transistor 252 equals Vref/(A*Iref). Note that op amp 250 will set node 256 to a voltage necessary to bring resistance transistor 252 to this resistance.

The voltage drop across the branch transistors 254 are held to Vref just like the resistance transistor 252. Remember that node 262 is held at Vref, and thus is dropped across the series connection of the selected switches 258 and the active branch transistors 254. However, similar to the relationship of dummy transistor 251 to resistance transistor 252, the resistance across the switches 258 is negligible compared to the resistance of the branch transistors 254. As a result, Vref at node 262 is effectively dropped from the drain to the source of the branch transistors 254. Note that the width of the dummy transistor 251 (x*W1) can be sized relative to the width of the switches 258 (x*W2) in the same proportion that the resistance transistor 252 (W1) is sized relative to the branch transistors 254 (W2). This helps to ensure that the Vds drop across the branch transistors 254 equals that across the resistance transistor 252, which again is very close to Vref (perhaps approximately 100 mV smaller than Vref once the resistance of the dummy transistor 251 and switches 258 are considered).

Because the resistance of the resistance transistor 252 is Vref/(A*Iref), and because the resistance of the branch transistors 254 is W2/W1 less resistive, the resistance of each of the branch transistors 254 will be (Vref*W1)/(W2*A*Iref). Therefore, the current through each of the selected branch transistors 254 (Ib) can be calculated by dividing the voltage (Vref) across each branch transistor 254 by its calculated resistance, and so Ib=(A*Iref*W2)/W1. Because W2 is preferably larger than W1, notice that the current provided by the master DAC 180 (A*Iref) is amplified by a factor of W2/W1 in each of the selected branches. The currents Ib formed in each of the L (e.g., 3) active branches are then summed at node 262, and passed through output transistor 262, providing a total sunk current at electrode node E1' of I1=(L*A*Iref*W2)/W1.

Exemplary values assist in understanding NDAC1's operation, and the magnitudes of the various currents it produces. As described earlier, the master DAC 180 in one example can output currents A*Iref of 100 nA, 200 nA, 300 nA, . . . , 25.5 µA, depending on the value of the 'A' as set by amplitude bus <A>, and assuming a maximum value of 'A' of 255. Assume that the width W2 of the branch transistors 254 are 10 times the width W1 of the resistance transistor 252 (i.e., W2/W1=10). Each branch transistors 254 will amplify A*Iref current by this ratio, and thus be able to provide currents of Ib=1 µA, 2 µA, 3 µA, . . . , 255 µA (again, depending on 'A'). If it is assumed that all branches are selected (L=100), NDAC1 can produce a summed value of I1=0.1 mA, 0.2 mA, 0.3 mA, . . . , 25.5 mA. In other words, in this example NDAC1 imparts an amplification of 1000 to A*Iref, assuming all L=100 branches are selected. (This amplification however can be adjusted using the percentage control signals <Xn1>, as explained later with reference to FIGS. 12A-12C).

It should be noted that the reference current (Iref), the maximum amount by which the reference current can be amplified by the master DAC 180 (A), the relative widths of the resistance transistor 252 and the branch transistors 254 (W1 and W2), or their relative resistance more generally, and the maximum number of branches (L) can all be adjusted in different designs. Further, W2/W1 may equal one, and so each branch may simply reproduce A*Iref (i.e., Ib=A*Iref), which may still be considered an amplification of A * Iref in each branch. Alternatively, W2/W1 may even be less than one, meaning Ib would be smaller than A * Iref, which again may be considered as amplification.

Software limitations may also operate to constrain the total amount of current that the ASIC 160 can provide to the electrodes at any given time. For example, each PDAC and NDAC as described can source or sink 25.5 mA from its electrode, meaning in a 17 electrode IPG 10 (E1-E16, plus Ec) that the IPG could source or sink a total of 17*25.5 mA=433.5 mA. Such a large amount of current may be impractical: the compliance voltage VH may not be able to produce this, or the drain on the IPG's battery 14 may be too extreme. Such a large amount of current may also simply be unsafe. Thus, the total sourced or sunk current at any given time may be software limited to a more practical and safer value, such as 25.5 mA, even though such total value is below what the PDACs and NDACs together are capable of producing. Such limitation may be employed in software in the IPG 10 (in microcontroller block 150), or in the external controller used to program the IPG, that is, as a limitation constraining stimulation settings in the software of a clinician programmer or a hand-held patient programmer.

FIG. 9A shows an example of one of the PDACs (PDAC1). As one skilled in the art will appreciate, the circuitry for PDAC1 is largely "inverted" from that shown for NDAC1 in FIG. 9B, and has expected differences given its difference in polarity. For example, current-producing portions of PDAC1 are coupled to the compliance voltage VH instead of ground, thus allowing PDAC1 to source current to electrode node E1', allowing electrode E1 to operate as an anode (positive current). Notice that the reference voltage used by the PDACs comprises VH-Vref. This reference voltage will vary because, as explained in the Introduction, VH varies to keep the PDACs and NDACs operating at a power-efficient level. Further implications stemming from the variability of the compliance voltage VH are discussed later in conjunction with FIGS. 15A-16D.

The currents sourced to and sunk from the various electrodes—and thus the targeted tissue—may be effectively controlled in accordance with the foregoing description. However, in some embodiments it may be desirable to provide a further degree of control of the various electrode currents beyond that described above. For example, in some applications it may be desirable to provide for enhanced calibration for the respective electrode currents. This may be achieved in some embodiments by providing within DAC circuitry 172 circuitry that allows for gain and offset adjustment of the A*Iref signals provided to the NDACs and PDACs as discussed above.

As described above, and with reference to FIG. 5, the current at an electrode (e.g., E1) may be produced by first generating a reference current Iref (i.e., Iref_n and Iref_p) that is provided to a MDAC 180 (which may be divided into MDAC 180n and 180p; see FIGS. 7A & 7B). MDAC 180 also receives a current amplitude value A as specified by digital amplitude bus <A>, for example an 8-bit number. MDAC 180 then generates an A*Iref current that is provided to a distributor 182 (182n and 182p), which delivers the A*Iref signal (with the appropriate polarity) to the NDACs and PDACs that produce the currents at the electrodes (e.g., E1). The NDACs and PDACs will amplify the received A*Iref current as explained above (e.g., by 1000) to produce the electrode currents. The NDAC and PDACs may also receive digital percentage control signals (e.g., <Xp1> and <Xn1>), which inform the NDACs and PDACs of a percentage of amplitude A that each should deliver. (How the percentage control signals <X> control the PDACs and NDACs to affect the current produced at each electrode is explained later with respect to FIGS. 12A-12C).

Figure 10A:
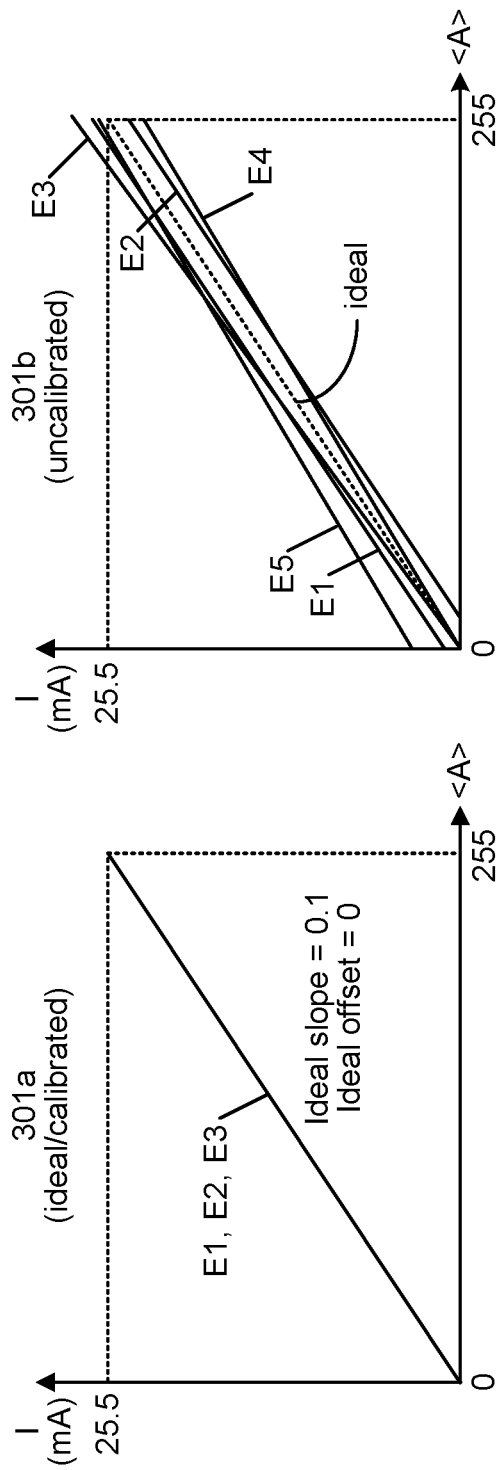
FIG. 10A shows uncalibrated versus calibrated electrode output currents versus digital amplitude values A provided to the master DAC.

In an ideal implementation, the current output at each electrode would be as illustrated in graph 301a of FIG. 10A, with each electrodes' current equaling zero when the amplitude value A as specified on digital amplitude bus <A> is zero, and increasing with a linear slope as A is increased to a maximum value (25.5 mA, when A=255). (Note that graph 301a assumes the relevant PDACs and NDACs are programmed to produce a maximum current—i.e., the X percentage control signals at the relevant DACs equal 100%).

However, because of variations in the manufacturing process, tolerances, and other non-idealities, the electrode currents produced may be as illustrated in graph 301b of FIG. 10A, with the current at different electrodes differing from the ideal response. In the illustrated example, the current at electrode E1 has a positive value when A=0 (corresponding to an undesired positive offset) but otherwise has an ideal slope. The current at electrode E2 has a negative value when A=0 (an undesired negative offset) but again otherwise has an ideal slope. The current at electrode E3 is zero when A=0 (an ideal offset) but otherwise has a high slope. The current at electrode E4 is also zero when A=0 (an ideal offset) but otherwise has a low slope. The current at electrode E5 is non-ideal in two manners: it has both a positive offset when A=0 and a low slope.

Figure 10B:
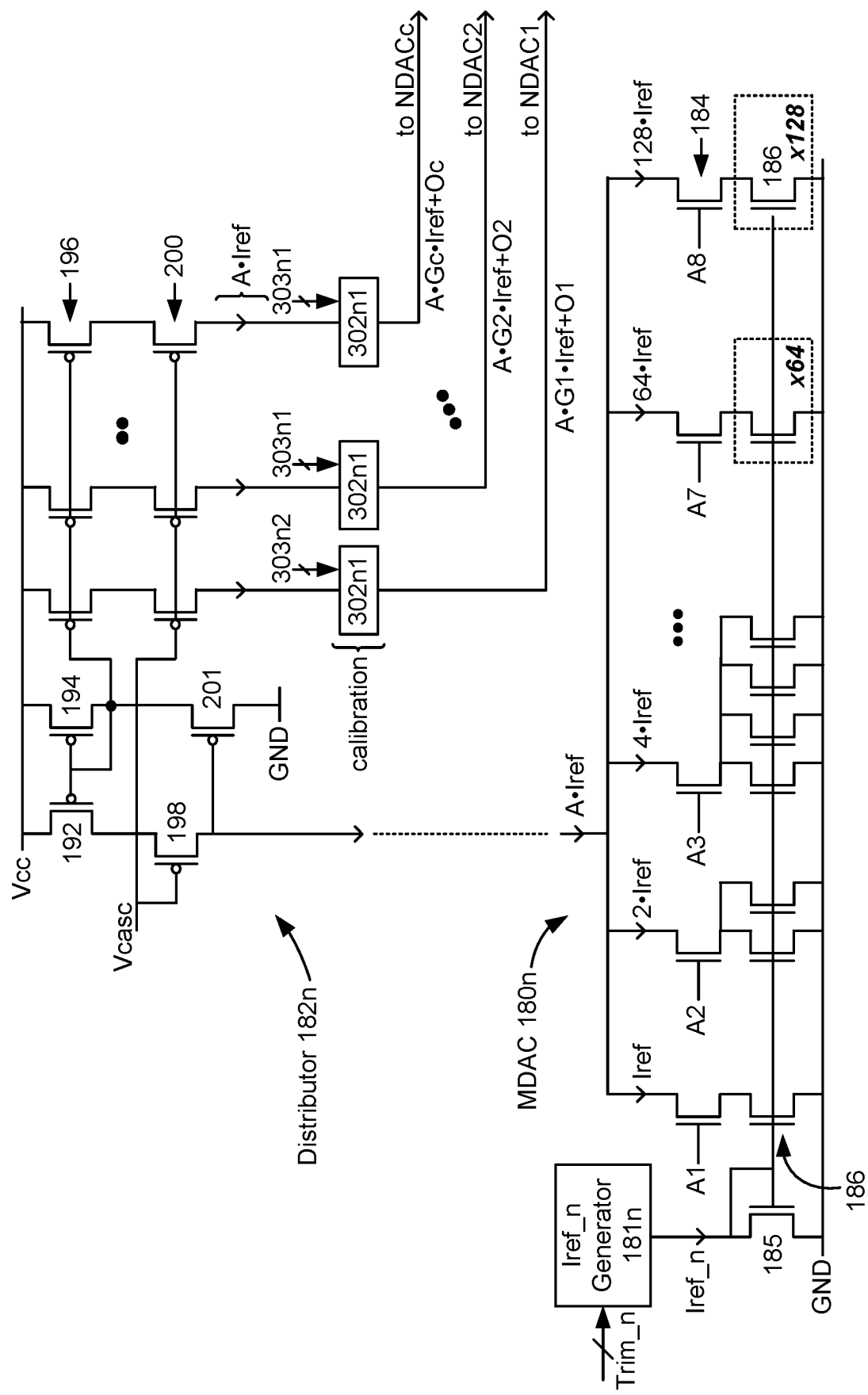
FIG. 10B shows inclusion of per-electrode calibration circuits within the DAC circuitry.

Because these non-ideal electrode currents may be undesirable, each electrode may be made to produce an ideal output (i.e., a calibrated output, 301a) by changing the circuitry used to generate such currents. In particular, this goal may be achieved by circuitry that calibrates A*Iref as sent to each of the PDACs and NDACs. FIG. 10B illustrates a high-level diagram of the "NDAC side" of the system similar to that described above with reference to FIG. 7B, with added calibration circuits 302ni described in greater detail below. While the "PDAC side" of the system is not expressly shown, the PDAC side circuitry would likewise add calibration circuits 302pi to the PDAC side circuitry shown in FIG. 7A, and would operate substantially similarly after accounting for the difference in polarity between these circuits.

As FIG. 10B shows, there is preferably a calibration circuit 302ni provided for each of the A*Iref outputs provided by the distributor 182n, i.e. for each of the outputs sent to the NDACs at each electrode. As explained in further detail below, each of the calibration circuits 302ni adjusts A*Iref to produce a current with an adjusted gain (G) and/or offset (O). In other words, each calibration circuits produces A*G*Iref+O from A*Iref, which allows for correction of the errors discussed above with respect to FIG. 10A. Each calibration circuit 302ni may be controlled by control signals 303ni which are preferably unique to each. As explained further below, control signals 303ni allow A*Iref to be independently adjusted (e.g., to form A*G1*Iref+O1; A*G2*Iref+O2), thus allowing the NDACs at each electrode to receive independently-calibrated versions of the A*Iref current. Although the calibration circuits 302ni as described apply linear (i.e., gain and offset) compensation to the A*Iref signals, they may provide for non-linear compensation, including, for example, compensation based on higher order polynomials, exponential, logarithmic, or other suitable functions. See, e.g., U.S. Patent Application Publication 2021/0275798 (describing non-linear adjustment in an IPG's DAC circuitry).

In some embodiments, calibration circuits may be independent from the distributor circuitry as shown in FIG. 10B, and thus the calibration circuits 302ni (302pi) may be interposed between the distributor 182n (182p) and the NDACs (or PDACs). Alternatively, the calibration circuits 302ni (302pi) may be incorporated into the NDAC (or PDACs) at each electrode.

Figure 10C:
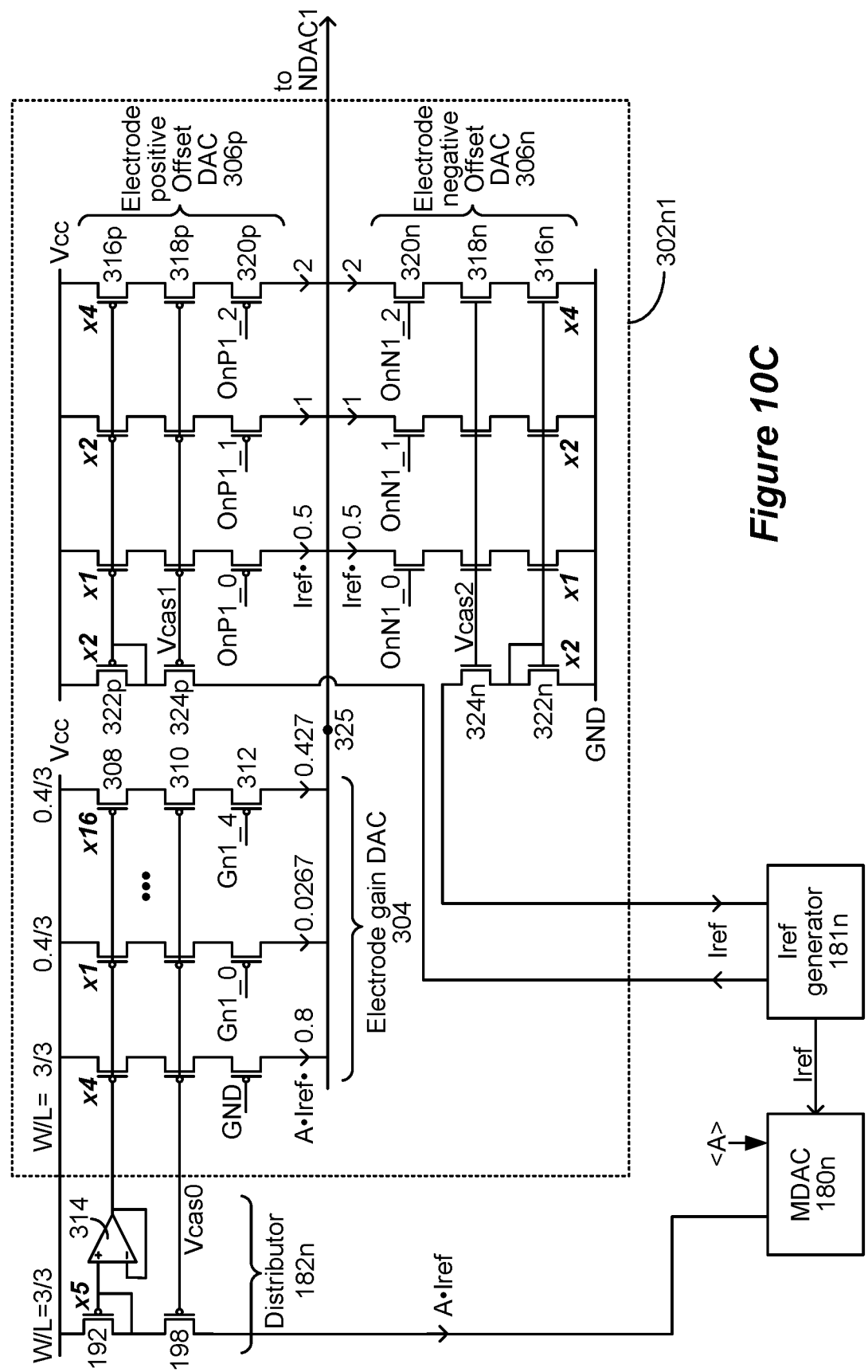
FIG. 10C shows details within one of the calibration circuits, including an electrode gain DAC and positive and negative electrode offset DACs.

Alternatively, the calibration circuits may comprise a modification to, or be incorporated within, the distributor circuitry, and this is shown in FIG. 10C. FIG. 10C shows the calibration circuit 302n1 that provides current to NDAC1 at electrode E1. This circuitry would be duplicated for other NDAC side calibration circuits, such as 302n2 that provides current to NDAC2 at electrode E2, etc., and would further be symmetrically duplicated (with polarities changes) for the PDAC side calibration circuits, such as 302p1 that provides current to PDAC1 at electrode E1, and 302p2 that provides current to PDAC2 at electrode E2, etc (see FIG. 10E).

As shown in FIG. 10C, calibration circuit 302n1 includes an electrode gain DAC 304, an electrode positive offset DAC 306p, and an electrode negative offset DAC 306n. Also shown in FIG. 10C are aspects common to the NDAC side calibration circuits 302n1, including the MDAC 180n, which provides A*Iref to distributor 182n, and Iref generator 181n that provides Iref to the MDAC 180n (see FIG. 7B). Notice that the Iref generator 181n also provides different polarities of Iref to the positive offset DAC 306p and the negative offset DAC 306n. A*Iref as before is provided to distributor 182n, namely into an input leg of a current mirror comprising transistors 192 and 198. Element 314 comprises a buffer.

The gain DAC 304 includes output legs of the current mirror, and at least some of these legs are selectable to provide a current at node 325 which is supplied to NDAC1. In particular, certain output legs are selectable using gain control signals <Gn1>. Gain control signals <Gn1> comprise some of the control signals within control signals 303n1, as explained later with reference to FIG. 10D. Notice that the output legs in the gain DAC 304 modify the non-selectable output legs (formed from transistors 196 and 200 in FIG. 7B) used in the distributor 182n as described previously.

Each output current leg in the gain DAC 304 includes in this example one or more parallel-connected mirror transistors 308, a cascode transistor 310, and a selection transistor 312. Similar to what was explained earlier, cascode transistors 198 and 310 are controlled by voltage Vcas0, but this detail is not important to understanding operation of the circuit. Current mirror transistors 308 produce a scalar of A*Iref provided to transistor 192, with the amount of current depending on the sizing of the transistor(s) 308 relative to transistor(s) 192, as well as the number of transistors that are provided in parallel both at 192 and 308.

The first output leg in gain DAC 304 is always on in the depicted example, because the gate of its p-channel selection transistor 312 is asserted low (GND). The transistors 192 and 308 in this leg are sized the same, with a width/length ratio of 3μ/3μ. There is also a 5/4 ratio of the number of paralleled transistors (i.e., there are 5 transistors 192, and 4 transistors 308). This means this first output leg will carry 0.8*A*Iref, and will thus always supply this amount of current to node 325.

The other output legs in the gain DAC 304 have selection transistors 312 that are controlled by one of the gain control signals <Gn1>, of which there are five in this example (Gn1_0 to Gn1_4). The current mirror transistors 308 in these selectable legs are sized differently (W/L=0.4 μ/3μ) from transistor(s) 192 (3μ/3μ), which scales the currents these legs carry by a factor of 0.4/3. Further, each selectable leg includes a binary-weighted different number of paralleled current mirror transistors 308 (1, 2, 4, 8, and 16) to exponentially increase the amount of current these legs will carry. Thus, the first leg when selected by gain control signal Gn1_0 will carry approximately 0.0267*A*Iref (1*0.4/(3*5)); the second leg when selected by gain control signal Gnu_1 will carry approximately 0.0533*A*Iref ((2*0.4)/(3*5)); the third leg when selected by gain control signal Gn1_2 will carry approximately 0.107*A*Iref; the fourth leg when selected by gain control signal Gn1_3 will carry approximately 0.213*A*Iref; and the fifth leg when selected by gain control signal Gn1_4 will carry approximately 0.427*A*Iref.

Therefore, and depending on which gain control signals Gn1 are asserted, the gain DAC 304 can produce a current at node 325 from 0.8*A*Iref (G=0.8, when none of the gain control signals Gn1 are asserted) to 0.8+0.0267+0.0533+0.107+0.213+0.427=1.627*A*Iref (G=1.627, when all of the gain control signals are asserted), in 32 steps of 0.267*A*Iref. In short, gain DAC 304 allows the gain G of A*Iref to be adjusted from 0.8 to 1.627, which can be used to address a slope error in the electrode current, as occurs for electrodes E3, E4, and E5 in FIG. 10A (301b). FIG. 10D summarizes the potential gains G in this example, and shows which of the gain control signals are asserted (+) or not asserted (−). (One skilled will understand that signals will be asserted low if the gain DAC 304 comprises p-channel transistors, but would be asserted high when this DAC comprises n-channel transistors, as would be the case for the PDAC side calibration circuits 302pi). Notice from FIG. 10D that if an electrode's current is ideal (not requiring calibration), the gain G would be set to 1, requiring at least some of the gain control signals to be asserted (see decimal entries 7 or 8, each equally close to 1). Of course, the gain DAC 304 as described is just one example, and gain values producible by this DAC can be modified in other designs by changing the relative sizes and numbers of the transistors, the number of legs and gain control signals, etc.

Referring again to FIG. 10C, calibration circuit 302n1 also includes a positive offset DAC 306p and a negative offset DAC 306n either of which can be used to address an offset error, as occurs for electrodes E1, E2, and E5 in FIG. 10A (301b). More specifically, for electrodes having a positive offset (e.g., E1, E5), a negative offset may be applied by the negative offset DAC 306n to "offset" this error. Similarly, for electrodes having a negative current offset error (e.g., E2), a positive offset may be applied by the positive offset DAC 306p to "offset" this error.

Like the gain DAC 304, each of the offset DACs 306p and 306n may be constructed as binary-weighted current mirrors. The input leg of each DAC 306p/n includes an input transistor 322p/n and a corresponding cascode transistor 324p/n, with the input legs at the DACs receiving Iref with different polarities as shown. In the example of FIG. 10C, each offset DAC 306p and 306n is a three-bit DAC, with offset DAC 306p receiving offset control signals <OnP1> (OnP1_0, OnP1_1, and OnP1_2), and offset DAC 306n receiving offset control signals <OnN1> OnN1_0, OnN1_1, and OnN1_2). Offset control signals <OnP1> and <OnN1> comprise some of the control signals within control signals 303n1, as explained later with reference to FIG. 10E. Positive offset control signals OnP1_0, OnP1_1, and OnP1_2 are applied to the gates of selection transistors 320p in the output legs of the DAC 306p to set a magnitude of a positive current offset (+O) at node 325. Negative offset control signals OnN1_0, OnN1_1, and OnN1_2 are similarly applied to the gates of selection transistors 320n in the output legs of the DAC 306n to set a magnitude of a negative current offset (−O) at node 325. This drive arrangement thus requires a total of six bits, but this could also be modified. For example, four bits could also be used: one bit to select either of the offset DACs 306p or 306n, and three bits to set the offset magnitude O.

As shown, the output legs of the offset DACs 306p/n include three transistors: current mirror transistors 316p/n, cascode transistors 318p/n, and the selection transistors 320p/n. In this example, the transistors used to form the input transistors 322p/n and the current mirror transistors 316p/n are sized the same, and thus each output leg will form a scalar of Iref in accordance with the different number of paralleled transistors provided for each. In this example, there are two paralleled transistors for the input transistors 322p/n. The first output legs include only one current mirror transistor 316p/n, and so these legs when selected (OnP1_0 or OnN1_0) will carry 0.5*Iref (+0.5*Iref or −0.5*Iref). The second legs have two-paralleled current mirror transistors 316p/n, and so these legs when selected (OnP1_1 or OnN1_1) will carry Iref (+Iref or −Iref). The third legs have four-paralleled current mirror transistors 316p/n, and so these legs when selected (OnP1_2 or OnN1_2) will carry 2*Iref (+2*Iref or −2*Iref). Notice that changing the relative sizing of the transistors 322p/n to 316p/n could also be used to set the currents in the output legs, as explained above.

Given this arrangement, and depending on the status of positive offset control signals <OnP1>, a positive current offset can be added to node 325 from 0 to 3.5*Iref in 0.5*Iref increments. Likewise, and depending on the status of negative offset control signals <OnN1>, a negative current offset can subtracted from node 325 from 0 to −3.5*Iref in −0.5*Iref increments, and thus 0 can range from −3.5*Iref to +3.5*Iref. FIG. 10D summarizes these possible offsets and describes their values assuming a current of Iref=100 nA is used, and further shows which of the offset control signals are asserted (+) or not asserted (−) to produce them. Notice from FIG. 10D that if an electrode's current is ideal (not requiring calibration), the offset O would be set to 1, and all of the offset control signals would be deasserted.

In summary, the current at node 325 equals A*G*Iref (as provided by the gain DAC 304) plus O (as provided by offset DACs 306p or 306n), therefore providing in sum A*G*Iref+O at node 325.

Figure 10E:
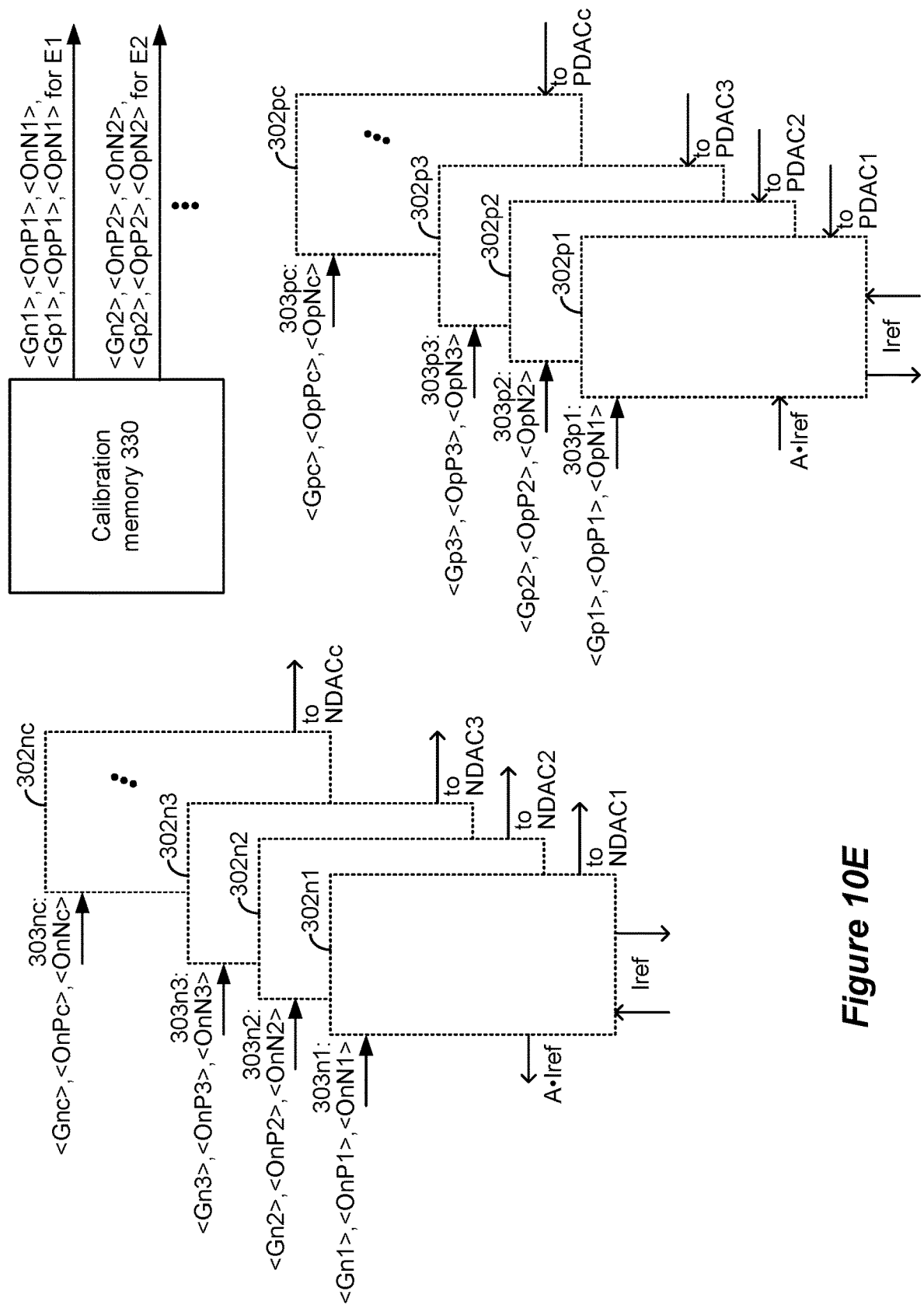
FIG. 10E shows the calibration circuits and related control signals to control the electrode gain DAC and the positive and negative electrode offset DACs at each electrode.

FIG. 10E shows the calibration circuits 302ni and 302pi relevant to each electrode Ei and their associated calibration control signals 303ni and 303pi. Notice that gain control signals <Gni> and offset control signals <OnPi> and <OnNi> calibrates the A*Iref current provided to electrode Ei's NDAC when acting as a cathode to sink current. Likewise, gain control signals <Gpi> and offset control signals <OpPi> and <OpNi> calibrate the A*Iref current provided to electrode Ei's PDAC when acting as an anode to source current. These control signals may be stored in a calibration memory 330. Calibration memory 330 is preferably non-volatile, and may be included within the ASIC 160 in which the DAC circuitry 172 is formed, although calibration memory 330 may also be provided "off chip" within the IPG. Relevant control circuitry in the ASIC 160, such as the Pulse Definition Circuit (PDC) (FIG. 8A) or the microcontroller block 150 (FIG. 4B), can read the calibration memory 330 and provide the relevant calibration control signals 303 to their associated calibration circuits 302.

Figure 10F:
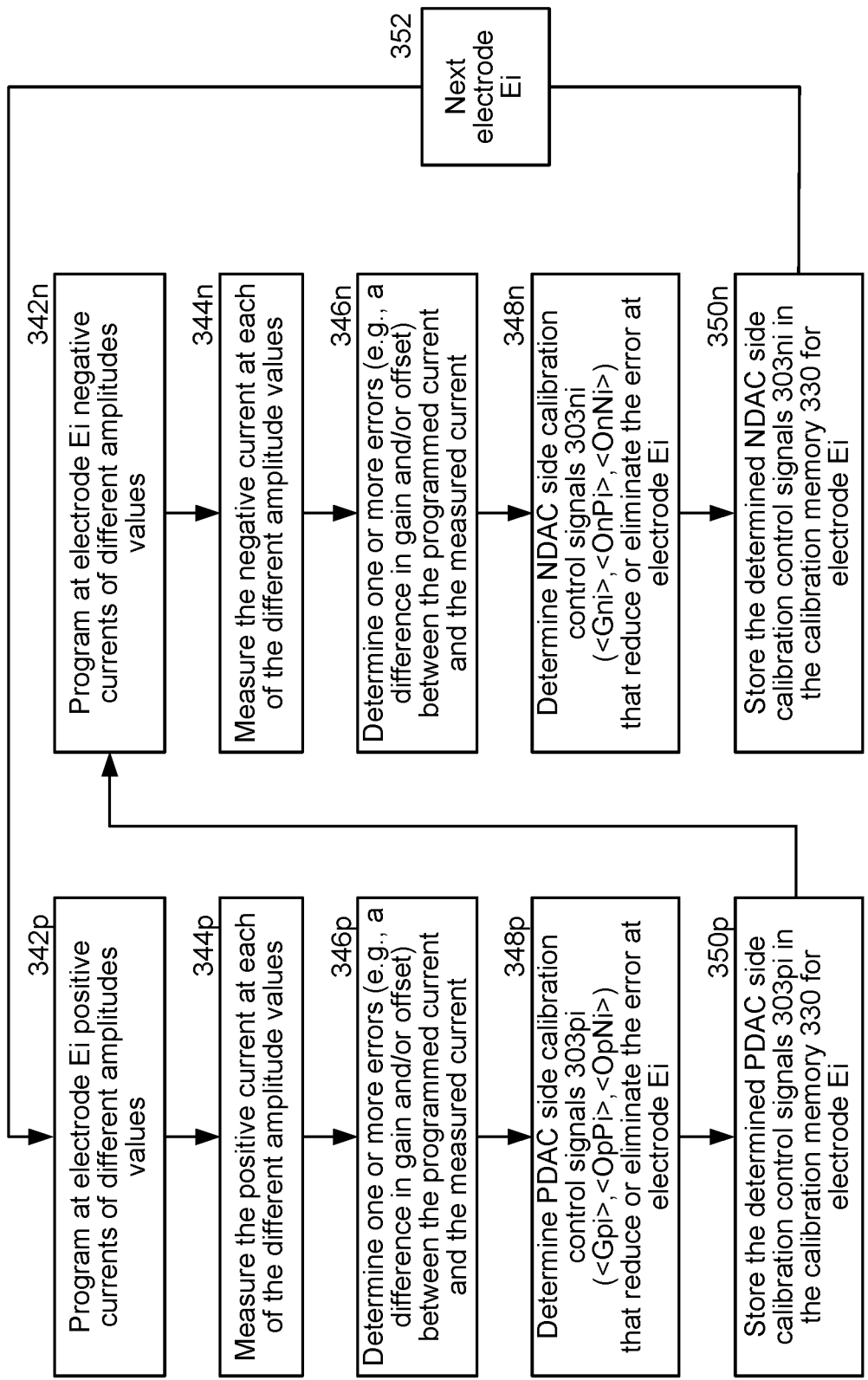
FIG. 10F shows a calibration algorithm useable to program the calibration circuits to produce calibrated electrode currents.

A calibration algorithm 340 can be used to determine the calibration control signals 303 for each electrode and to store them in the calibration memory 330 for later use, as shown in FIG. 10F. Calibration algorithm 340 can be used during useful operation of the IPG, thus allowing the electrode currents to be calibrated even after manufacture and after the IPG has been implanted in a patient. That being said, the calibration algorithm 340 may also be used initially during manufacture of either the ASIC 160, the IPG, or both. Calibration algorithm 340 may be automated by an external device in communication with the IPG (e.g., a clinician's programmer) or by testing equipment (e.g., wafer probes, chip testers) used during manufacture of the ASIC 160 or the IPG. Preferably, calibration occurs on a per-electrode basis. In the depicted example of calibration algorithm 340, PDAC side circuitry for an electrode is calibrated first in steps 342p-350p, followed by analogous steps 342n-350n for the NDAC side circuitry.

At step 342p, the ASIC 160 or the IPG is programmed to provide at a first electrode (e.g., E1) positive currents of different amplitudes, i.e., currents at different amplitude values as prescribed by digital amplitude bus <A>. These currents can be provided to electrode E1's electrode node 61a at the ASIC 160 (the relevant pin or bond pads), or at electrodes E1 of the IPG (the electrode contacts in its lead connector 26 (FIG. 1A) or on a connected lead). This programmed current can be thought of as an ideal current 301a as shown in FIG. 10A. At step 344p, the resulting current is measured at E1 at each of the different amplitudes. At step 346p, one or more errors is determined between the programmed (ideal) and measured currents. This error could comprise an error in the slope and/or the offset of the measured current (see 301b, FIG. 10A) compared to the programmed (ideal) current (see 301a, FIG. 10A), although as noted earlier non-linear errors may also be determined. Note that it is preferable to at least program (342p) and measure (344p) the current with A set to zero and to its maximum (255) to span the entire operating range that the DAC circuitry can produce. However, providing current at a subset of values within this range (e.g., A=0, 64, 128, 192, 255), or at all possible values for A, will provide more information regarding how the measured electrode current may be varying from the ideal at step 346p. For example, if several measurements are taken, they can then be curve fit by the algorithm 340 via linear regression to determine the slope and offset of the electrode current.

At step 348p, PDAC side calibration control signals 303p1 (<Gp1>, <OpP1>, <OpN1>) are determined to reduce or eliminate the error for electrode E1 being tested. These control signals may be determined automatically (e.g., by determining the resulting gain and offset through an analysis of the measured currents), or may be arrived at iteratively by adjusting the control signals until the error is minimized. FIG. 10G later describes steps the calibration algorithm 340 can undertake to minimize such error. In either case, once the 303p1 control signals are determined for E1, they are stored in the calibration memory 330 in step 350p. During operation of the IPG, the calibration memory 330 will be read to send the calibration control signals 303p1 to calibration circuit 302p1, which will if necessary adjust the A*Iref current sent to PDAC1 when E1 has been selected as an anode (positive) electrode.

Analogous steps 342n-350n provide for NDAC side calibration for electrode E1, and similarly results in determining and storing control signals 303n1 (<Gn1>, <OnP1>, <OnN1>), which adjusts the A*Iref current sent to NDAC1 when E1 has been selected as a cathode (negative) electrode. If there are further electrodes left to calibrate (e.g., E2, E3, etc.), step 352 causes the process to repeat to determine the calibration control signals for those electrodes (e.g., 303p2, 303n2, 303p3, 303n3, etc.).

Notice benefits from the disclosed approach to calibration. First, the currents provided to each electrode's NDAC and PDAC are independently calibrated, thus calibrating each electrode's current whether it is acting as an anode to source current or a cathode to sink current. Second, by measuring the resulting current at the electrode, calibration compensation can occur regardless where non-ideal circuit operation may be present in the DAC circuitry 172. Non-ideal currents may result from non-idealities in A*Iref as produced and distributed (e.g., by MDAC 180 and distributor 182), or in the PDAC or NDACs themselves (which as discussed earlier can amplify the received A*Iref current to produce larger currents at the electrodes). In this regard, note that A*Iref as provided to the PDACs and NDACs may be perfectly ideal (e.g., increasing linearly from 0 to 25.5 µA as amplitude value A increments from 0 to 255), with amplification at the PDAC or NDACs producing non-ideal electrode currents. Nevertheless, this can be compensated for by adjusting A*Iref (even away from otherwise ideal performance) so that error in the resulting electrode currents is reduced or eliminated.

FIG. 10G shows an example of a non-ideal positive electrode current at a particular electrode (e.g., E1), and shows how calibration algorithm 340 can control the relevant calibration circuit (302p1) via relevant control signals (<Gp1>, <OpN1>, <OpP1>) to bring the electrode current closer to ideal. In this example, and looking only at measurements taken at extreme amplitude values (A=0, A-255), the electrode current has an undesired positive offset of 0.1 mA when A=0, and an undesirable low slope ((24.0-0.1)/(255-0)=0.0937). (In this example, an ideal slope would be 0.1=25.5/255). The calibration algorithm 340 in the depicted example first addresses the offset. A negative offset of −0.1 is needed at electrode E1, and after dividing out the amplification (e.g., 1000) provided by the PDAC1, this means the current at node 325 input to the PDAC needs a negative offset of −100 nA. Consulting FIG. 10D, this requires only offset control signal OpN1_1 to be asserted in the electrode negative electrode offset DAC 306n. Because no positive offset is needed, the control signals in the electrode positive electrode offset DAC 306p can be deasserted.

Next, the electrode current's slope can be addressed, which involves control of the electrode gain DAC 304. A gain G of 1.066 (0.1/.0937) is needed to boost the low slope, and consulting FIG. 10D, is it is seen that setting the gain control signals <Gp1> to a decimal value of 10 is closest to this ideal slope, meaning that only gain control signals Gp1_3 and Gp1_1 are asserted. With the control signals (301p1) set in this manner, the positive electrode current at E1 is brought closer to ideal. As calibration algorithm 340 contemplates, the negative current at this electrode can next be tested, followed by testing the positive and negative currents at other electrodes.

Figure 11A:
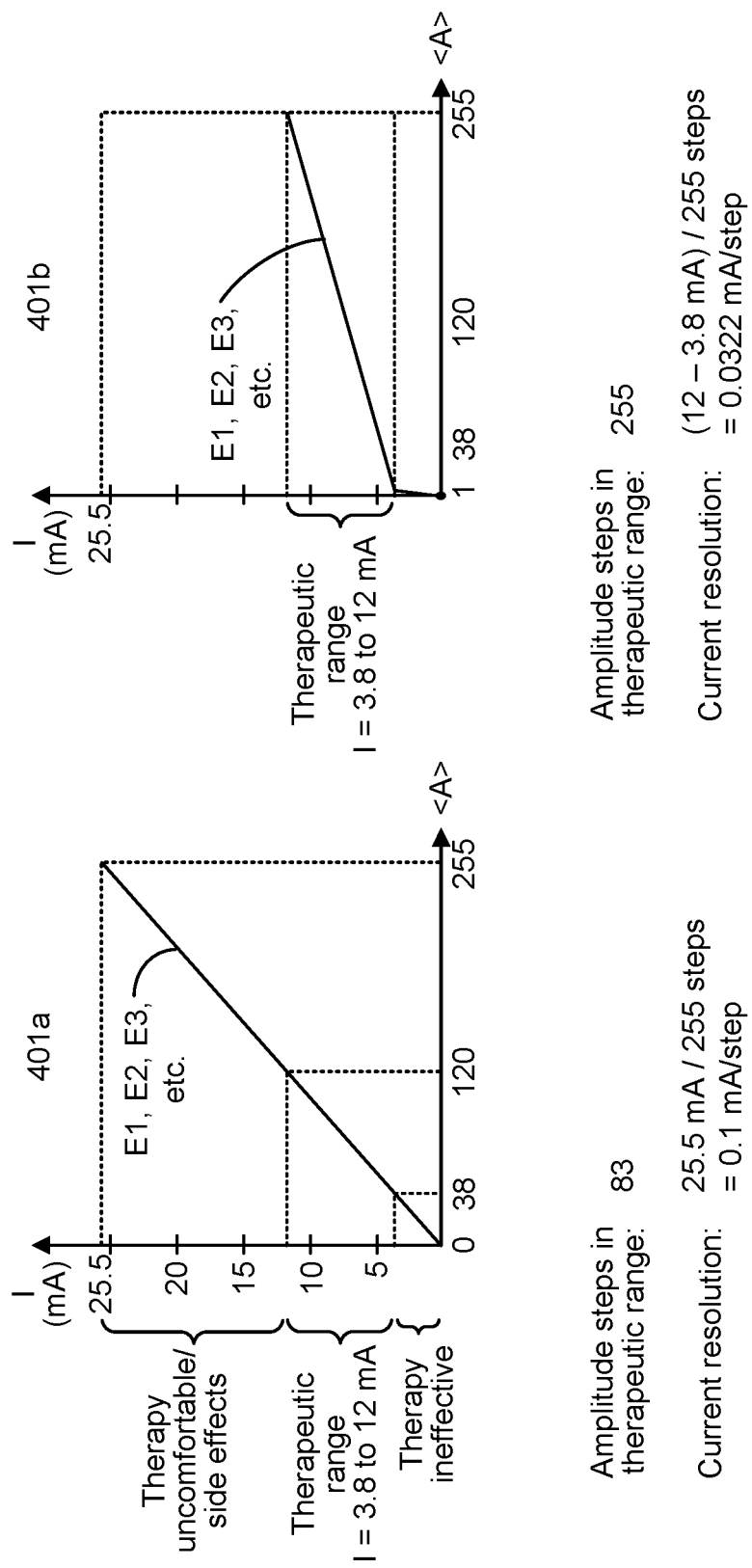
FIG. 11A shows electrode output currents versus digital amplitude values A provided to the master DAC, and modification of the response such that a therapeutic range of currents spans over the entire working range of the DAC at all values A.

Still other useful modification can be made to the DAC circuitry 172. FIG. 11A shows in graph 401a ideal performance of the DAC circuitry (perhaps as assisted by use of the calibration circuits 302 just described), which as noted earlier provides a linear increase in each electrode's current as amplitude value A provided by the digital amplitude bus <A> is incremented. Given the number of amplitude steps (255), and assuming a maximum current producible by the NDACs and PDACs of 25.5 mA, operation of the DAC circuitry 172 provides a current resolution of 0.1 mA per amplitude step.

Operating the DAC circuitry 172 in this manner may not be optimal for a given patient, because certain currents that the NDACs and PDACs can produce may be irrelevant for a given patient. Assume for example in graph 401a that a therapeutic range of electrode currents for a given patient spans from 3.8 mA to 12 mA. In other words, symptomatic (e.g., pain) relief is provided to the patient when the electrode currents are within this range. At lower currents (<3.8 mA), the electrodes currents may not be strong enough to provide any relief in symptoms. At higher currents (>12 mA), the stimulation provided to the patient may be uncomfortable, or the patient may experience undesired side effects. In short, for this patient, it will never make sense to provide an electrode current outside of the therapeutic range from 3.8 to 12 mA, and therefore amplitude values A less than 38 and greater than 120 will never be used.

This can be unfortunate given the design of the DAC circuitry 172, particularly because the amplitudes values that the patient may use within the therapeutic range are limited. In this example, there are only 83 amplitude value steps (from A=38 to A 120) out of a potential 255 amplitude values that can be used by the patient, which limits current adjustment for the patient. Moreover, the current resolution is limited (held constant) to 0.1 mA by the DAC circuitry 172. This may be too coarse of a resolution, particularly when the patient's therapeutic range of electrode currents is relatively narrow. For the patient in this example, it may be desirable to allow the electrode currents to be adjusted by amplitude value A in smaller current increments (0.01 mA, 0.03, mA, 0.05 mA, etc.) to allow for fine tuning of the stimulation therapy the patient is receiving. Yet, this can't be affected in the DAC circuitry design as described to this point.

It would be preferable in this circumstance that the DAC circuitry 172 perform as shown in graph 401b. In this example, the entire range of amplitude values A is used from 1 to 255 to provide therapeutically meaningful electrode currents within the therapeutic range for the patient, with A=1 providing an electrode current at the low end of the therapeutic range (3.8 mA) and with A=255 (the maximum amplitude value) providing an electrode current at the high end of the range (12 mA). (Lowest amplitude value A=0 may still provide an electrode current of zero, because it may be preferable for safety to reserve an amplitude value for which no electrode current is provided. This subtlety is however largely ignored in discussion that follows). As shown in FIG. 11A, such DAC performance would reduce the current resolution to 0.322 mA per amplitude step, thus providing finer current control for the patient. In effect, performance as shown in graph 401b would allow the DAC circuitry 172 to "zoom" in on the therapeutic range of electrode currents, using all possible amplitude values to navigate this range, and otherwise ignoring currents with magnitudes outside of this range. Providing the performance as shown graph 401b may also be useful for other reasons not relevant to a patient's therapeutic range.

Figure 11B:
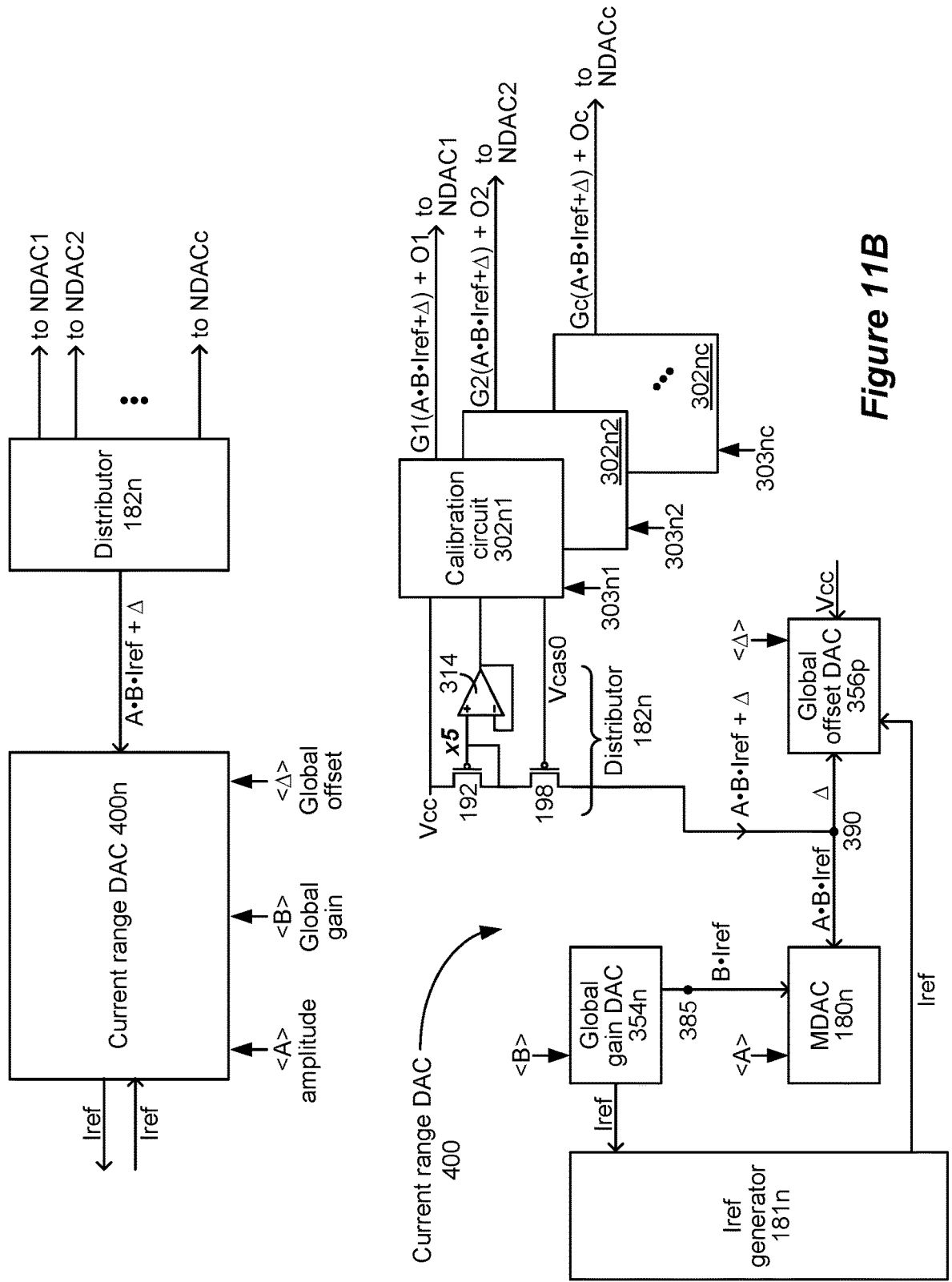
FIG. 11B shows inclusion of current range DAC circuitry within the within the DAC circuitry useable to achieve the desired response shown in FIG. 11A, which includes global gain and offset circuitry in addition to the master DAC.

FIG. 11B shows modification to the DAC circuitry 172 to achieve these goals and to allow performance of the DAC circuitry 172 to be tailored in the manner shown in graph 401b. As before, only NDAC side circuitry is shown, but there would preferably also be reverse-polarity PDAC side circuitry (see FIG. 11G). As shown at the top of FIG. 11B, a current range DAC 400n is provided which (similar to the master DAC 180n described earlier, FIG. 7B) provides a current to the distributor 182n. While the master DAC 180 described earlier only provided A*Iref to the distributor 182n, the current range DAC 400n provides a modified version of this current, namely A*B*Iref+Δ, where B comprises a global gain, and where Δ comprises a global offset. The current range DAC 400n receives as digital control signals the total anodic/current amplitude <A> indicating amplitude value A, a global gain bus <B> indicating the global gain B, and a global offset bus <Δ> indicating the global offset Δ. As explained further below, the current range DAC 400n will constrain the total current producible at the electrodes to within a range of values, particularly in accordance with values for the global gain B and the global offset Δ.

The bottom of FIG. 11B shows further details regarding the current range DAC 400n. The current range DAC 400n includes the master DAC 180n which as described earlier receives the prescribed amplitude value A from digital amplitude bus <A>. The current range DAC 400n further includes as new additions a global gain DAC 354n which receives the global gain B from global gain bus <B>, and a global offset DAC 356p which receives the global offset bus <Δ>. These DACs 354n and 356n are similar to the electrode gain DAC 304 and electrode offset DACs 306p and 306n in the calibration circuits 302 described earlier (FIGS. 10A-10G), but they apply a current gain and offset globally to the NDAC and PDACs at all of the electrodes, as will be explained shortly. The global DACs 354n and 356n may or may not be used in conjunction with the calibration circuits 302 to calibrate the currents at the electrodes.

As shown, the global gain DAC 354n receives Iref (e.g., 100 nA) from the Iref generator circuit 181n, and under control of a global gain bus <B>, provides an output current at node 385 equal to B*Iref. In other words, the global gain DAC 354n imparts a gain B to Iref as specified by a global gain value B carried by bus <B>. The output current B*Iref is then provided to the master DAC 180n, and essentially acts as a new (scaled) reference current for the master DAC to process. As before, the master DAC 180n receives an amplitude value A from the digital amplitude bus A, and scales the reference current it receives (B*Iref) by this amount, and so produces A*B*Iref at its output at node 390.

The global offset DAC 356p also outputs to node 390, and provides a current offset Δ to node 390, as specified by a global offset bus <Δ>. Thus, the summed operation of MDAC 180n and global offset DAC 356p produces an output of A*B*Iref+Δ at node 390. The output at node 390 is then input to the distributor circuitry 182n. As discussed earlier, the distributor can provide its output to individual electrode calibration circuits 302. That being said, it is not necessary to use calibration circuits 302 in conjunction with the global DACs 354n and 356n, and instead the distributor 182n (or 182p) may instead merely distribute the output A*B*Iref+Δ to the NDACs (or PDACs) without further modulation (see, e.g., FIGS. 7A & 7B). Again, although not shown in FIG. 11B, analogous PDAC side circuitry (354p, 356p) would preferably also be present (see FIG. 11G).

Figure 11C:
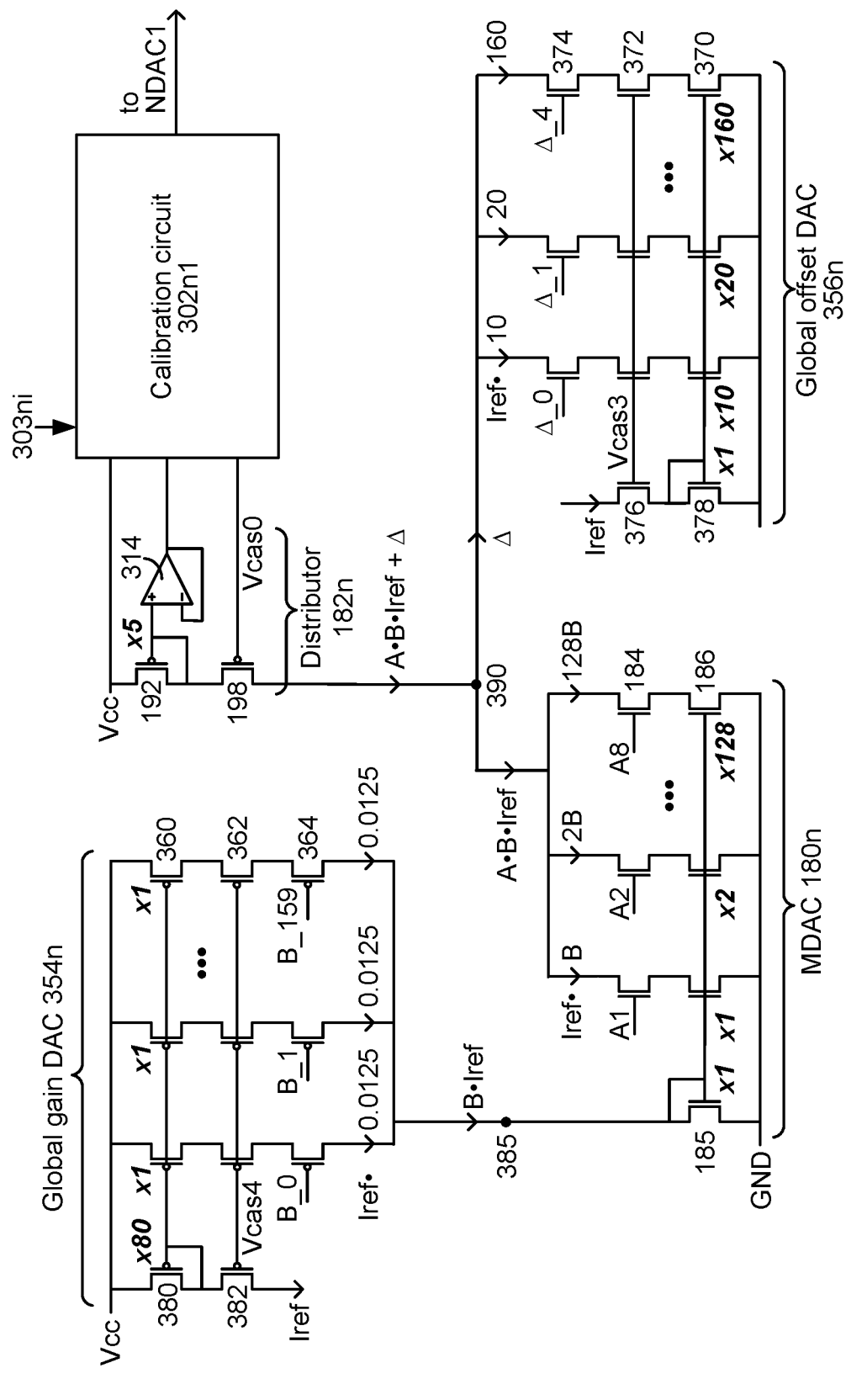
FIG. 11C shows details of the current range DAC circuitry.

Circuitry details for the current range DAC 400n are shown in FIG. 11C. The global gain DAC 354n receives Iref at its input transistor 380 which forms current mirrors with transistors 360 in the output legs of the DAC 354n. (Cascode transistors such as 382 and 386 are not important to understanding circuit operation). In this example, the transistors 380 and 360 are sized the same, but there are 80 transistors 380 provided in parallel in the input leg, but only one transistor 360 in each of the output legs. This produces a current of 0.0125*Iref in each of the output legs when selected. In this example, there are 160 output legs, with selection transistors 364 receiving one of 160 global gain control signals (B_0 to B_159) as carried by global gain bus <B> (FIG. 11B). Notice then that global gain DAC 354n in this example is thermometer encoded (similar to the DAC shown in FIG. 7C), meaning that as global gain value B increases, an increasing number of the global gain control signals B_i are asserted, which increases the magnitude of the current output at node 385. More specifically, as global gain B is incremented, the current at node 385 is incremented in steps of 0.0125*Iref up to 2*Iref. This is summarized in FIG. 11E, which shows asserted control signals B_i, and the resulting current (global gain B) at node 385. In sum, the global gain DAC 354n can provide a global gain B to Iref ranging from 0.0125 to 2, as shown in FIG. 11E. Note that if global gain DAC 354n does not need to impart a special gain (i.e., B=1), certain of the control signals (B_79 to B_0) will still need to be asserted.

Referring to FIG. 11C, the output B*Iref is provided at node 385 as a reference current to the master DAC 180n. The master DAC 180n otherwise operates as before (see FIG. 7B), except that its reference current (Iref) has now been scaled by global gain value B. Therefore, the master DAC outputs a current at node 390 which is scaled both by the amplitude value A and the global gain value B—i.e., A*B*Iref, with A varying between 0 and 255, and B varying between 0 and 2. Thus, assuming Iref=100 nA, node 390 may therefore include values ranging from 0 to 51 µA.

Figure 11D:
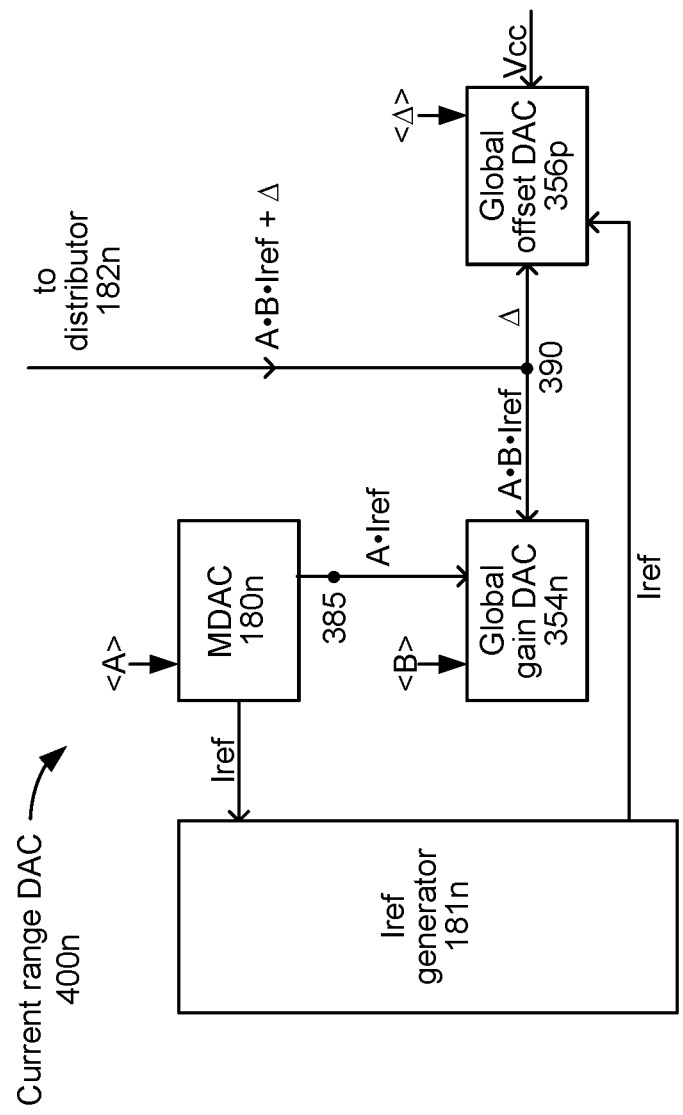
FIG. 11D shows an alternative design for the current range DAC circuitry.

Note that the global gain DAC 354n and the master DAC 180n could be flipped with the current range DAC 400n, with the MDAC 180n outputting its current to the global gain DAC 354n, as shown in FIG. 11D. In this example, the MDAC 180 would receive Iref and amplify (A*Iref) it at node 385. This current could then be input to the global gain DAC 354n, which would amplify (by B) this current further to produce A*B*Iref at node 390.

The global offset DAC 356n comprises in this example a binary-weighted DAC, having an input leg which receives Iref at its input transistor 378 which forms current mirrors with transistors 370 in the output legs of the DAC 356n. (Again, cascode transistors such as 376 and 372 are not important to understanding circuit operation). In this example, the transistors 378 and 370 are sized the same, but there is only one transistor 378 provided in the input leg, and an exponentially-increasing number of paralleled transistors 370 in the five output legs (10, 20, 40, 80, and 160). This produces current of 10*Iref, 20*Iref, 40*Iref, 80*Iref, and 160*Iref in each of the output legs when selected by global offset control signals $\Delta\_0$ through $\Delta\_4$ carried by bus $<\Delta>$ (FIG. 11B). Through this arrangement, the global offset DAC 356n can subtract currents of magnitudes from 0 to 310*Iref from node 390 depending on which global offset control signals $\Delta\_i$ are asserted, as summarized in FIG. 11E. Again, assuming Iref=100 nA, global offset DAC 356n can produce currents from $\Delta$=0 to 31 µA from node 390. Note that if global offset DAC 356n does not need to impart a special offset (i.e., $\Delta$=0), all of the global offset control signals ($\Delta\_4$ to $\Delta\_0$) will be deasserted. In combination with the Master DAC 180n then, a current is produced at node 390 that equals A*B*Iref+$\Delta$.

Notice in this example that there is no corresponding global offset DAC to add current to node 390 (compare 306p and 306n in FIG. 10C). This is because such functionality is not necessary to providing current within a therapeutic range, as discussed earlier with respect to FIG. 11A (401b). That being said, a corresponding global offset DAC providing an opposite polarity current to node 390 could also be added, which might be useful for other reasons.

The resulting current A*B*Iref+A at node 390 is provided to the distributor 182n, which ultimately distributes this current to each of the NDACs. As discussed earlier, this distribution scheme may or may not include calibrations circuits such as 302n1 servicing NDAC1. If such calibration circuits are used, they may calibrate the input A*B*Iref+$\Delta$ with electrode-specific gains G and offsets O, as described earlier. This potentially results, as shown in FIG. 11B, in sending individualized currents to the NDACs of the form G(A*B*Iref+$\Delta$)+O.

FIG. 11F returns to the example discussed earlier in FIG. 11A (401b), and explains how the foregoing circuitry can be used to limit the electrode currents the DAC circuitry 172 produces to a particular therapeutic range, in this example from 3.8 to 12 mA. For simplicity, it is assumed that the electrodes currents in this case are positive, and thus handled by PDAC side circuitry, and hence by global gain DAC 354p and global offset DAC 356p (see FIG. 11G).

As before, it is useful to first consider the global offset $\Delta$ the global offset DAC 365p should produce. An electrode current offset of 3.8 mA is required, and if it is assumed that the PDACs amplify input currents A*B*Iref by 1000, a global offset current $\Delta$=3.8 µA is required. Referring to FIG. 11E, the closest current to this value the DAC 356p can produce is 4 µA (decimal 4), which is formed by asserting only global offset control signal $\Delta\_2$ ($\Delta\_4$, $\Delta\_3$, $\Delta\_1$, and $\Delta\_0$ are not asserted) in the global offset DAC 356p. Next, the global gain value B to be provided by global gain DAC 354p is assessed. As before, normal operation of the DAC circuitry 172 (B=1) imparts a nominal slope of 0.1 (25.5/255). By contrast, the desired slope given the therapuetic range from (A,I) (1, 3.8 mA) to (255, 12 mA) is 0.0323. A*Iref thus requires a global gain B=0.323 (0.0323/0.1). Referring again to FIG. 11E, the closest gain value the global gain DAC 354p can produce is 0.325 (decimal 26), which is produced by asserting only 26 of the global gain control signals B_i (e.g., B_25 to B_0) in the global gain DAC 354p.

Figure 11G:
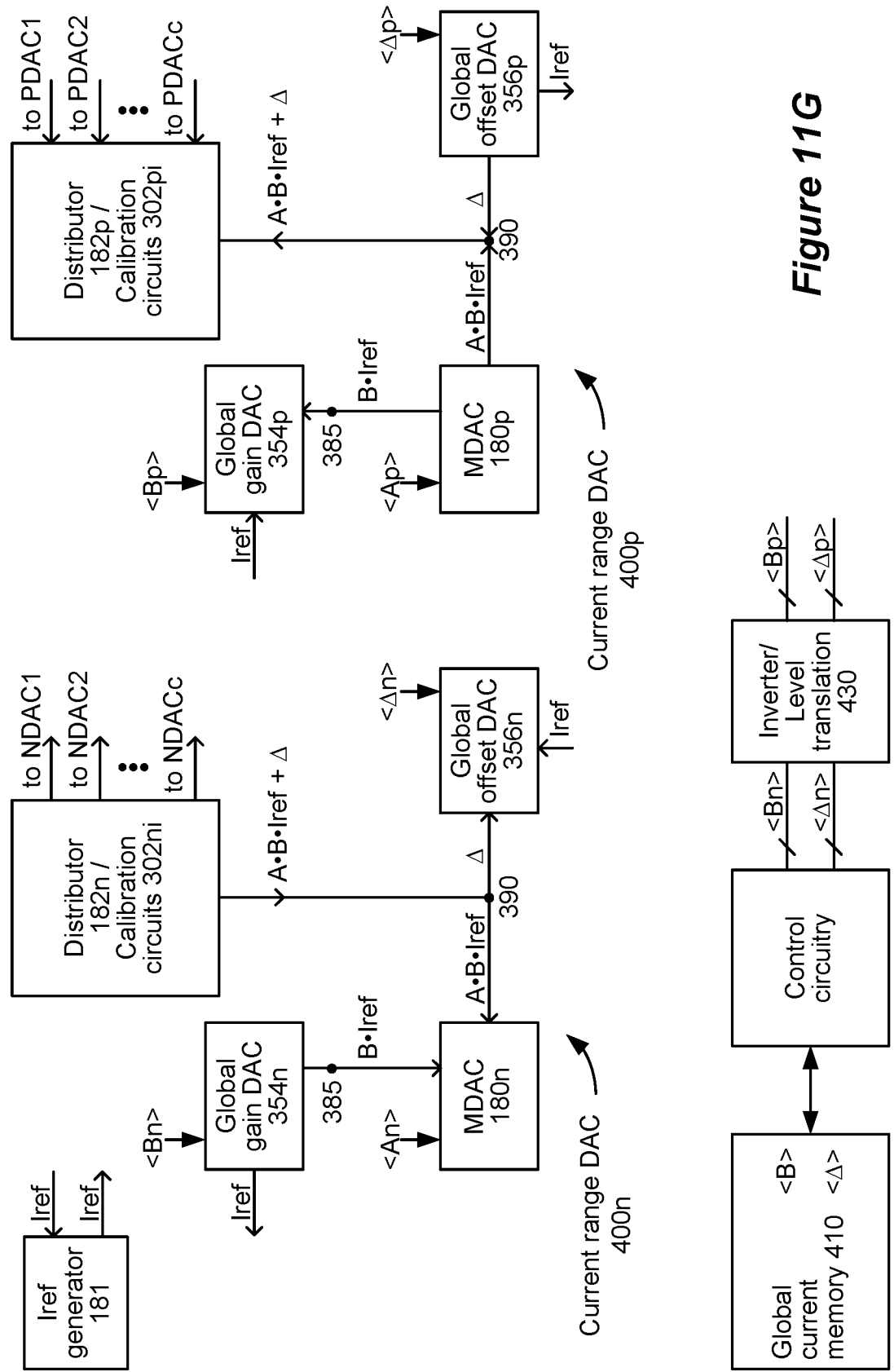
FIGS. 11G and 11H show different manners of implementing the current range DAC circuitry.

FIG. 11G discusses other implementation details, and in particular shows how the current range DAC 400n on the NDAC side can be duplicated (with polarities changes) as current range DAC 400p on the PDAC side of the DAC circuitry 172. As such, there may be separate global gain DACs 354n and 354p, and separate global offset DACs 356n and 356p on both sides of the circuitry. This is similar to the master DAC, which as noted earlier can be duplicated on the NDAC (180n) and PDAC (180p) sides (see FIGS. 7A & 7B). A global current memory 410 can store values for the global gain (B) and the global offset (A), as reflected by control signals <B> and <A>, which relevant control circuitry in the ASIC 160 (such as the Pulse Definition Circuit (PDC) (FIG. 8A) or the microcontroller block 150 (FIG. 4B) can read. Much like the amplitude value A provided to the master DACs 180n/p, the values for the global gain B and global offset $\Delta$ are preferably the same on both the NDAC side and the PDAC side to ensure that electrode currents are of uniform magnitudes regardless of polarity. Even though the global gain B and global offset $\Delta$ are preferably the same, these control signals will require inversion given the different polarities of the transistors used on the NDAC and PDAC sides, with inverter circuitry 430 used to form the control signals for these sides (<Bn>, <$\Delta$n>, <Bp> and <$\Delta$p>). Such inverter circuitry 430 may also involve level translation of the control signals as appropriate for the power supply domain (Vcc/GND or VH/Vssh) in which they will operate. Inversion and level translation is discussed later with respect to FIGS. 16A-16D. While it is preferred that the global gain values Ba and Bp, and the global offset values $\Delta$n and $\Delta$p are equal on the NDAC and PDAC sides, they could also be different. Thus, control signals <Bn> may be set independent of <Bp>, and control signals <$\Delta$n> may be set independent of <$\Delta$p>. While this alternative isn't shown in FIG. 11G, it would allow the global gain and offset to be set differently on the NDAC and PDAC sides of the circuitry.

Figure 11H:
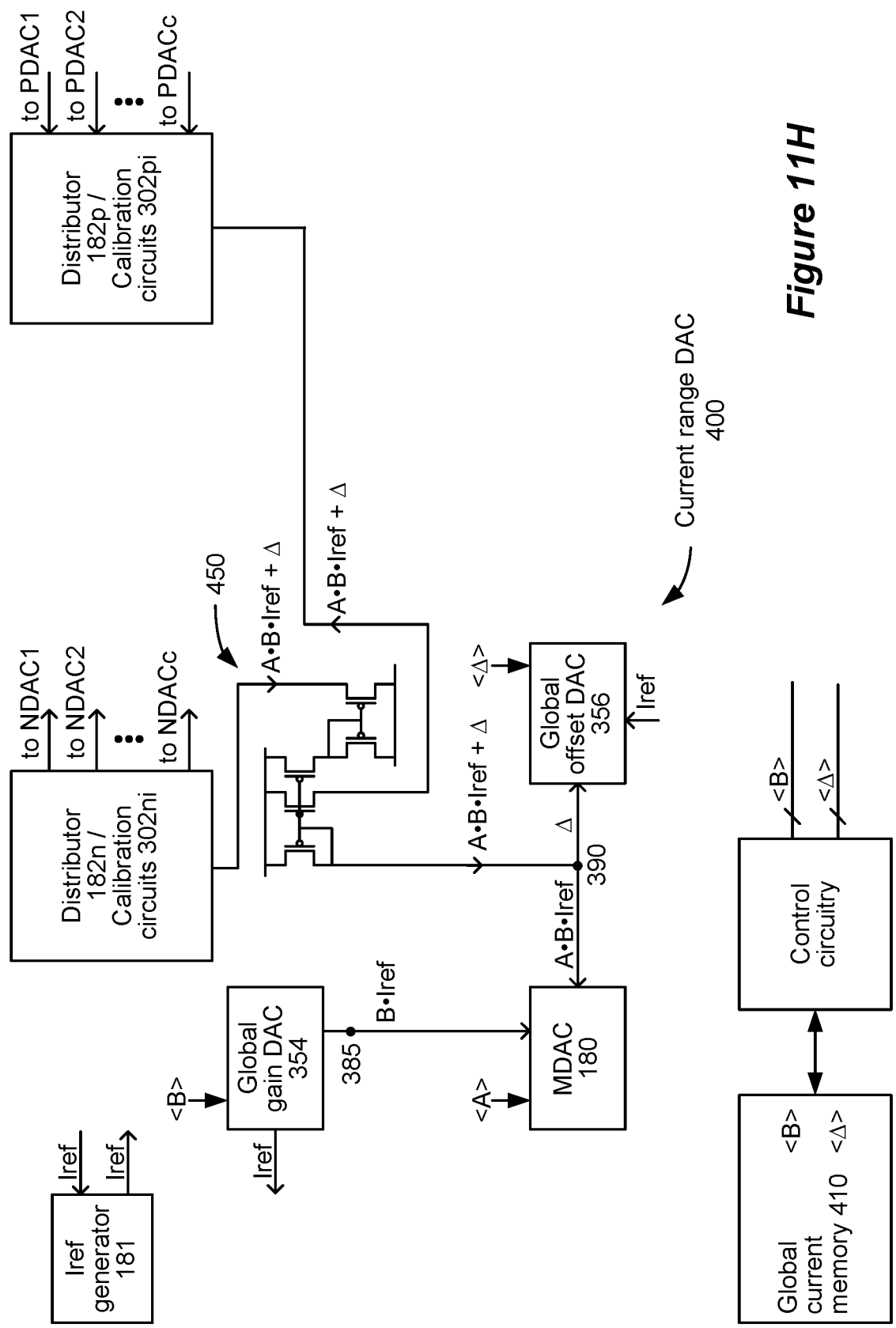

FIG. 11H shows another alternative in which a single current range DAC 400 is used to service both the NDAC and PDAC sides of the DAC circuitry. In this example, there is only one MDAC 180, global gain DAC 354, and global offset DAC 356, each being control by control signals <A>, <B>, and <A>. As noted earlier, this produces a current A*B*Iref+$\Delta$ at node 390. This current is in turn provided to a polarity circuit 450 that produces the current with this magnitude and with the proper polarity to be received by distributor 182n on the NDAC side and distributor 182p on the PDAC side as shown. Polarity circuit 450 can comprise current mirror circuitry as explained and described elsewhere in this disclosure, or may be made as shown in U.S. Patent Application Publication 2018/0071511. The example of FIG. 11H is simpler and requires less area on the ASIC 160 because the current range DAC circuitry 400 does not need to be repeated on the NDAC and PDAC sides of the circuitry, and because the control signals do not need to be duplicated (e.g., inverted or level translated).

Unlike electrode calibration (FIGS. 10A-10G), it is envisioned that use and programming of the global gain and global offset features will occur after manufacture and once the IPG is implanted in a patient, because only then can desired therapeutic ranges of electrode currents be established. In this regard, it particularly useful that a user (e.g., a clinician or patient, as opposed to the manufacture) be able to access the global gain and offset features described. This is described in FIG. 11I. Shown is a graphical user interface (GUI) 420 that accompanies an external device that wirelessly communicates with the IPG (e.g., a clinician's programmer, or a patient remote controller). Once a therapeutic range of currents (maximum and minimum values) has been established for the patient, this range (e.g., maximum and minimum values) may be entered into the GUI 420 as shown. Range information such as maximum and minimum currents may not necessary be entered manually, but may also autopopulate in the GUI 420, as discussed further below. A global gain and offset algorithm 440 operable in the external device may then compute the global gain (B) and global offset (A) values, and the relevant control signals <B> and <A>, needed to provide for control over the entire range of amplitude values, and to provide those to the DAC circuit 172 in the IPG (for storage in global current memory 410). Alternatively, the algorithm 440 can operate in the IPG, with the external device transmitting information regarding the therapeutic range to the IPG, and with the IPG determining and storing B and A as necessary for that range. The global gain and offset algorithm 440 can undertake steps such as those discussed above with reference to FIG. 11F to determine B and A. The GUI 420 may also display the current resolution that results (0.0322 mA/per amplitude value step) after the DAC has been adjusted with global gains and offset values B and Δ.

The GUI 420 may also allow the current to be adjusted within the therapeutic range established by B and A. Thus, the GUI 420 can show an amplitude I (e.g., 5.9 mA) to which the IPG is presently programmed, and can provide one or more inputs 460 to allow the amplitude to be increased (+) or decreased (−). Other GUI schemes can be used to adjust the amplitude, such as those described in U.S. Patent Application Publication 2021/0299457. The amplitude within the therapeutic range can also be expressed more qualitatively. For example, the amplitude may be expressed in terms of a percentage (e.g., 26%), which indicates for the user a general intensity of the amplitude within the therapeutic range (e.g., 5.9 mA is 26% of the way between 3.8 mA and 12 mA). Providing a more qualitative indication of the amplitude may be more intuitive for some users (e.g., patients), who may not understand or care about the precise current stimulation therapy is providing. Other GUI schemes (bars, numbers, etc.) may be used to qualitatively indicate a presently-programmed amplitude within the therapeutic range.

The ability to constrain the current amplitude to a desired therapeutic range using the global gain and offset features is further useful in providing different types of stimulation therapies. For example, it is known that stimulation therapy can be supra-perception or sub-perception. Supra-perception therapy can be felt by the patient as paresthesia (e.g., tingling or pickling), and is typically provided at higher amplitudes. Sub-perception therapy provides symptomatic relief without being felt by the patient, and is typically provided at lower amplitudes. A user or clinician can determine a perception threshold (pth) for the amplitude at the boundary between these two stimulation regimes, e.g., a lowest amplitude that the patient can feel. Similarly, a user or clinician can establish a discomfort threshold (dth) for the amplitude, which comprises a highest amplitude the patient can tolerate before discomfort or side effects are problematic. Both of these thresholds can be determined by setting the amplitude to zero and slowly increasing the amplitude until the stimulation can be felt (pth) and then further increasing the amplitude to the point of discomfort.

Figure 11I:
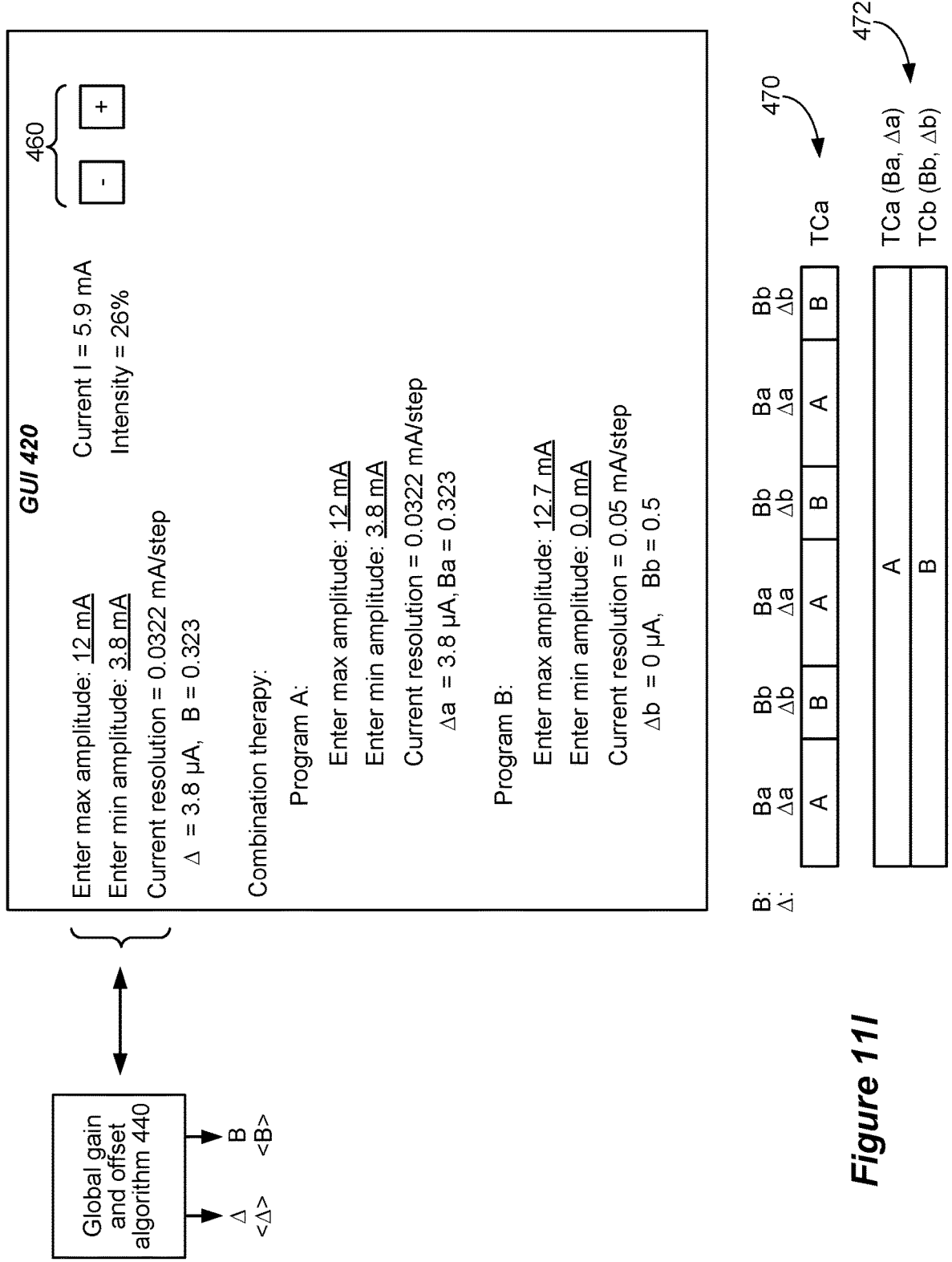
FIG. 11I shows the user interface of an external device in communication with an IPG having current range DAC circuitry, including inputs that can be used to program the current range DAC circuitry to set electrode currents within desired therapeutic ranges.

If pth and dth are determined in this or other manners, they may be entered or autopopulated into the GUI 420 to help set the therapeutic range, and hence the type of therapy the patient will receive. For example, if it is desired that the patient only receive supra-perception therapy, pth may be entered as the minimum current amplitude for the therapeutic range, and dth may be entered as the maximum current for the therapeutic range. Global gain and offset B and A can then be calculated, allowing the user to only select supra-perception current amplitudes between pth and dth (with lower resolution, and using the full range of amplitude steps). If it is desired that the patient only receive sub-perception therapy, pth may be entered as the maximum current amplitude for the therapeutic range. The minimum current amplitude may be set to zero, or somewhere between 0 and pth indicative of the low end of therapeutic effectiveness. Again, the global gain and offset B and Δ can then be calculated, allowing the user to only select sub-perception current amplitudes less than pth (again, with lower resolution, and using the full range of amplitude steps). The GUI 420 of FIG. 11I also shows application of the disclosed global gain and offset features in combination therapy. In combination therapy, the patient may receive different stimulation waveforms, such as defined by Programs A and B. Therapeutic ranges can be defined for each of these programs, with global gain and offset values calculated accordingly for each (Ba and Aa, and Bb and Ab). Combination therapy can provide both Programs A and B in an interleaved (time-multiplexed) fashion 470, or concurrently 472, as shown at the bottom of FIG. 11I. When interleaved, stimulation can be provided in a single timing channel TCa, with the programs A and B, and their associated global values B and Δ, being updated within the timing channel TCa at appropriate times. This allows the amplitude to be adjusted (e.g., at 26% intensity) for both programs A and B as discussed above. When Programs A and B are applied concurrently (472), they are preferably applied in different timing channels TCa and TCb, with global values B and Δ set in each of the timing channels. Timing channels are discussed further with respect to FIGS. 14A-14F, but in this example amplitude Aa and Ab in these different timing channels can be independently adjusted, with amplitude Aa constrained by Ba and Δa, and with Ab constrained by Bb and Δb.

Figure 12A:
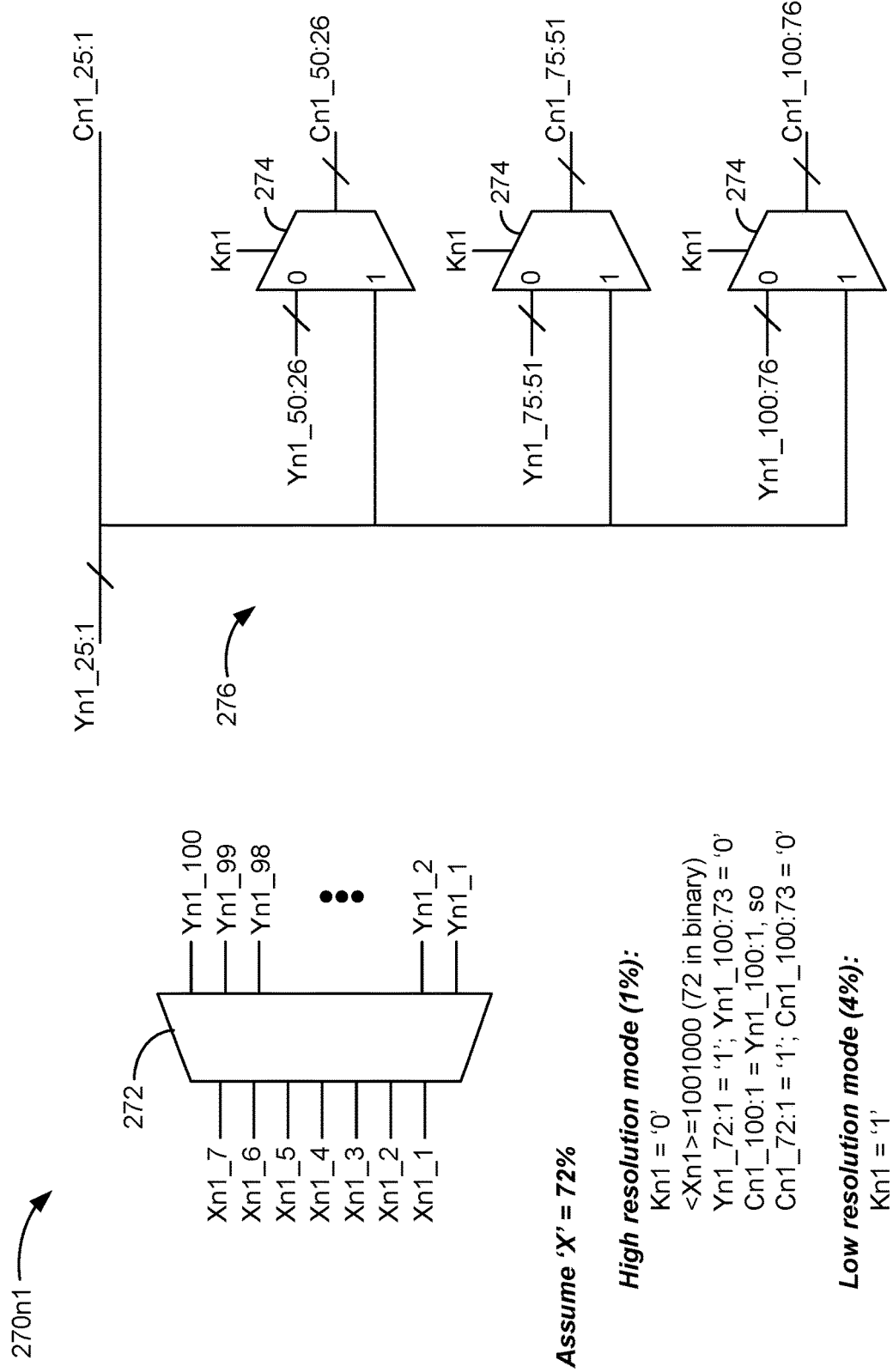
FIGS. 12A and 12B show logic circuitry for generating the switch control signals for the branches in the PDACs and NDACs, which logic circuitry is controlled in accordance with the resolution control signals.

To review, the magnitude of the current provided by a PDACi or NDACi to its associated electrode node Ei' is set by controlling the magnitude of 'A' from the master DAC 180, and by controlling switch control signals <Ci> to add or remove active branches from the DAC. Control signals <Ci> are generated from the percentage bus <Xpi> or <Xni> and resolution control signal Kpi or Kni sent to each PDACi and NDACi by the PDC (FIG. 8A). The logic circuitry 270 used to convert <Xni> and Kni to <Cni> is shown in FIG. 12A. The logic circuitry 270 is shown specifically for NDAC1 (207n1), but each PDAC and NDAC would have similar circuitry 270. Logic circuitry 270 for each PDAC and NDAC can be considered part of that PDAC or NDAC.

FIG. 12A includes logic circuitry 272, preferably a thermometer decoder, which receives the percentage bus for NDAC1, <Xn1>, shown as 7 bits Xn1_7:1. Thermometer decoder 272 will assert a number of intermediate signals <Yn1>, shown as 100 bits Yn1_100:1. These intermediate signals <Yn1> are then input to a multiplexer stage 276 that includes a number of different multiplexers 274, which output the switch control signals Cn1_100:1 received by NDAC1 and described earlier (FIG. 9B). Notice that the multiplexers 274 are controlled by the resolution control signal Kn1, which by way of review sets an amount by which each PDAC or NDAC's percentage 'X' can be adjusted. Specifically, Kn1 controls whether the percentage 'X' for NDAC1 will be variable in 1% increments in a high resolution mode, or 4% increments in a low resolution mode.

Operation in a high resolution mode is described first, and using an example in which NDAC1 is to receive 72% of the total cathodic amplitude 'A'. (Although not shown, some other electrode(s)' NDAC(s) would be responsible for producing the remaining 28% of the total cathodic current). In high resolution mode, the resolution control for NDAC1, Kn1, would be set to '0'. Further, the PDC, knowing that high resolution mode is desired for NDAC1, would set the percentage signals for NDAC1, <Xn1>, to the desired percentage of 72 in binary, or '1001000.' (Seven bits for <Xn1> are required to encode percentages from 1 to 100). Thermometer decoder 272 would in turn assert intermediate control signals Yn1_72:1 ('1'), and unassert all other outputs Yn1_100-73 ('0').

Intermediate signals <Yn1> are passed to the multiplexer stage 276. Notice that the least-significant 25 bits, Yn1_25:1, are simply passed as the least-significant 25 switch control signal bits, Cn1_25:1. Thus, for 'X'=72%, all of Cn1_25:1 would be asserted. When Kn1='0', the multiplexers 274 would also pass different groups of the intermediate control signals Yn1 to their corresponding switch control signals, i.e., Cn1_50:26 is set to Yn1_50:26, Cn1_75:51 is set to Yn1_75:51, and Cn1_100:76 is set to Yn1_100:76. Thus, for 'X'=72%, multiplexers 274 would assert Cn1_72:26, and unassert Cn1_100:73.

In low resolution mode, the resolution control for NDAC1, Kn1, would be set to '1'. Further, the PDC, knowing that low resolution mode is desired for NDAC1, would divide the desired percentage by four, i.e., 72/4=18. The PDC would then set the percentage signals for NDAC1, <Xn1>, to 18 in binary, or 'xx10010.' (Because a maximum value of 100/4=25 is required in low resolution mode, only five of the seven bits of <Xn1> are required; in effect most-significant bits Xn1_7 and Xn1_6 become "don't care" values). Thermometer decoder 272 would in turn assert intermediate control signals Yn1_18:1 ('1'), and unassert all other outputs Yn1_100-19 ('0').

Intermediate signals <Yn1> are passed to the multiplexer stage 276. Again, the least-significant 25 bits, Yn1_25:1, are simply passed as the least-significant 25 switch control signal bits, Cn1_25:1. Thus, in low resolution mode, for 'X'=72%, all of Cn1_18:1 would be asserted, and Cn_25:19 would be unasserted. Because Kn1='1', the multiplexers 274 would pass these same the least-significant 25 bits, Yn1_25:1, to the remaining groups of the switch control signals. Thus, Cn1_50:26, Cn1_75:51, and Cn1_100:76 are all set to Yn1_25:1. Thus, for 'X'=72%, multiplexers 274 would assert Cn1_18:1, Cn1_43:26, Cn1_68:51, and Cn1_93:76, and unassert Cn1_25:19, Cn1_50:44, Cn1_75:69, and Cn1_100:94.

Figure 12B:
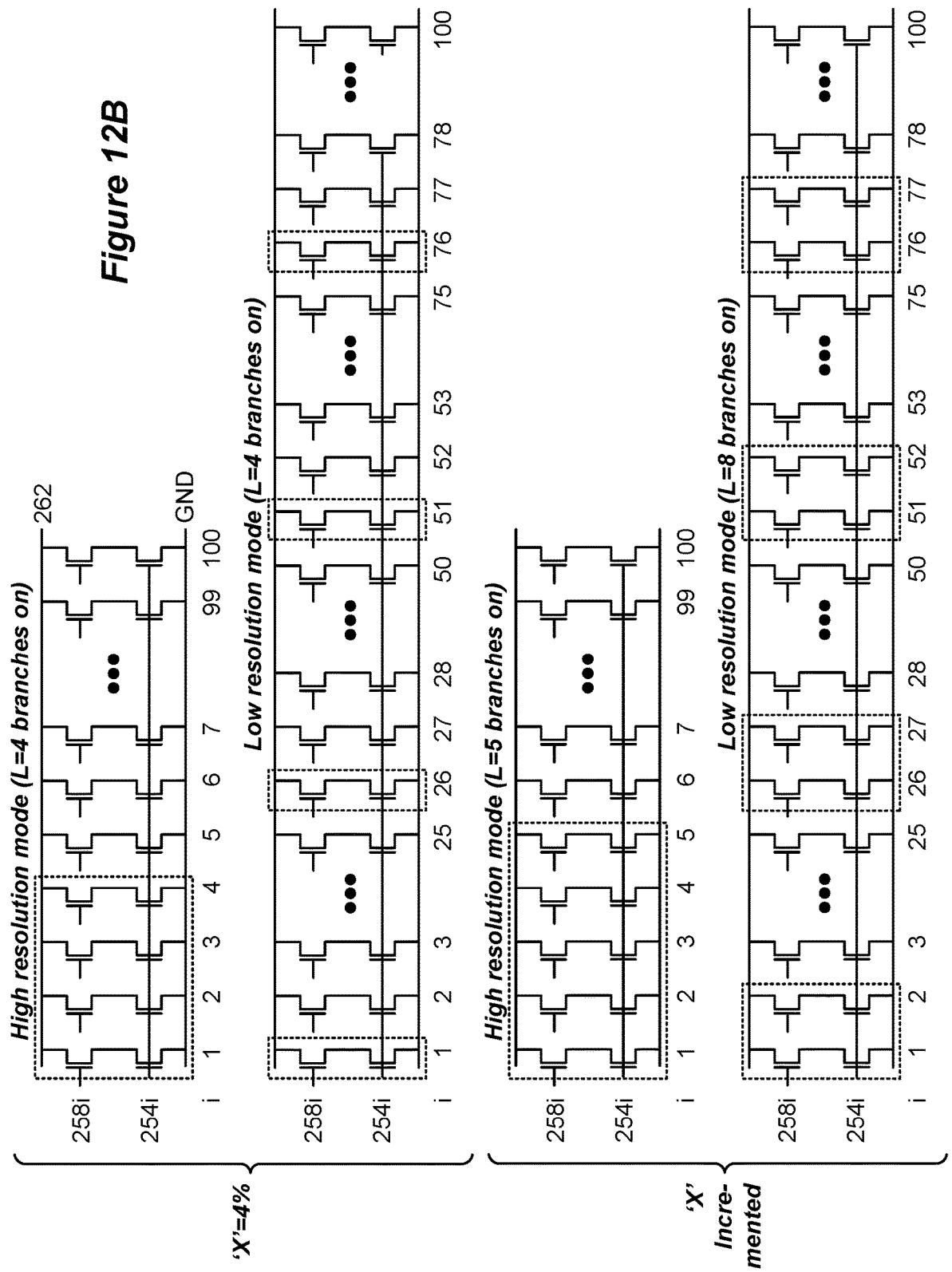

In either the high or low resolution mode, the current produced by the DAC is the same, although the particular branches turned on in the DAC can differ. This is shown in FIG. 12B for a generic NDAC, although the PDAC would be similar. The top of FIG. 12B shows a simple case in which 'X'=4%. Both high and low resolution modes are shown, with active branches in the NDAC enclosed by dotted lines. Through operation of the logic circuitry 270 of FIG. 12A, in the high resolution mode, intermediate signals Y4:1 would be asserted, meaning switch control signals C4:1 would likewise be asserted, thus turning on the first four branches in the NDAC. However, in the low resolution mode, only intermediate signal Y1 would be asserted. Operation of the multiplexer stage 276 would accordingly assert C1, C26, C51, and C76. Thus, four (different) branches of the NDAC (PDAC) are turned on. Because four branches are turned on for each resolution, the NDAC (PDAC) in either case will sink (source) the same amount of current—i.e., 4% of the total cathodic (anodic) amplitude 'A'.

The resolution mode affects how the percentage 'X' can be incremented or decremented in a DAC, which is constrained by the number of branches that the logic circuitry 270 can turn on in each mode. Assume for example that 'X' is incremented from 4% in FIG. 12B. If the PDC specifies that the DAC at issue operates in the high resolution mode, incrementing 'X' means that X will now equal 5%, because 'X' can be incremented in 1% steps. Incrementing 'X' in this fashion, and through operation of logic circuitry 270, will assert intermediate signals Y5:1, and thus switch control signals C5:1, thus turning on the first five branches of the DAC, and producing 5% of 'A' from the DAC as shown at the bottom of FIG. 12B. By contrast, if the PDC specifies that the DAC at issue operates in the low resolution mode, incrementing 'X' means that X will now equal 8%, because 'X' will be incremented in 4% steps. Incrementing 'X' in this fashion, and through operation of logic circuitry 270, will assert intermediate signals Y2:1, and thus switch control signals C1, C2, C26, C27, C51, C52, C76, and C77 will be asserted, turning on eight branches of the DAC, and producing 8% of 'A' from the DAC.

In effect, in the depicted example, in the high resolution mode, each of the DAC's branches are asserted/unasserted one at a time when 'X' is incremented/decremented, and in physical order in the DAC. In the high resolution mode, the logic circuitry 270 in effect ties switch control signals Ci, C(i+25), C(i+50), and C(i+75) together, thus permitting only groups of 4 branches (in physically different locations) to be chosen. However, it should be noted that which of the physical branches are chosen will depend on the layout of the DAC. For example, if the switch control signals C100:1 are not sent to sequentially physical branches in the DAC as in the illustrated examples, different physical branches would be selected to contribute to the current the DAC produces.

It should be noted that the improved DAC circuitry 172 can be extended to allow percentage 'X' to be changed with more than two resolutions. For example, FIG. 12C shows a modification to allow percentage 'X' to be adjusted in a high resolution mode (in 1% percent increments), a medium resolution mode (in 2% increments), and in a low resolution mode (in 4% increments). In this modification, resolution control signals comprise a bus <Kn1> able to indicate operation in high resolution mode (when <Kn1>='00'=0), in medium resolution mode (when <Kn1>='01'=1), and in low resolution mode (when <Kn1>='10'=2). Logic circuitry 270 includes a first multiplexer stage 276 essentially similar to that described earlier, except that it is not enabled in the medium resolution mode. A second multiplexer stage 277 is enabled only in the medium resolution mode (when <Kn1>=1). In this mode, PDC would take the desired percentage (72%), divide it by two (36), and assert this value in binary on percentage control signals <Xn1>, i.e., 'x100100.' Thermometer decoder 272 (FIG. 12A) would assert intermediate signals Y36:1, which multiplexer 278 in second multiplexer stage 277 would pass to both C36:1 and C86:51. In effect then, in the medium resolution mode, DAC branches would be asserted two at a time (C1 and C51, C2 and C52, etc.), thus providing 2% increments of amplitude 'A' to be output by the DAC. This is just one example in which a multi-resolution mode could be implemented, and other examples are possible.

As illustrated to this point, it is preferred that each PDAC and NDAC be provided its own resolution control signals, i.e., Kp1, Kn1, Kp2, Kn2, etc., thus allowing for independent resolution control of each PDAC and NDAC. However, in other examples, a single resolution control signal K could be used to control the resolution of all PDACs and NDACs. Alternatively, a single resolution signal could be provided to each PDAC/NDAC pair dedicated to a particular electrode—e.g., Kp1 and Kn1 could comprise a single control signal Kl.

Figure 13A:
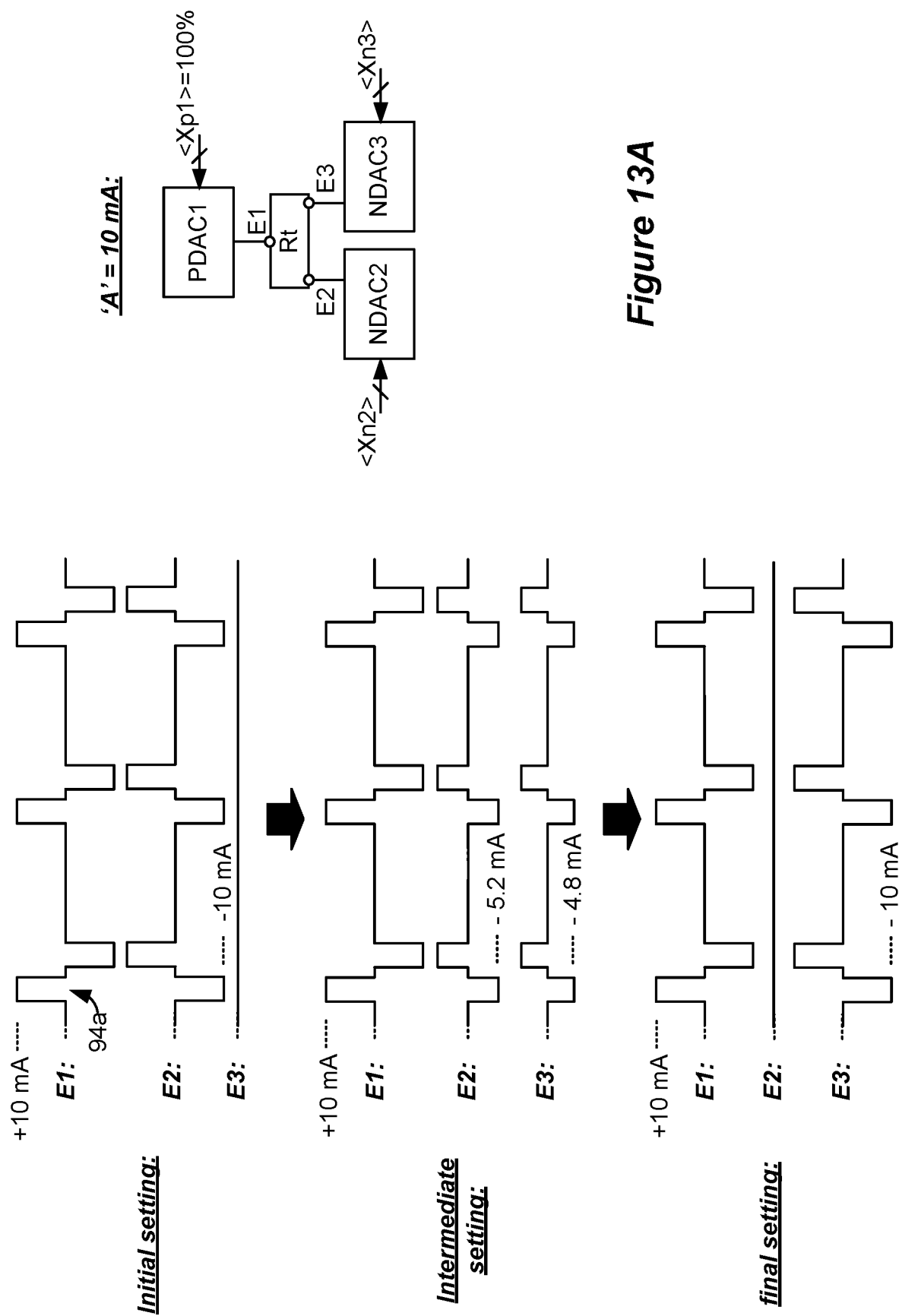
FIG. 13A shows use of the improved DAC circuitry to steer a current between electrodes in a timing channel, with FIG. 13B showing steering in a high resolution mode, and FIG. 13C showing steering in a low resolution mode.

As mentioned above, the percentage busses <X> provide a convenient way to "steer" current between different electrodes. Steering involves moving some portion of anodic current between two or more electrodes, or moving some portion of cathodic current between two or more electrodes. An example of current steering is shown in FIG. 13A, which involves use of electrode E1 as an anode, and electrodes E2 and E3 as cathodes (during first pulse phases 94a). In this example, cathodic current (−10 mA) is steered from E2 to E3 in gradual increments: initially, the entirety of the cathodic current is placed on E2, but eventually at the end of steering the entirety of the cathodic current is placed on E3. An intermediate setting is shown during the steering process at which the cathodic current at electrodes E2 and E3 are roughly equal (−5.2 mA and −4.8 mA). In this example, the anodic current issued from E1 stays constant (+10 mA), but anodic current may also be steered to and from different electrodes in more complicated examples.

Steering current between electrodes in small increments is a desirable use model, particularly during fitting of the IPG 10 to a particular patient. This because it may not initially be known what electrodes should be chosen for stimulation to relieve a patient's symptoms (e.g., pain). Gradually moving current between electrodes to determine which electrodes should be active to provide therapy, and in what proportions, may be more comfortable and less dangerous for the patient. For example, if all of the cathodic current is moved instantaneously from E2 to E3 in the example of FIG. 13A (from the initial setting to the final setting), the effect may be jarring on the patient. Moving current in gradual increments reduces this risk, and allows finer tuning of therapy as source current can be shared by one or more selected anode electrodes, and sink current can be shared by one or more selected cathode electrodes. See U.S. Pat. No. 7,890,182, discussing this issue in further detail. Moving current in the manner shown can be performed by a clinician programmer running IPG control software in communication with a patient's IPG 10. Alternatively, current may also be movable between electrodes by the patient using a hand-holdable external controller. Alternatively, the current may be moved automatically by the IPG 10, i.e., by the microcontroller block 150 or the PDC (see FIG. 8A).

FIGS. 13B and 13C shows how steering current between the electrodes E2 and E3 of FIG. 13A can be achieved using DAC circuitry 172, in high and low resolution modes respectively. In both cases, amplitude bus <A> sets a value 'A' of 10 mA—the total anodic and cathodic current required. Notice that percentage bus <Xp1>=100%, because all anodic current will be provided by PDAC1 associated with electrode E1. Bus <Xn1>=0%, because E1 is not acting as a cathode, and thus NDAC1 will be inactive. Likewise busses <Xp2> and <Xp3>=0% because electrodes E2 and E3 are not acting as anodes, and thus PDAC2 and PDAC3 will be inactive. Finally, all other percentage busses (<Xp4>, <Xn4>, <Xp5>, <Xn5>, . . . , <Xp16>, <Xn16>, <Xpc>, Xnc>) are set to 0%, because electrodes E4-E16 and Ec are not selected for stimulation, and hence their PDACs and NDACs are inactive.

FIG. 13B illustrates steering in the high resolution mode. Thus, the resolution control signals for electrode E2 and E3's NDACs—Kn2 and Kn3—are set to '0', and PDC will issue a percentage signals <Xn2> and <Xn3> from 0 to 100 in 1% increments (using all of bits Xn_7:1). Each 1% adjustment occurs at sequential times t0, t1, t2, . . . , t100, which adjustments can again be made using a clinician programmer or patient external controller, and wirelessly transmitted to the IPG 10. At time t0, PDC sets <Xn2> to 100%, and thus logic circuitry 270 (FIG. 12A) will assert all 100 branches in NDAC2 (Cn2_100:1 are asserted) and so electrode E2 outputs 100% of 'A' (−10 mA); PDC sets <Xn3> to 0%, and thus no branches are asserted in NDAC3 (Cn3_100:1 are unasserted) and so electrode E3 outputs 0% of 'A' (0 mA). At time t1, where a 1% increment of 'A' is moved from E2 to E3, PDC sets <Xn2> to 99%, and 99 branches in NDAC2 are asserted (Cn2_99:1) and so electrode E2 outputs 99% of 'A' (−9.9 mA); PDC sets <Xn3> to 1%, and thus one branch in NDAC3 is asserted (Cn3_1) and so electrode E3 outputs 1% of 'A' (−0.1 mA). This continues as shown in FIG. 13B until, at time t100, PDC sets <Xn2> to 0%, and thus no branches in NDAC2 are asserted (Cn2_100:1 are unasserted) and so electrode E2 outputs 0% of 'A' (0 mA); PDC sets <Xn3> to 100%, and thus all branches are asserted in NDAC3 (Cn3_100:1 are asserted) and so electrode E3 outputs 100% of 'A' (−10 mA). At this point, all cathodic current has been steered from electrode E2 to electrode E3.

FIG. 13C illustrates steering in the low resolution mode. Thus, the resolution control signals for electrode E2 and E3's NDACs—Kn2 and Kn3—are set to '1', and PDC will issue a percentage signals <Xn2> and <Xn3> from 0 to 25 (0% to 100%) in 4% increments (using only bits Xn_5:1). Each 4% adjustment occurs at sequential times t0, t1, t2, . . . , t25; notice that because the resolution is lower in FIG. 13C than in FIG. 13B, it takes less time (t100 versus t25) to completely steer the cathodic current from electrode E2 to electrode E3. At time t0, PDC sets <Xn2> to 25 (100%), and thus logic circuitry 270 (FIG. 12A) will assert all 100 branches in NDAC2 (Cn2_100:1 are asserted) and so electrode E2 outputs 100% of 'A' (−10 mA); PDC sets <Xn3> to 0%, and thus no branches are asserted in NDAC3 (Cn3_100:1 are unasserted) and so electrode E3 outputs 0% of 'A' (0 mA). At time t1, where a 4% increment of 'A' is moved from E2 to E3, PDC sets <Xn2> to 24 (96%), and 96 branches in NDAC2 are asserted (Cn2_99:76, 74:51, 49:26, 24:1) and so electrode E2 outputs 96% of 'A' (−9.6 mA); PDC sets <Xn3> to 1 (4%), and thus four branches in NDAC3 are asserted (Cn3_76, 51, 26, 1) and so electrode E3 outputs 4% of 'A' (−0.1 mA). This continues as shown in FIG. 13C until, at time t25, PDC sets <Xn2> to 0%, and thus no branches in NDAC2 are asserted (Cn2_100:1 are unasserted) and so electrode E2 outputs 0% of 'A' (0 mA); PDC sets <Xn3> to 25 (100%), and thus all branches are asserted in NDAC3 (Cn3_100:1 are asserted) and so electrode E3 outputs 100% of 'A' (−10 mA). At this point, all cathodic current has been steered from electrode E2 to electrode E3.

FIGS. 14A-14F show an alternative for DAC circuitry 172 in which a plurality of PDAC/NDAC pairs are dedicated to and able to provide a current at a particular electrode. In the example shown in FIG. 14A, there are two PDACs (PDACia, PDACib) and two NDACs (NDACia, NDACib) dedicated to each electrode node Ei'. While not strictly necessary, in the example depicted, each pair is dedicated to providing currents within a given timing channel. Thus, PDACia/NDACia source/sink current to/from electrode Ei in timing channel TCa, while PDACib/NDACib source/sink current to/from electrode Ei in timing channel TCb. The PDACs at a given electrode, and the NDACs at a given electrode, may be identical; for example, they may have the same number of branches as described earlier. Alternatively, the PDACs at a given electrode, and the NDACs at a given electrode, may be different; for example, they may have different number of branches and thus provide currents of different resolutions, as explained subsequently. In a preferred example, DAC circuitry 172 includes four PDAC/NDAC pairs at each electrode, with each pair providing currents in accordance with its own timing channel (e.g., TCa, TCb, TCc, and TCd), although this isn't illustrated in FIGS. 14A-14F for simplicity.

Figure 14A:
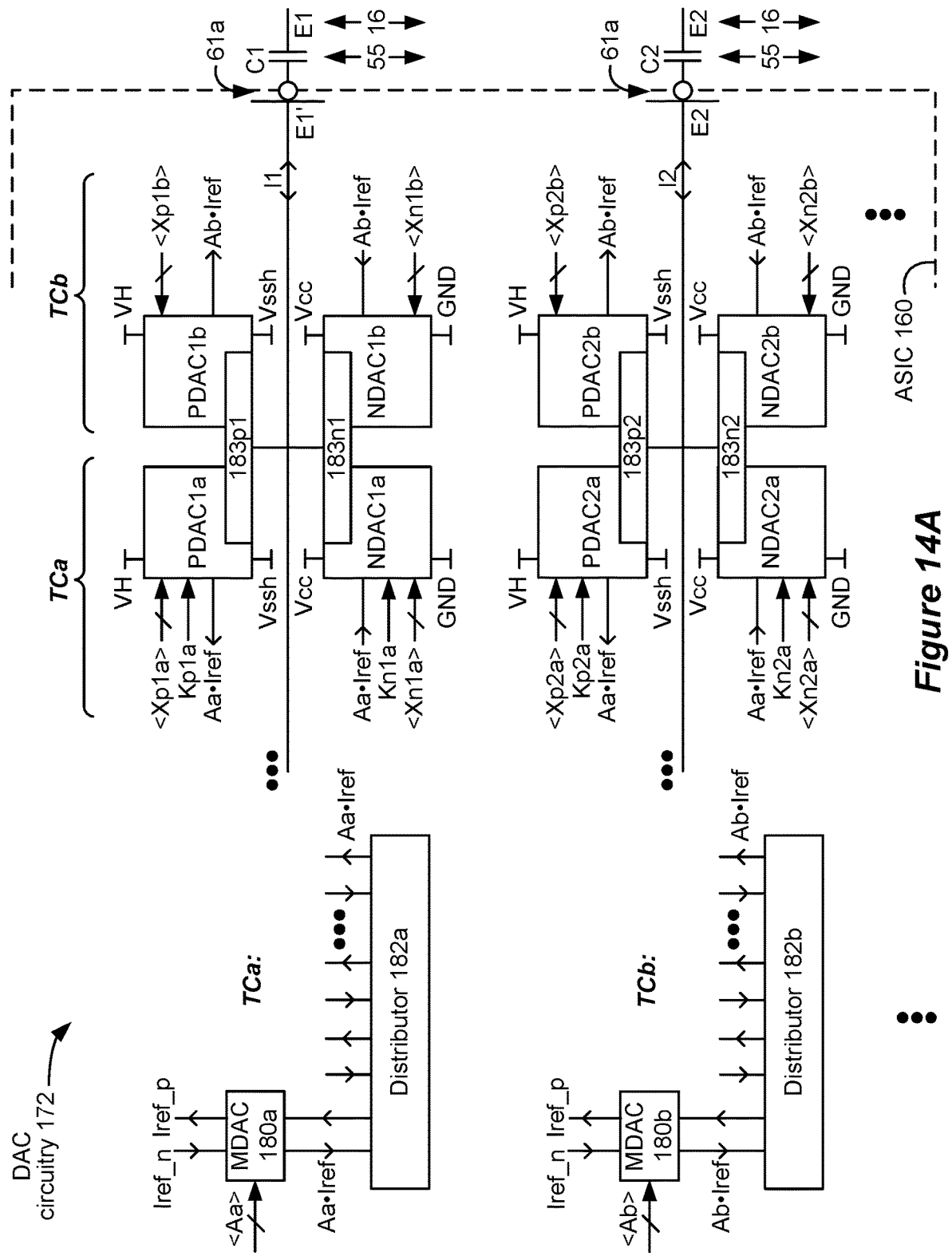
FIGS. 14A-14F show an alternative example of the improved DAC circuitry in which multiple PDAC/NDAC pairs are dedicated to each electrode, which pairs are preferably controlled in different timing channels.

DAC circuitry 172 in FIG. 14A further includes a master DAC and distributor that operate with each timing channel. For example, master DAC 180a and distributor 182a operate with timing channel TCa, while master DAC 180b and distributor 182b operate with timing channel TCb. Each master DAC 180 receives an amplitude bus that sets the total anodic and cathodic current of stimulation pulses in the relevant timing channel. Thus, master DAC 180a receives amplitude bus <Aa>, which sets a total amplitude of 'Aa' for pulses in timing channel TCa, while master DAC 180b receives amplitude bus <Ab>, which sets a total amplitude of 'Ab' for pulses in timing channel TCb. As before, each master DAC outputs an amplified version of a reference current, with its associated distributor providing that amplified current to PDACs and NDACs associated with that timing channel. Thus, master DAC 180a outputs amplified currents Aa*Iref, with distributor 182a providing those currents to PDAC1a, NDAC1a, PDAC2a, NDAC2a, etc., that operate within timing channel TCa. (Again, the amplified currents are of differing polarities depending whether they are sent to PDACs or NDACs, as explained earlier). Likewise, master DAC 180b outputs amplified currents Ab*Iref, with distributor 182b providing those currents to PDAC1b, NDAC1b, PDAC2b, NDAC2b, etc., that operate within timing channel TCb.

As shown in FIG. 14A, each of the PDACs at a given electrode node Ei' preferably share the same output circuitry 183pi, and each of the NDACs at that electrode preferably share the same output circuitry 183ni. This will be shown in more detail with respect to FIGS. 14D and 14E. Also, it should be noted that each PDAC and NDAC preferably has logic circuitry 270 (FIG. 12A) associated with it as described earlier, although this isn't shown in FIG. 14A for simplicity.

Each of the PDACs and NDACs operating in timing channel TCa receive percentage bus control signal <Xpia> and <Xnia>, which dictate the percentage of the total anodic and cathodic current 'Aa' that electrode Ei will receive. Each of the PDACs and NDACs operating in timing channel TCa also receive at least one resolution control signal Kpia and Knia. As before, these resolution control signals allow the PDACs and NDACs in timing channel TCa to operate in high or low resolution modes, thus allowing the percentage of 'Aa' that these PDACs or NDACs output to be changed in increments of 1% or 4% for example. Each of the PDACs and NDACs operating in timing channel TCb also receive percentage bus control signal <Xpib> and <Xnib>, which dictate the percentage of the total anodic and cathodic current 'Ab' that electrode Ei will receive. However, in this example, the PDACs and NDACs operating in timing channel TCb do not receive resolution control signal. This means that the resolution of these PDACs and NDACs is set and not adjustable. In a preferred example, the PDAC and NDACs in timing channel TCb are set to a low resolution mode, and thus the percentage of 'Ab' that these PDACs or NDACs can output is set to increments of 4% for example. However, resolution control signals may be used in timing channel TCb as well.

Figure 14B:
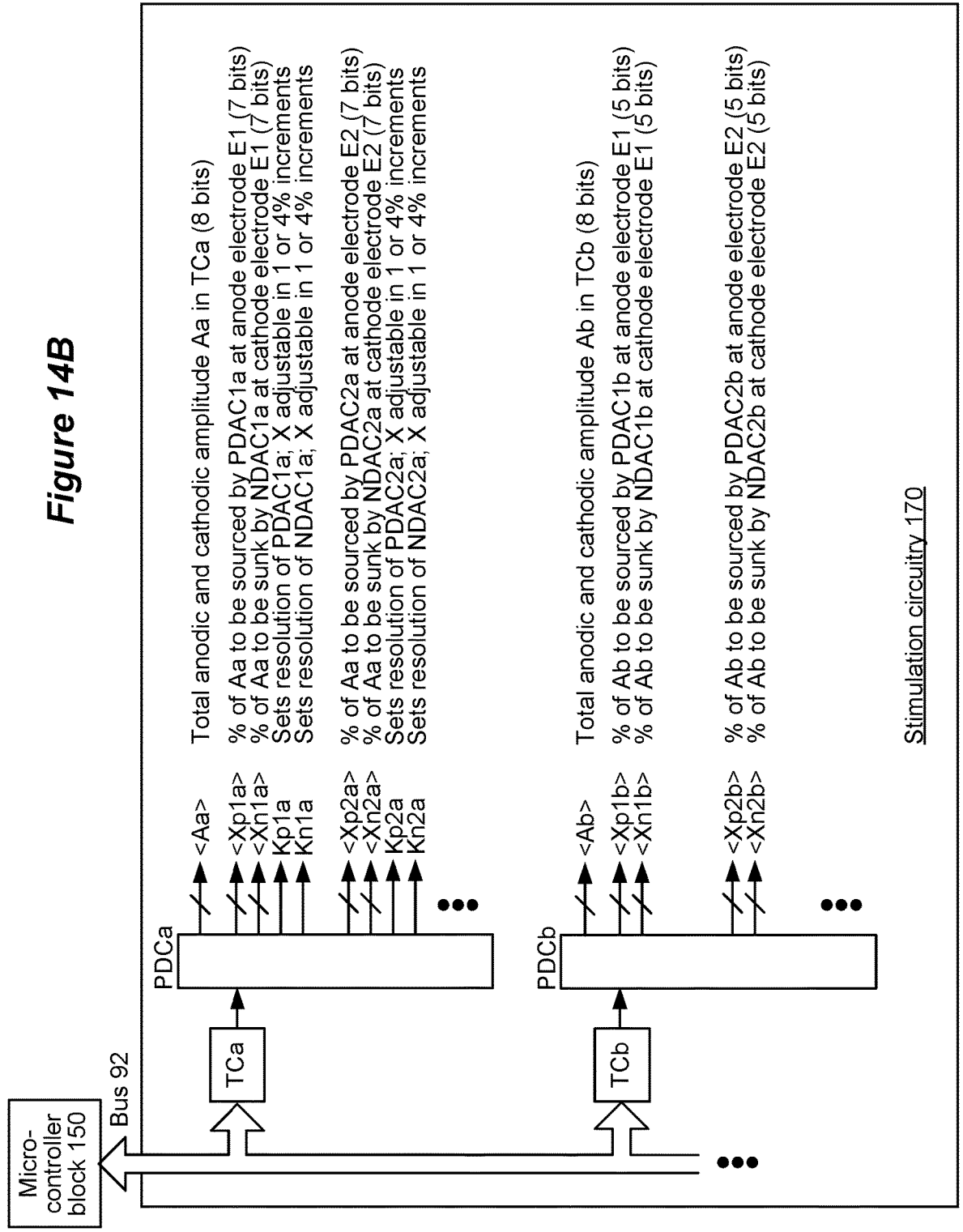

FIG. 14B summarizes the various control signals sent to the PDACs and NDACs in the example of FIG. 14A. In example, there are different Pulse Definition Circuits (PDCs) dedicated to each of the timing channels. Thus, PDCa provides the signals necessary to form stimulation pulses in TCa, including amplitude bus <Aa>, percentage control signals <X> and resolution control signals K. PDCb provides the signals necessary to form stimulation pulses in TCb, including amplitude bus <Ab> and percentage control signals <X>, but again in this example, there are no resolution control signals K in TCb. As shown, data for TCa is received from the microcontroller block 150 via bus 92, and stored in a timing channel register for use by PDCa. Data for TCb is similarly received and stored in a different timing channel register for use by PDCb. Notice then that PDCs form the pulses in their respective timing channels without consideration of the pulses being formed by other PDCs in other timing channels. Thus, in this example, and by contrast to the single PDC used in FIG. 8A, the PDCs do not consider whether their might be overlapping pulses in different timing channels, or whether an electrode might be common to more than one timing channel at any given time. (Microcontroller block 150 may still however consider such overlaps and conflicts).

Figure 14C:
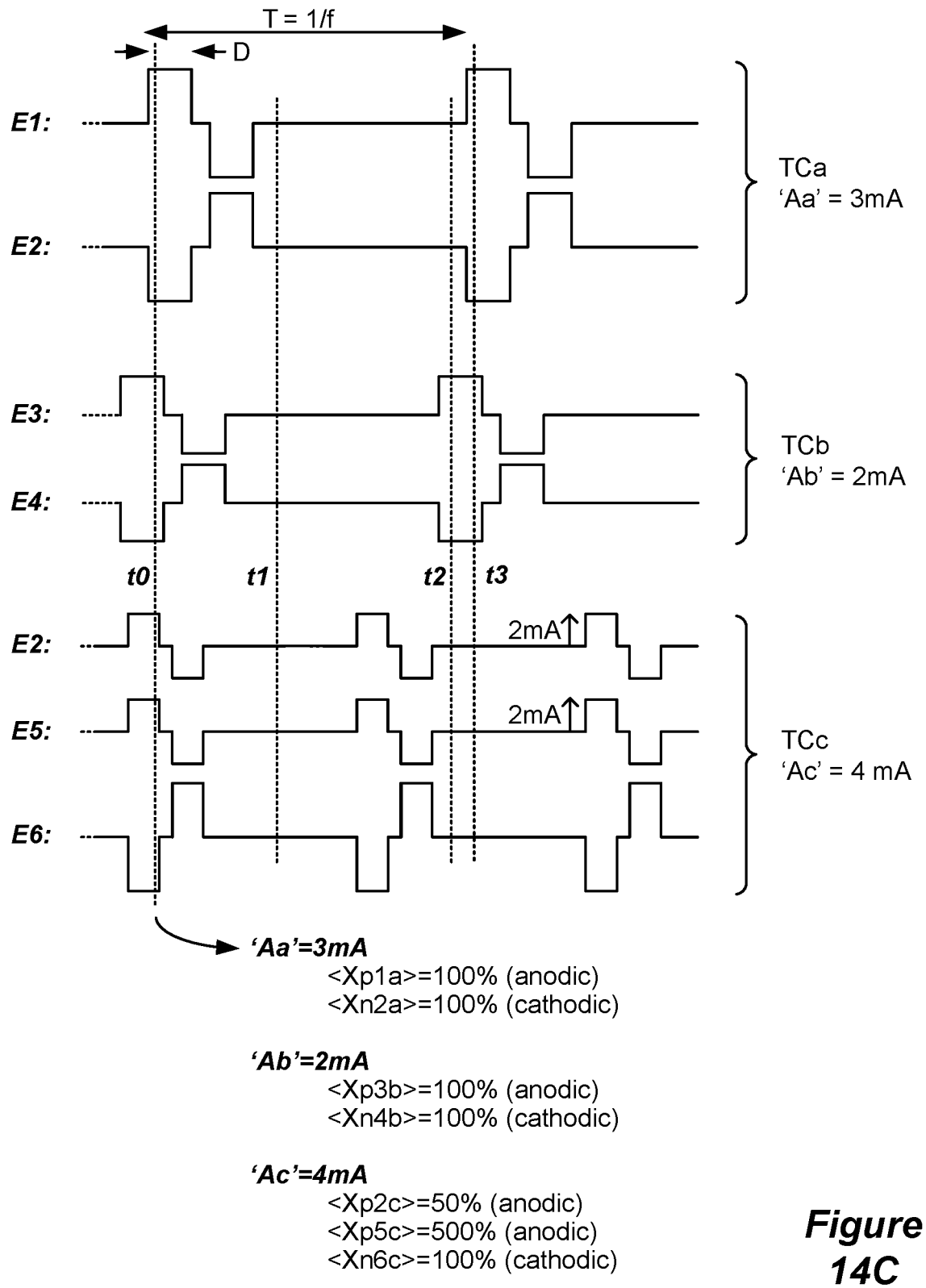

Independence of the timing channels is illustrated in FIG. 14C, which shows the same pulses illustrated earlier in FIG. 8B. At time t1, none of the timing channels TCa, TCb or TCc are issuing pulses, and so amplitudes 'Aa', 'Ab', and 'Ac' may be set to 0; all percentage bus signals <X> in all timing channels may be set to 0 at these times as well.

At time t2, pulses are only issued in timing channel TCb. Accordingly, PDCb sets 'Ab'=2, <Xp3b>=100%, and <Xn4b>=100%, which causes PDAC3b to issue +2 mA and NDAC4b to issue −2 mA, forming the desired pulses at anode electrode E3 and cathode electrode E4. All other amplitudes ('Aa', 'Ac') as well as their corresponding percentage bus control signals (<X>) are set to 0.

At time t3, pulses are issued in both of timing channels TCa and TCb. However, because these timing channels are independent, there is no need to consider the relative amplitudes 'Aa' and 'Ab' in each, or otherwise adjust the percentage control signals in light of the overlap. Thus, PDCa sets 'Aa'=3, <Xp1a>=100%, and <Xn2a>=100% which causes PDAC1b to issue +3 mA and NDAC2b to issue −3 mA, forming the desired pulses at anode electrode E1 and cathode electrode E2 specified by TCa. PDCb sends the same control signals as during time t2 to form the pulses at electrodes E3 and E4.

Time t0 shows a more extensive overlap between the pulses in all of timing channels TCa, TCb, and TCc, but again the independence of the PDCs and timing channels makes definition of the currents at this time more straightforward, and FIG. 14C shows the signals issued by PDCa, PDCb, and PDCc at this time. In this example, the conflict presented by electrode E2 being simultaneously specified as both an anode (in TCc) and a cathode (in TCa) results in shorting current (i.e., 2 mA) internally to the ASIC from PDAC2c to NDAC2a, similar to what was discussed earlier (FIG. 8B).

Figure 14D:
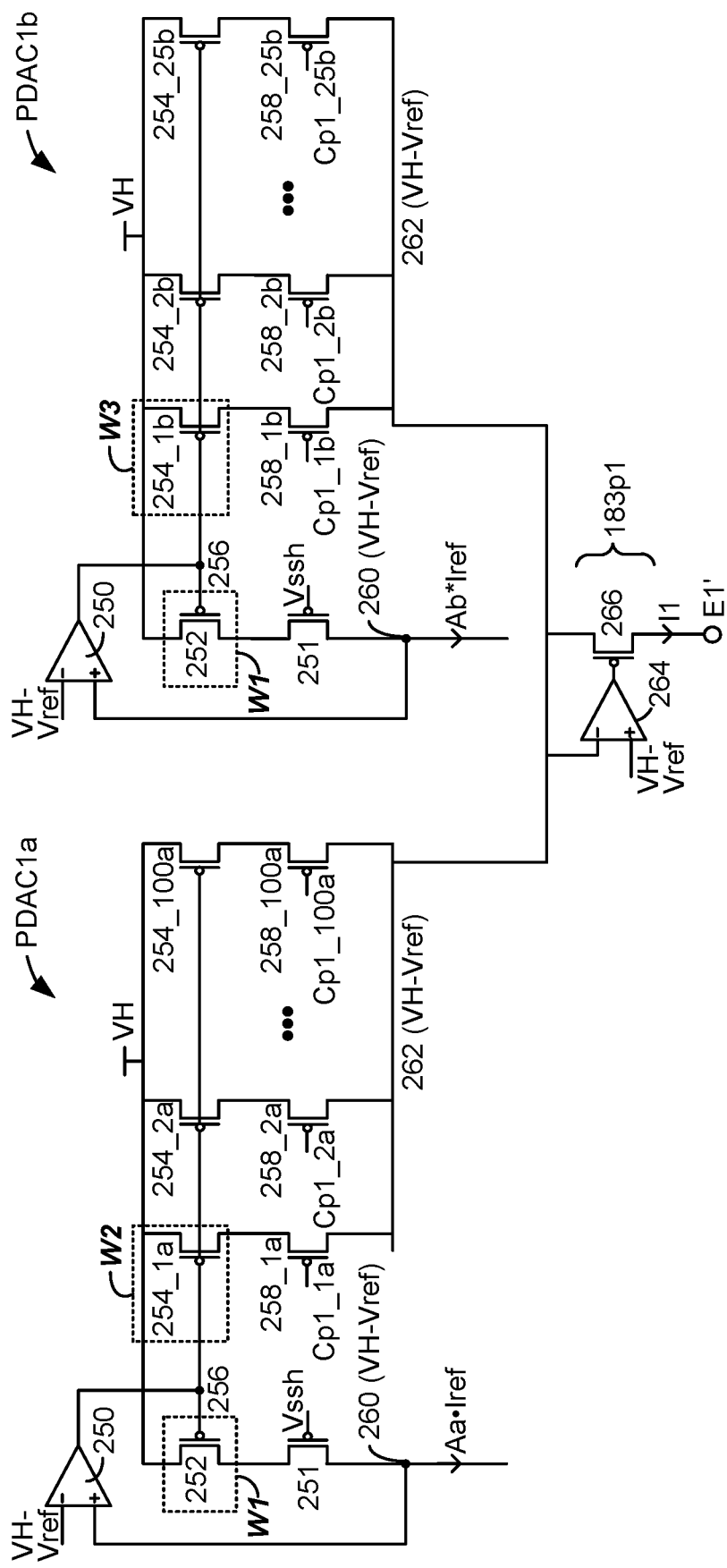
Figure 14E:
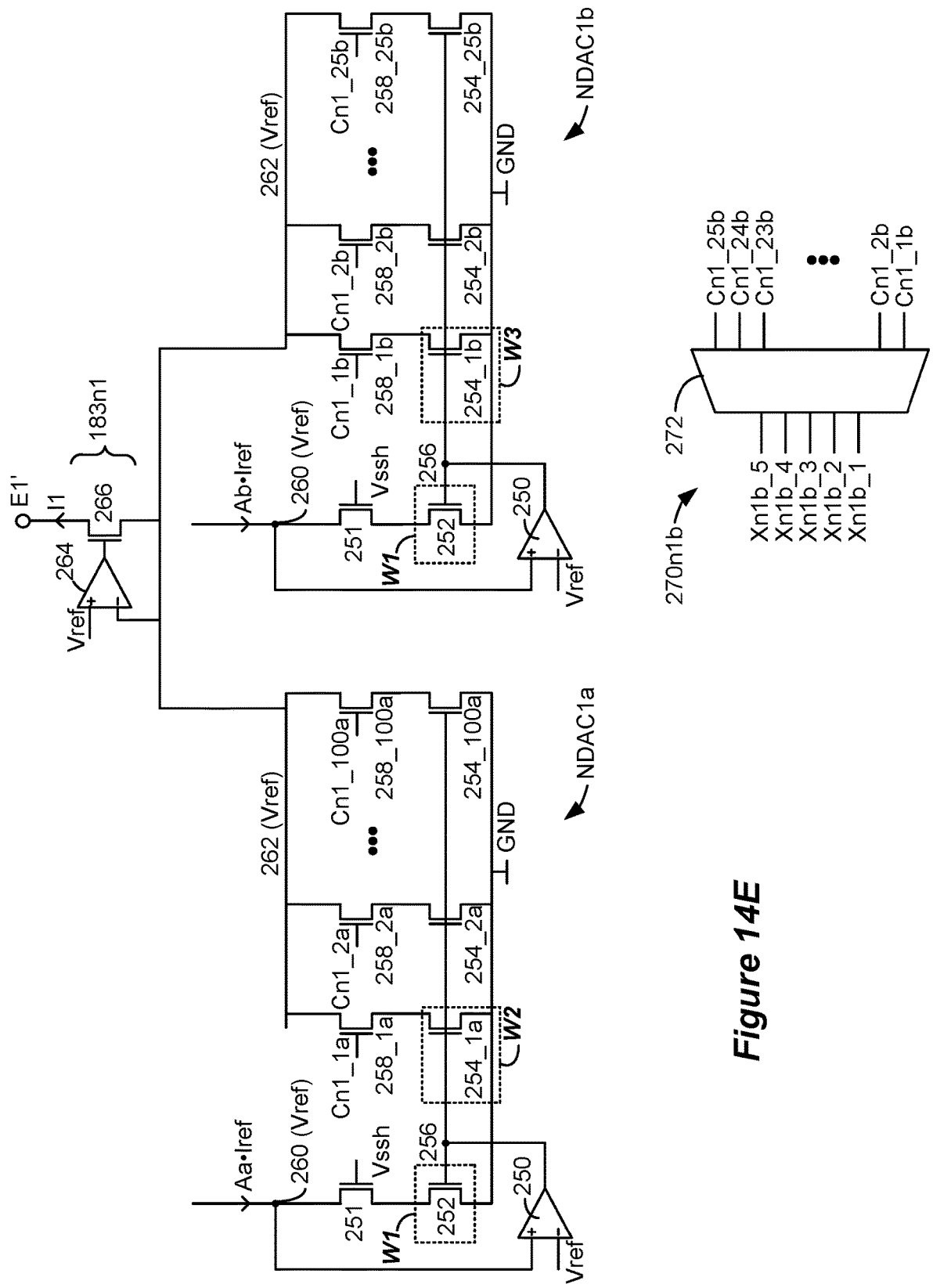

FIG. 14D shows PDAC1a and PDAC1b, while FIG. 14E similarly shows NDAC1a and NDAC1b, that service electrode node E1'. As before, these circuits are symmetrical, and the NDACs of FIG. 14E are discussed.

NDAC1a is essentially the same as NDAC1 described earlier (FIG. 9B), and has 100 branches controlled by switch control signals Cn1_100a: 1a. These switch control signals are generated from the percentage control signals <Xn1a> using logic circuitry 270n1a, which would be similar to logic circuitry 270n1 illustrated earlier (FIG. 12A). Logic circuitry 270n1a may once again alter generation of the switch control signals based on resolution control signal Kn1a, thus allowing NDAC1a to steer current in 1% (high resolution) or 4% (low resolution) increments. Notice that NDAC1a receives amplified reference current Aa*Iref from master DAC 180a and distributor 182a (FIG. 14A).

NDAC1b, by contrast, receives amplified reference current Ab*Iref from master DAC 180b and distributor 182b. NDAC1b is also structurally different in this example in that it has only 25 branches controlled by switch control signals Cn1_25b: 1b. As mentioned earlier, NDAC1b (actually all PDACs and NDACs operating in timing channel TCb) do not have an adjustable resolution, with each steering current in 4% (low resolution) increments. As a result, logic circuitry 270n1b servicing NDAC1b would be different from logic circuit 270n1a, and would not receive a resolution control signals. A simple illustration of logic circuitry 270n1b is provided in FIG. 14E, which essentially comprises only the thermometer decoder 272 discussed earlier, which directly generates the switch control signals <Cn1b>. Notice in this example only five percentage control signal Xn1b_5:1 are needed to represent the 4% increments (i.e., from 0 to 25, or from 0% to 100%) that NDAC1b must produce. Similar to what was explained earlier for operation in a low resolution mode (e.g., FIG. 12A), notice that PDCb will divide the desired percentage by four and issue that value in binary on percentage control signals Xn1b_5:1.

Another difference of NDAC1b relates to the amplification that each of the branches provides to Ab*Iref. Notice in NDAC1b that the branch transistors 254 are made with a width W3 that is different from the width W2 of the branch transistors 254 in NDAC1a. (The width of the resistance transistor 252 in both NDACs can remain the same at W1). More specifically, in the illustrated example, W2/W1=10, W3/W1=40. This means that the current provided by each selected branch in NDAC1b is four times larger than the current provided by each selected branch in NDAC1a (assuming 'Aa'='Ab'). Notice then that NDAC1a and NDAC1b are each capable of providing the same maximum current to electrode E1 (e.g., −25.5 mA): NDAC1b has branches that carry four times the currents as in NDAC1a, but has only one-fourth of the number of branches.

FIG. 14E shows show other details relevant to the use of two NDACs at each electrode. First, the NDACs share a common output stage 183n1—op amp 264 and output transistor 266—with the tops of the branches in each (node 262) being connected to the bottom of the transistor. Thus, the current in any selected branch in either NDAC1a or NDAC1b will sum at this node 262 and be presented to the electrode node E1'. Also different is the distribution of the reference voltage Vref, which is provided directly to the op amp 250 in each NDAC, and to the op amp 264 in the output stage 183n1.

Generally speaking, if IPG 10 is programmed to provide pulses in only a single timing channel, it is preferred that the microcontroller block 150 assign such pulses to timing channel TCa. This is because TCa—by virtue of PDACia and NDACia and their high number of branches—has the capability to provide both high and low resolutions of current, depending on the value of the resolution control signals Kpia and Knia. This thus allows a clinician or patient to adjust the currents at the electrodes in smaller increments if necessary or desired.

If IPG 10 is programmed to provide pulses in more than one timing channel, the microcontroller block 150 may consider the currents required, and assign the pulses to appropriate timing channels and thus to appropriate PDACs and NDACs. This is shown for example in FIG. 14F, which shows pulses being issued in two timing channels. The pulses at the top comprise only one anode and one cathode, and thus will receive 100% of the total anodic and cathode current ('Ab'=2.4). This can be generated by the low resolution mode PDACs and NDACs dedicated to timing channel TCb, and so the microcontroller block 150 could assign these pulses to this timing channel. By contrast, the pulses at the bottom have (at time t0) two cathode electrodes E1 and E2, each providing 50%. Because the low-resolution, 25 branch PDACs and NDAC in TCb can only split the total current ('Aa'=3.4 mA) in 4% increments, a 50%/50% split cannot be realized (at best, only a 48%/52% split could be realized). Thus, the microcontroller block 150 would preferably assign these pulses to timing channel TCa, which can produce a 50%/50% split in high resolution mode.

Figure 14F:
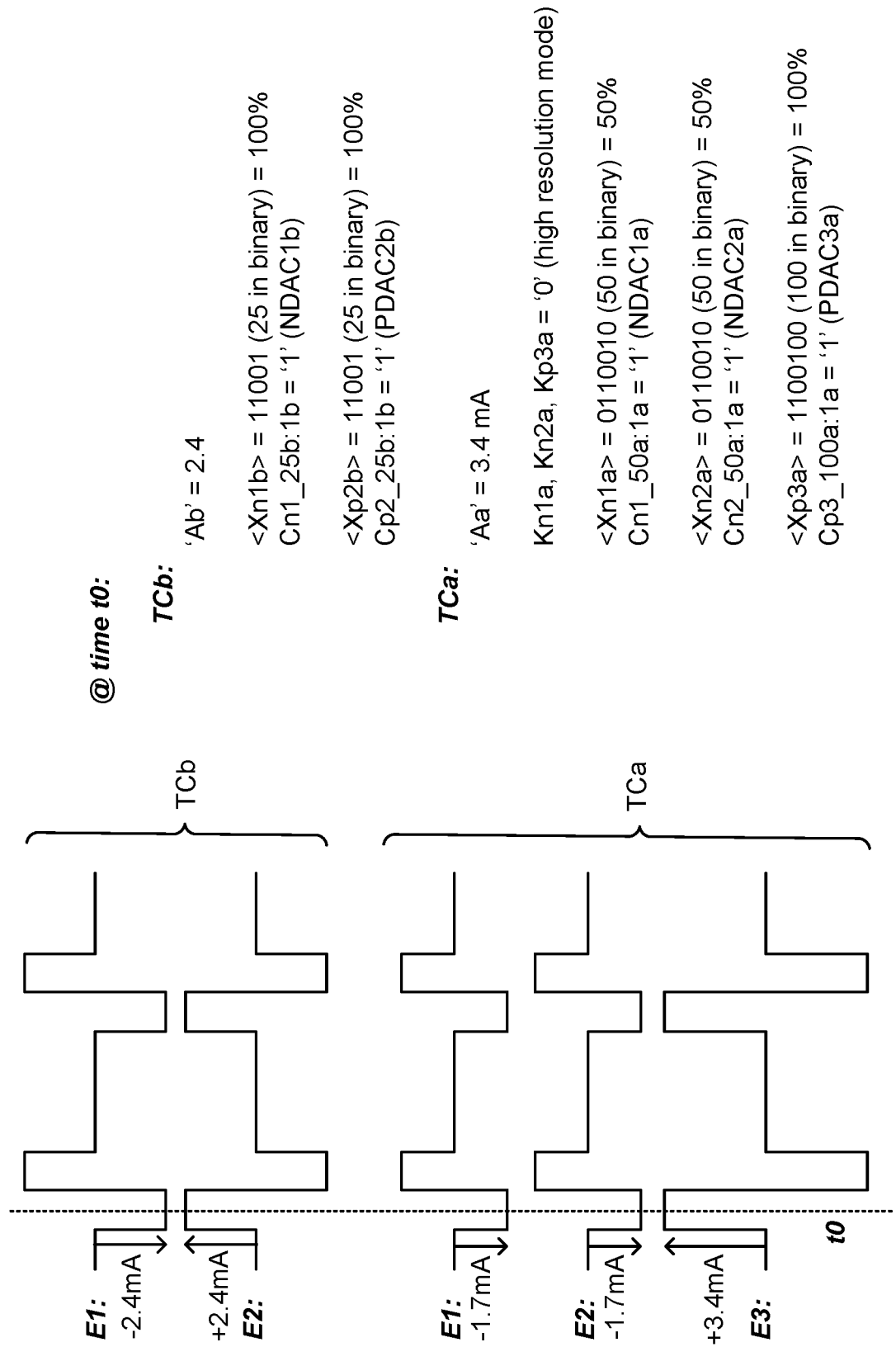

FIG. 14F also shows the control signals issued in the two timing channels TCa and TCb necessary to provide the desired current at the electrodes at time t0. A total anodic and cathodic amplitude of 'Ab'=2.4 mA is set in timing channel TCb. Further, each electrodes' TCb percentage bus, <Xn1b> which sets E1 as a cathode, and <Xp2b> which sets E2 as an anode, are set to 100%. As explained earlier, PDCb divides this desired percentage by four (100%/4), and thus issues 25 in binary on the percentage control signals. This causes all 25 branches in NDAC1b (Cn1_25b:1b) and all 25 branches in PDAC2b (Cp2_25b: 1b) to be asserted. Notice that no resolution control signal is necessary or provided in TCb.

A total anodic and cathodic amplitude of 'Aa'=3.4 mA is set in timing channel TCa, and the resolution control signals in timing channel TCa for the implicated DACs-NDAC1a, NDAC2a, and (possibly) PDAC3a (Kn1a, Kn2a, Kp3a)—are set to '0' to have these DACs operate in the high resolution mode. Further, the cathode electrodes' percentages busses in timing channel TCa, <Xn1a> for E1 and <Xn2a> for E2, are set to 50%. The anode electrode's percentage bus in timing channel TCa, <Xp3a> for E3, is set to 100%. This causes 50 branches in NDAC1a (Cn1_50a: 1a), 50 branches in NDAC2a (Cn2_50a:1a), and all 100 branches in PDAC3a (Cp3_100a:1a) to be asserted.

The effect at electrode E1 (for example) at time t0 can be better appreciated by reviewing NDAC1a and NDAC1b in FIG. 14E. Because all 25 branches in NDAC1b are turned on, those branches contribute 100% of 'Ab'=2.4 mA, which sinks −2.4 mA at node 262. Because 50 branches are on in NDAC1a, those branches contribute 50% of 'Aa'=3.4 mA, which sinks −1.7 mA at node 262. The summed effect is that electrode E1 sinks −2.4 mA+−1.7 mA=−4.1 mA from electrode E1 at time t0.

As noted earlier, the PDAC/NDAC pairs (e.g., PDACia/NDACia; PDACib/NDACib, etc.) at each electrode can all be built the same, and in this regard, each of these pairs can be built with a higher number of branches (e.g., NDAC1a), with resolution being controllable. This however increases the complexity of the signaling on the chip, due to the overhead necessary to generate the 100 switch control signals <C> for each PDAC and NDAC at each electrode (as well as the overhead of the resolution control signals). By contrast, using set lower-resolution PDACs and NDACs at the electrodes with a lower number of branches (e.g., NDAC1b) decreases this complexity. Having both types of PDACs and NDACs at the electrodes (e.g., NDAC1a and NDAC1b) can be a reasonable trade off, as this permits at least one timing channel to have high resolution current adjustment and steering (e.g., NDAC1a), and other simpler timing channels (NDAC1b, etc.) that can be run with lower-resolution adjustment capability. In a preferred example, each electrode can include four PDAC/NDAC pairs, with one pair comprising high resolution DACs with a high number of branches (e.g., PDAC1a/NDAC1a) running in a first timing channel (e.g., TCa), and three pairs comprising low resolution DACs with a smaller number of branches (e.g., PDAC1b/NDAC1b, PDAC1c/NDAC1c, PDAC1c/NDAC1c) running in three other timing channels (e.g., TCb, TCc, and TCd).

In a further modification, the resolution of all PDACs and NDACs can be set, thus obviating the need for resolution control signals (K) altogether. In this instance, the resolution of a given PDAC or NDAC can simply be set by the number of branches it has: for example 100 branches would provide a 1% resolution; 50 branches would provide a 2% resolution, 25 branches would provide a 4% resolution, etc. While not strictly necessary, it may be advisable to vary the amount by which each branch amplifies the reference current (A*Iref) in accordance with the resolution at hand, so that each PDAC or NDAC can provide the same maximum amount of current. For example, if 100 branches are used, each branch may amplify A*Iref by 10 (by adjusting W2/W1 as described earlier); if 50 branches are used, each branch may amplify A*Iref by 20; if 25 branches are used, each branch may amplify A*Iref by 40, etc.

In another alternative, more than one PDAC, NDAC, or PDAC/NDAC pair, could be assigned to a single timing channel. For example, PDAC1a/NDAC1a and PDAC1b/NDAC1b could be assigned to TCa and controlled by a PDCa; PDAC1c/NDAC1c and PDAC1d/NDAC1d could be assigned to TCb and controlled by a PDCb, etc. Such assignment could be permanent, or assignment of particular DACs to timing channels may be adjustable, such that PDAC1a/NDAC1a and PDAC1b/NDAC1b can be assigned to TCa at one time, or with PDAC1a/NDAC1a assigned to TCa and PDAC1b/NDAC1b assigned to TCb at another time.

As noted earlier, the improved DAC circuitry 172 can include different power supply voltages (compliance voltage VH, Vssh, Vcc, ground) defining a high power domain (VH/Vssh) and a low power domain (Vcc/GND). Low power domain Vcc/GND is more straight forward, because Vcc and ground may not change, and because Vcc can be generated from the voltage of the battery 14 (FIG. 1C) in the IPG 10 (see 204, FIG. 15B). By contrast, the compliance voltage VH can vary. Variation of the compliance voltage VH was explained briefly in the Introduction, and is elaborated upon further with respect to FIG. 15A. The resistance through the patient tissue, Rt, may not be known or may change over time, and hence the voltage dropped across the tissue in response to a stimulation current I (Vrt=I*Rt) may also change. Measuring the voltage drops across an active PDAC (Vp) and an active NDAC circuit (Vn) can assist in determining the tissue's voltage drop and resistance, and hence whether compliance voltage VH should be increased or decreased. Thus, in FIG. 15A, the compliance voltage generator block 76 (FIG. 4B) that produces the compliance voltage VH receives the measured PDAC and NDAC voltages drops Vp and Vn, and adjusts compliance voltage VH accordingly.

Further, the compliance voltage VH may be set to voltages that are relatively large, such as from 6 to 15 Volts. Higher voltage requirements have generally required PDACs and NDACs to be formed of special high-voltage transistors. Such high-voltage transistors are generally larger and more complicated to fabricate compared to more-standard, smaller logic transistors, because they are designed to function when receiving high voltages at their gates (i.e., Vg=0 to VH), and when receiving high voltages between their drains and sources (i.e. Vds =0 to VH). Even if the compliance voltage is normally not required to operate at its maximum voltage (e.g., 15V), DAC circuitry transistors have traditionally been built to withstand the possibility of high voltages, which complicates design of the ASIC.

It is beneficial to provide circuitry operating in low and high power domains in the DAC circuitry 172, because this can enable many transistors in the DAC circuitry 172 to be made from more-standard, smaller logic transistors otherwise generally used to form logic gates in the ASIC 160. For example, and preferably, if Vssh is set to 3.3 Volts lower than VH in the high power domain, low voltage transistors can be used in such high power domain circuits, so long as any control signals to such transistors are also biased in this domain. Likewise, and preferably if Vcc is set to 3.3 Volts higher than ground in the low power domain, low voltage transistors can be used in such low power domain circuits, again so long as any control signals to such transistors are also biased in this domain.

FIG. 15B shows generator circuitry 202, 204 used respectively to generate voltages Vssh and Vcc. Both of these generators 202, 204 comprise linear voltage regulators and include an op amp 206 that controls a pass transistor 210 to set Vssh and Vcc. As these circuits are disclosed and discussed in U.S. Patent Application Publication 2018/0071520, they are not further discussed here. Note though that even though VH may vary as described earlier, the output of Vssh generator 202 is always (in this example) 3.3 V lower than VH, as set by the resistor R and current source 208. Note also that Vcc may also be used to power other circuitry in the IPG 10, such as various functional blocks included in the ASIC 160 (FIG. 4B).

Figure 16A:
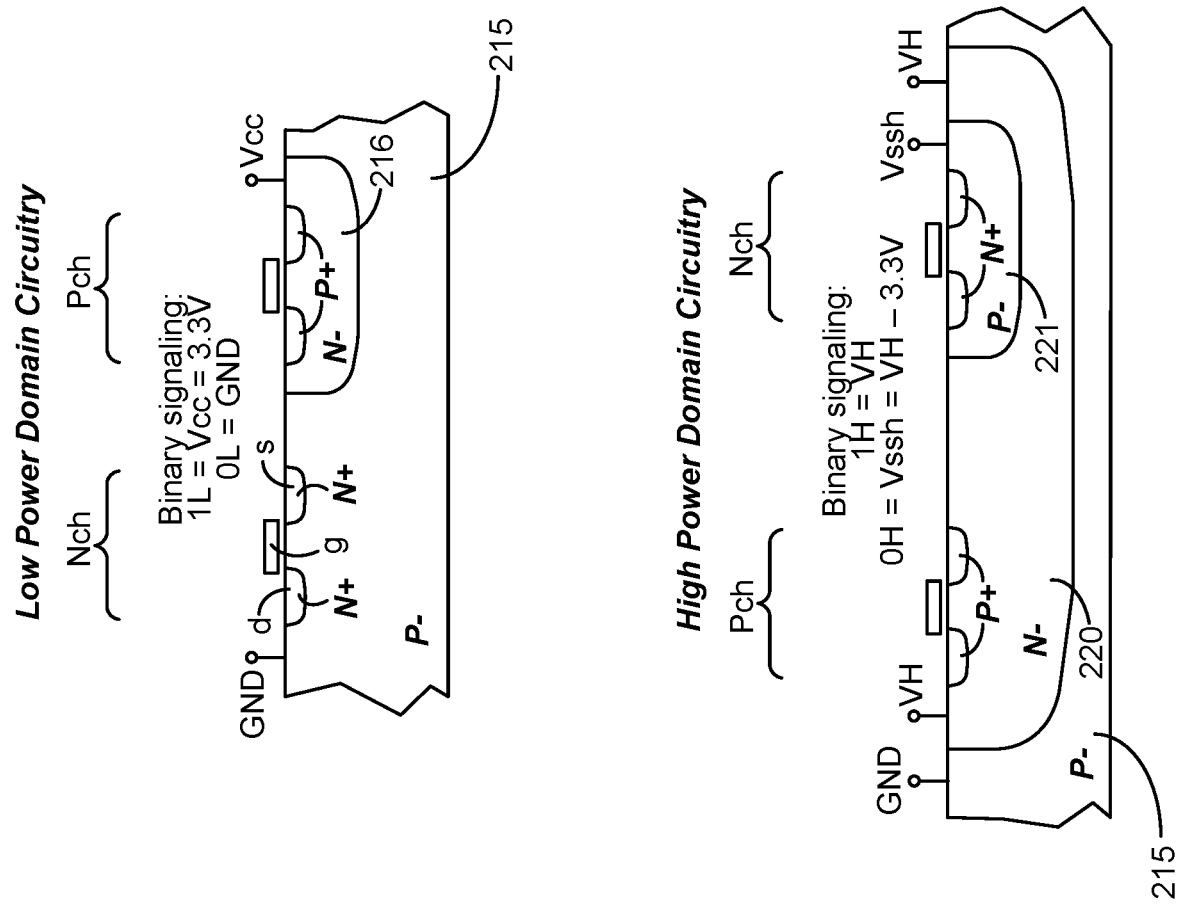
FIG. 16A shows cross sections of the N- and P-channel transistors used in circuitry powered in the low and high power domains, and shows how they are biased.

As noted earlier, the transistors in a particular power domain are preferably biased in accordance with that domain. This is shown in FIG. 16A, which shows cross-sectional views of the monolithic substrate 215 of the ASIC 160. Circuitry in low and high power domains include both low-voltage N-channel (Nch) and low-voltage P-channel (Pch) transistors. For example, N-channel transistors in the high power domain include transistors 192-200 in the distributor 182p (FIG. 7A), and any N-channel transistors in op amps 250 or 264 in the PDACs (FIG. 9A). P-channel transistors in the high power domain include transistors 184-186 in the master DAC 180p (FIG. 7A), any P-channel transistors in op amps 250 or 264 in the PDACs (FIG. 9A), and dummy transistors 251, resistance transistors 252, and branch and switch transistors 254 and 258 in the PDACs (FIG. 9A). N-channel transistors in the low power domain include transistors 184-186 in the master DAC 180n (FIG. 7B), any N-channel transistors in op amps 250 or 264 in the NDACs (FIG. 9B), and dummy transistors 251, resistance transistors 252, and branch and switch transistors 254 and 258 in the NDACs (FIG. 9B). P-channel transistors in the low power domain include transistors 192-200 in the distributor 182n (FIG. 7B), and any P-channel transistors in op amps 250 or 264 in the NDACs (FIG. 9B).

As FIG. 16A shows, the low power domain transistors are essentially formed as is common in CMOS technologies, with the N-channel transistors built into a grounded P-type substrate 215, and the P-channel transistors built in an N-well 216 biased to Vcc=3.3 V. In other words, the low power domain transistors are biased to the Vcc/ground low power domain. The high power domain transistors are biased to the VH/Vssh high power domain. Thus, a high-voltage N-well 220 is formed in the P-type substrate 215, and biased to the compliance voltage VH. This high voltage N-well 220 may be deeper and significantly graded so that it may retain the high compliance voltage VH (which may be up to 15 Volts) without breaking down to the grounded substrate 215. P-channel transistors are built in the high-voltage N-well 220. A P-well 221 is formed in the N-well 220, in which the N-channel transistors may be built.

As explained further below, the logic levels (e.g., control signals) presented to the transistors in the power domains are also biased in accordance with each power domain. Thus, a logic '0' in the low power domain (0L) equals ground, while a logic '1' (1L) equals Vcc=3.3V. A logic '0' in the high power domain (0H) equals Vssh, while a logic '1' (1H) equals VH—Vssh. Thus, voltage drops in the low and high power domain transistors will not exceed e.g., 3.3 Volts, and thus low-voltage transistors can be used. (The only high-voltage transistors that may be warranted in the design of DAC circuitry 172 are the output transistors 266 (FIGS. 9A, 9B) used to pass currents to the selected electrode nodes 61*a*, and transistors used to form the op amps 264. As such, the op amps 264 may also receive high voltage power (VH), although this detail isn't shown in the figures).

Figure 16B:
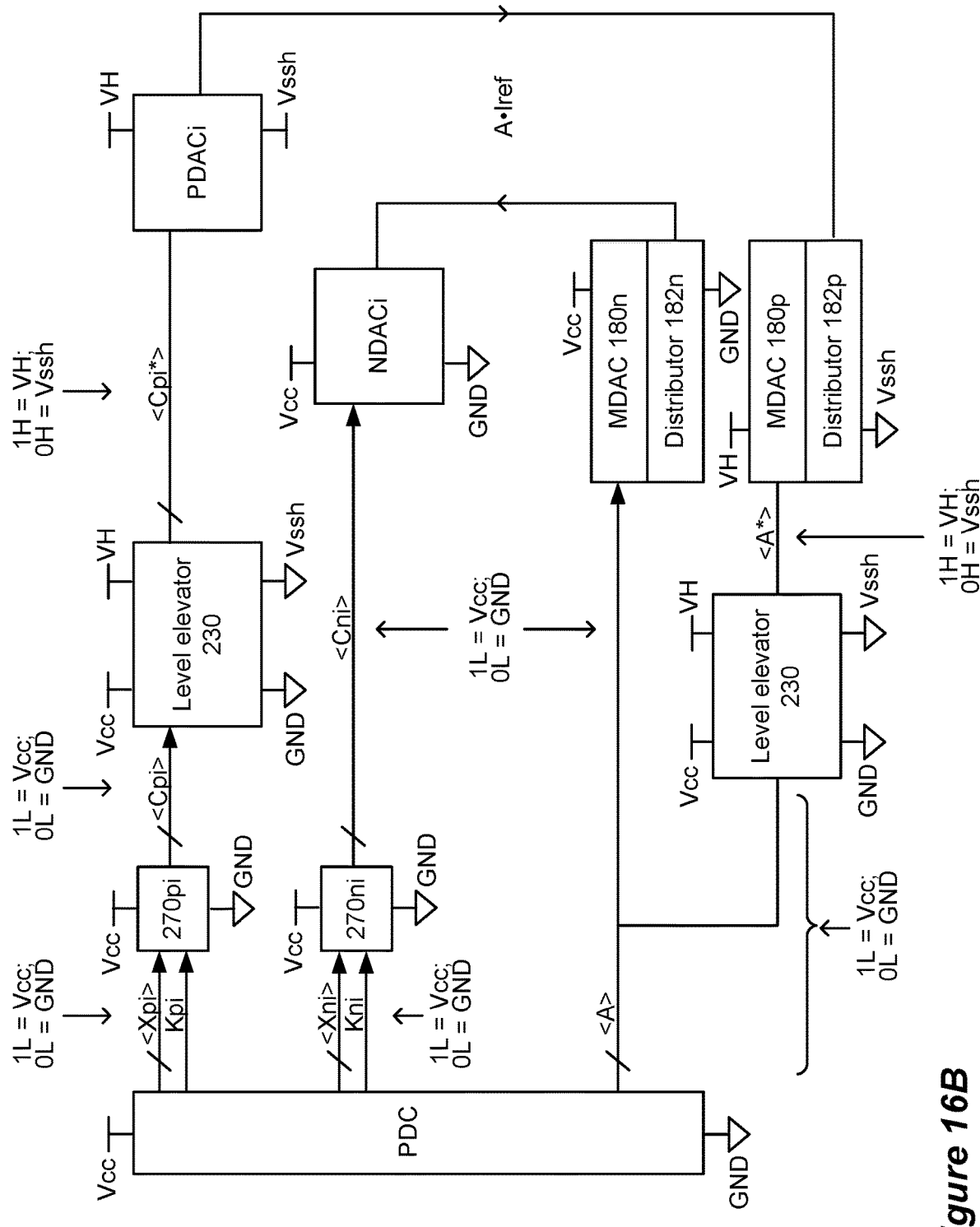
FIG. 16B shows how control signals sent to the PDACs can be level elevated from the low power domain to the high power domain.
Figure 16C:
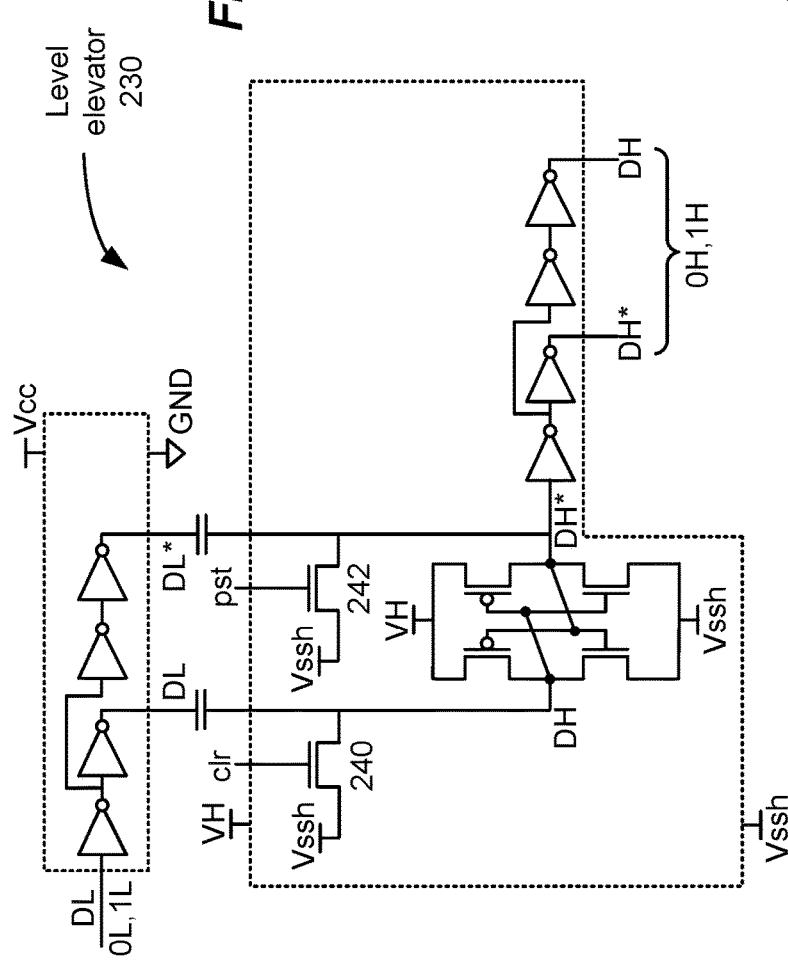
FIG. 16C shows example level elevation circuitry for each control signal.

How control signals sent to various transistors in the DAC circuitry 172 are referenced to the appropriate power domain is discussed next. Control signals are ultimately issued from one or more pulse definition circuits (PDCs), as discussed earlier. As shown in FIG. 16B, because the PDC(s) are powered by Vcc and ground, NDAC control signals (<Xni>, Kni), PDAC control signals (<Xpi>, Kpi), and the amplitude bus <A> are issued with low-power-domain logic states (i.e., 0L, 1L).

The NDAC control signals (<Xni>, Kni) and the PDAC control signals (<Xpi>, Kpi) are sent to logic circuitries 270*ni* and 270*pi* used to convert these signals into switch control signals <Cni> and <Cpi> for the NDACs and the PDACs, as already discussed (e.g., FIG. 12A). Because logic circuitries 270*ni* and 270*pi* are also biased in the lower power domains, the switch control signals <Cni> and <Cpi> are also issued with low-power-domain logic states 0L and 1L.

Because the NDACs are also biased in the low power domain, the NDACs can receive the switch control signals <Cni> directly as issued by logic circuitry 270*ni*. By contrast, the PDACs operate in the high power domain, and therefore, each <Cpi> control signals destined for the PDACs is sent to a level elevator 230 to increase the voltage of the signal, as shown in FIG. 16B. Circuitry for the level elevator 230 is shown in detail in FIG. 16C. Because operation of level elevator 230 is disclosed and discussed in U.S. Published Patent Application 2018/0071520, it is not further discussed in detail here. Briefly, each individual data bit in <Cpi> (DL, which may comprise either 0L or 1L) is presented to the level elevator 230, which operates to boost the voltages of that data bit from low-power-domain voltages to high-power-domain voltages (DH, which may comprise either 0H or 1H), thus matching the high power domain to which the PDACs are biased. Notice that the level elevator can provide both true (DH) and complementary (DH*) outputs. The complementary outputs <Cpi*> are preferably used as these will enable the P-channel switches 258 (FIG. 9A) in the PDACs with the correct logic state.

(Transistors 240 and 242 in the level elevators 230 receive signals clear (clr) and preset (pst), which are useful upon initial powering of the ASIC 160 because the latches 244 in the level elevators 230 may power to an indefinite state that is inconsistent with the input, DL. Thus, one of these signals dr or pst can be asserted after power-up to pre-condition the latch 244 to match the current input value DL. For example, if DL=0L, dr can be asserted; if DL=1L, pst can be asserted).

The bits in amplitude bus <A> as issued by the PDC in the low power domain (0L, 1L) may be sent directly to the MDAC 180*n*, as they match the low power domain to which MDAC 180*n* and its distributor 182*n* are biased. By contrast, the MDAC 180*p* and its distributor 182*p* contain transistors biased in the high power domain, and thus the amplitude signals <A> must be shifted to the high power domain (0H, 1H) using level elevators 230. Again, the complementary outputs <A*> are preferably used at the level elevator 230 outputs as these will enable the P-channel switches 184 (FIG. 7A) in the MDAC 180*p* with the correct logic state.

Figure 16D:
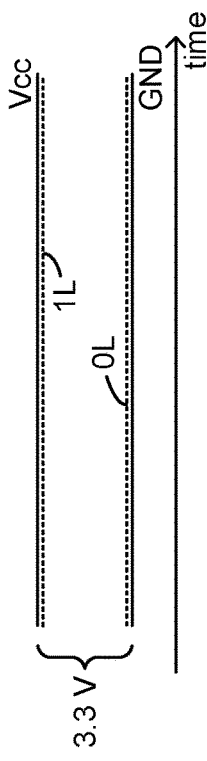
FIG. 16D shows how the high power domain and its logic levels can vary as the compliance voltage changes.

Note that the high power domain transistors can use low-voltage transistors even though the compliance voltage VH may change over time. If VH changes, so too will Vssh, as dictated by the operation of the Vssh generator 202 (FIG. 15B), which always maintains a 3.3 V difference between VH and Vssh in the high power domain. If VH and Vssh change, so will the biasing of the high power domain transistors in the PDACs (FIG. 16A), and so too will the voltages of the logic states (0H, 1H) presented to those transistors (per operation of the level elevators 230 of FIG. 16C). This is shown in FIG. 16D, which shows that as the compliance voltage VH varies over time, so too does Vssh, and so do the voltages of the logic states 0H, 1H produced by the level elevators 230. Moreover, a constant difference (e.g., 3.3 V) is also maintained between the two logic states despite variance in VH and Vssh. FIG. 16D also shows the power supplies for the low power domain (Vcc, ground) and the voltages of the logic states in this low power domain (0L, 1L), which also maintain a constant difference (again, e.g., 3.3 V).

While disclosed in the context of an implantable pulse generator, it should be noted that the improved stimulation circuitry 170 and DAC circuitry 172 could also be implemented in a non-implantable pulse generator, such as an External Trial Stimulator (ETS). See, e.g., U.S. Pat. No. 9,259,574 (describing an ETS).

Because defining a positive or negative current can be a matter of convention, anodic currents are not necessarily positive (or sourced to the tissue, such as from the disclosed PDACs) and cathodic currents are not necessarily negative (or sunk from the tissue, such as from the disclosed NDACs), as has been described to this point. Instead, anodic currents can also be considered as negative (sunk from the tissue, such as are producible by the disclosed NDACs), and cathodic currents can be considered as positive (sourced to the tissue, such as are producible by the disclosed PDACs). What is important then is that anodic and cathodic currents have opposite polarities.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A pulse generator, comprising:
   a plurality of electrode nodes, each electrode node configured to be coupled to an electrode configured to contact a patient's tissue;
   a first digital-to-analog converter (DAC) configured to receive digital data specifying a magnitude of a total anodic current amplitude to be produced at the electrode nodes, and to produce a first current with a magnitude indicative of the total anodic current amplitude;
   a plurality of first calibration circuits each configured to receive the first current, wherein each of the first calibration circuits is controllable to produce a different second current as a function of the first current; and
   a plurality of second DACs each associated with one of the electrode nodes, wherein each second DAC is configured to receive one of the second currents, wherein each of the second DACs is configured when selected to amplify its received second current to produce an anodic stimulation current at its associated electrode node.

2. The pulse generator of claim 1, wherein each of the first calibration circuits is controllable to produce its second current as a linear function of the first current.

3. The pulse generator of claim 2, wherein each of the first calibration circuits is controllable to provide a gain, an offset, or both to the first current when producing its second current.

4. The pulse generator of claim 1, wherein each of the first calibration circuits is independently controllable via unique first control signals received at each first calibration circuit to produce its second current.

5. The pulse generator of claim 1, wherein each of the first calibration circuits comprises a gain DAC configured to impart a gain to the first current when producing its second current.

6. The pulse generator of claim 1, wherein each of the first calibration circuits comprises an offset DAC configured to impart an offset to the first current when producing its second current.

7. The pulse generator of claim 1, wherein the first DAC is configured to receive a reference current, wherein the magnitude of first current comprises a scalar of the reference current.

8. The pulse generator of claim 1, wherein each of the first calibration circuits comprises a gain DAC configured to impart a gain to the first current when producing its second current, and wherein each of the first calibration circuits comprises an offset DAC configured to impart an offset to the first current when producing its second current.

9. The pulse generator of claim 1, wherein a sum of the anodic stimulation currents at the electrode nodes equals the total anodic current amplitude.

10. The pulse generator of claim 1, wherein the digital data further specifies a magnitude of a total cathodic current amplitude to be produced at the electrode nodes, wherein the first DAC is further configured to produce a third current with a magnitude indicative of the total cathodic current amplitude to be produced at the electrode nodes, wherein a polarity of the third current is opposite the first current, wherein the pulse generator further comprises:
   a plurality of second calibration circuits each configured to receive the third current, wherein each of the second calibration circuits is controllable to produce a different fourth current as a function of the third current; and
   a plurality of third DACs each associated with one of the electrode nodes, wherein each third DAC is configured to receive one of the fourth currents, wherein each of the third DACs is configured when selected to amplify its received fourth current to produce a cathodic stimulation current at its associated electrode node.

11. The pulse generator of claim 10, wherein each of the second calibration circuits is controllable to produce its fourth current as a linear function of the third current.

12. The pulse generator of claim 11, wherein each of the second calibration circuits is controllable to provide a gain, an offset, or both to the third current when producing its fourth current.

13. The pulse generator of claim 10, wherein each of the second calibration circuits is independently controllable via unique second control signals received at each second calibration circuit to produce its fourth current.

14. The pulse generator of claim 10, wherein each of the second calibration circuits comprises a gain DAC configured to impart a gain to the third current when producing its fourth current.

15. The pulse generator of claim 10, wherein each of the second calibration circuits comprises an offset DAC configured to impart an offset to the third current when producing its fourth current.

16. The pulse generator of claim 10, wherein each of the second calibration circuits comprises a gain DAC configured to impart a gain to the third current when producing its fourth current, and wherein each of the second calibration circuits comprises an offset DAC configured to impart an offset to the third current when producing its fourth current.

17. The pulse generator claim 10, wherein the magnitudes of the first and third currents are equal.

18. The pulse generator of claim 10, wherein a sum of the cathodic stimulation currents at the electrode nodes equals the total cathodic current amplitude.

19. The pulse generator of claim 18, wherein a magnitude of a sum of the anodic stimulation currents at the electrode nodes equals a magnitude of the sum of the cathodic stimulation currents at the electrode nodes.

20. A method for operating a pulse generator having a plurality of electrode nodes, each electrode node configured to be coupled to an electrode configured to contact a patient's tissue, the method comprising:
   receiving at the pulse generator digital data specifying a magnitude of a total anodic current amplitude to be produced at the electrode nodes;
   producing a first current with a magnitude indicative of the total anodic current amplitude;
   producing a plurality of different second currents from the first current, wherein each of the second currents is independently calibrated;
   receiving the independently-calibrated second currents at a plurality of second DACs, wherein each of the second DACs is associated with one of the electrode nodes; and
   selecting at least one second DAC to amplify its received second current to produce an anodic stimulation current at its associated electrode node.

* * * * *